(12) United States Patent
Buschmann et al.

(10) Patent No.: US 8,048,890 B2
(45) Date of Patent: Nov. 1, 2011

(54) SUBSTITUTED 1-OXA-2,8-DIAZA-SPIRO[4,5]DEC-2-ENE DERIVATIVES AND RELATED TREATMENT METHODS

(75) Inventors: Heinrich Helmut Buschmann, Esplugues de Llobregat (DE); Guenter Werner Englberger, Stolberg (DE); Tieno Germann, Aachen (DE); Hagen-Heinrich Hennies, Simmerath (DE); Corinna Maul, Aachen (DE); Bernd Sundermann, Aachen (DE); Joerg Holenz, Aachen (DE)

(73) Assignee: Gruenenthal GmbH, Aachen (DE)

( * ) Notice: Subject to any disclaimer, the term of this patent is extended or adjusted under 35 U.S.C. 154(b) by 1420 days.

(21) Appl. No.: 10/744,082

(22) Filed: Dec. 24, 2003

(65) Prior Publication Data

US 2004/0192916 A1 Sep. 30, 2004

Related U.S. Application Data

(63) Continuation of application No. PCT/EP02/06880, filed on Jun. 21, 2002.

(30) Foreign Application Priority Data

Jun. 25, 2001 (DE) .................................. 101 30 020

(51) Int. Cl.
*A61K 31/438* (2006.01)
*C07D 413/04* (2006.01)
(52) U.S. Cl. ......................................... 514/278; 546/19
(58) Field of Classification Search ................... 546/19; 514/278
See application file for complete search history.

(56) References Cited

U.S. PATENT DOCUMENTS

| 3,399,192 A | 8/1968 | Regnier et al. |
| 3,598,828 A | 8/1971 | Regnier et al. |
| 5,073,560 A | 12/1991 | Wu et al. |
| 5,760,029 A * | 6/1998 | Jadhav et al. ............ 514/210.16 |

FOREIGN PATENT DOCUMENTS

| WO | 9733887 | * | 9/1997 |
| WO | 9843962 | * | 10/1998 |

OTHER PUBLICATIONS

Dorwald F. A. Side Reactions in Organic Synthesis, 2005, Wiley: VCH, Weinheim p. IX of Preface.*

* cited by examiner

*Primary Examiner* — Rita Desai
(74) *Attorney, Agent, or Firm* — Crowell & Moring LLP

(57) ABSTRACT

Substituted 1-oxa-2,8-diaza-spiro[4,5]dec-2-ene compounds and processes for their production, the use thereof for producing pharmaceutical compositions, pharmaceutical compositions containing these compounds and methods of treatment using these compounds.

44 Claims, No Drawings

SUBSTITUTED 1-OXA-2,8-DIAZA-SPIRO[4,5]DEC-2-ENE DERIVATIVES AND RELATED TREATMENT METHODS

CROSS-REFERENCE TO RELATED APPLICATIONS

This application is a continuation of International Patent Application No. PCT/EP02/06880, filed Jun. 21, 2002, designating the United States of America, and published in German as WO 03/000699, the entire disclosure of which is incorporated herein by reference. Priority is claimed based on Federal Republic of Germany Patent Application 101 30 020.4, filed Jun. 25, 2001.

FIELD OF THE INVENTION

The present invention relates to substituted 1-oxa-2,8-diaza-spiro[4,5]dec-2-ene derivatives, and to processes for their production, to the use thereof for producing pharmaceutical compositions and to pharmaceutical compositions containing these compounds.

BACKGROUND OF THE INVENTION

The treatment of chronic and non-chronic pain conditions has great importance in medicine. There is a worldwide need for effective methods of treating pain. The urgent need for action for patient-friendly and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Conventional opioids, such as morphine, are extremely effective in the treatment of severe to the severest pain. However, their use is limited by the known side effects, for example respiratory depression, nausea, sedation, constipation and tolerance development. In addition, they are less effective in the event of neuropathic or incidental pain, from which patients with tumors suffer in particular.

Opioids deploy their analgesic effect by binding to membrane receptors belonging to the family known as G-protein-coupled receptors. The biochemical and pharmacological characterization of subtypes of these receptors has now roused hopes that subtype-specific opioids have a different profile of effects and side effects from, for example, morphine. Further pharmacological investigations have in the meantime affirmed the likelihood of the existence of a plurality of subtypes of these opioid receptors ($\mu_1$, $\mu_2$, $\kappa_1$, $\kappa_2$, $\kappa_3$, $\delta_1$ and $\delta_2$).

There are further receptors and ion channels which participate substantially in the pain development and pain transmission system, for example the so-called batrachotoxin-(BTX) binding site (=binding site 2) of the sodium channel or the NMDA ion channel through which a substantial proportion of synaptic communication takes place by controlling the exchange of calcium ions between the neuronal cell and its environment.

SUMMARY OF THE INVENTION

One object of the present invention is to provide analgesically effective compounds which are capable of treating pain, optionally including chronic and neuropathic pain. Furthermore, these substances should cause the fewest possible side effects, which conventionally occur when using opioids such as morphine, for example vomiting, nausea, dependency, respiratory depression or constipation.

The object is achieved by the analgesically effective substituted 1-oxa-2,8-diaza-spiro[4,5]dec-2-ene derivatives of general formula (I)

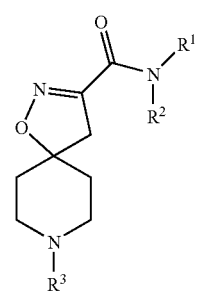

I optionally in the form of its racemates, its pure stereoisomers, in particular enantiomers or diastereomers, or in the form of blends of stereoisomers, in particular the enantiomers or diastereomers, in any mixing ratio; in the illustrated form or in the form of its acids or its bases or in the form of its salts, in particular the physiologically acceptable salts, more particularly preferably in the form of its solvates, in particular the hydrates, wherein $R^1$ and $R^2$ independently of one another represent H, $C_{1-18}$-alkyl, $C_{3-10}$-cycloalkyl, ($C_{1-12}$-alkyl)-$C_{3-10}$-cycloalkyl, aryl, ($C_{1-12}$-alkyl)-aryl, heterocyclyl, ($C_{1-12}$-alkyl)-heterocyclyl or NH—C(=O)-aryl, wherein at least one of the radicals $R^1$ and $R^2$ does not represent H, or together represent —$(CR^4R^5)_m$—$(CR^6R^7)_n$—Y—$(CR^8R^9)_p$—$(CR^{10}R^{11})_q$— where m, n, p and q respectively=0, 1, 2, 3, 4 or 5, with the proviso that m+n≧1 and p+q≧1, or —$CH_2$—$CH_2$—C(-aryl)=CH—$CH_2$—;

$R^3$ represents H, $SO_2R^{12}$ or $COR^{13}$;

$R^4$, $R^5$, $R^6$, $R^7$, $R^8$, $R^9$, $R^{10}$ and $R^{11}$ independently of one another represent H, $C_{1-10}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl or C(=O)$R^{14}$;

Y represents $CR^{15}R^{16}$, $NR^{17}$ or O;

$R^{12}$ and $R^{13}$ independently of one another represent $C_{1-10}$-alkyl, $C_{3-10}$-cycloalkyl, ($C_{1-6}$-alkyl)-$C_{3-10}$-cycloalkyl, aryl, ($C_{1-6}$-alkyl)-aryl, heterocyclyl, ($C_{1-6}$-alkyl)-heterocyclyl or $NR^{18}R^{19}$;

$R^{14}$ represents H, $C_{1-10}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl or $OR^{20}$;

$R_{15}$ and $R_{16}$ independently of one another represent H, $C_{1-10}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl or C(=O)$R^{21}$;

$R^{17}$ represents H, $C_{1-10}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl or C(=O)$R^{22}$;

$R^{18}$ and $R^{19}$ independently of one another represent H, $C_{1-10}$-alkyl, $C_{3-8}$-cycloalkyl, $C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl;

$R^{20}$ represents H, $C_{1-10}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl;

$R^{21}$ represents H, $C_{1-10}$-alkyl, $C_{3-8}$-cycloalkyl, $(C_{1-6}$-alkyl)-$C_{3-8}$ cycloalkyl, aryl, $(C_{1-6}$-alkyl)-aryl, heterocyclyl, $(C_{1-6}$-alkyl)-heterocyclyl or $OR^{23}$;

$R^{22}$ represents H, $C_{1-10}$-alkyl, $C_{3-8}$-cycloalkyl, $(C_{1-6}$-alkyl)-$C_{3-8}$-cycloalkyl, aryl, $(C_{1-6}$-alkyl)-aryl, heterocyclyl, $(C_{1-6}$-alkyl)-heterocyclyl or $OR^{24}$; and $R^{23}$ and $R^{24}$ independently of one another represent H, $C_{1-10}$-alkyl, $C_{3-8}$-cycloalkyl, $(C_{1-6}$-alkyl)-$C_{3-8}$-cycloalkyl, aryl, $(C_{1-6}$-alkyl)-aryl, heterocyclyl or $(C_{1-6}$-alkyl)-heterocyclyl.

These compounds according to the invention of general formula (I) have proven to be analgesically effective compounds. They can bind to the BTX binding site of the sodium channel and are NMDA antagonists with analgesic effect.

According to the invention, the terms "alkyl", "$C_{1-18}$-alkyl", "$C_{1-12}$-alkyl", "$C_{1-10}$alkyl", "$C_{1-8}$-alkyl", "$C_{1-6}$-alkyl", "$C_{1-4}$-alkyl", "$C_{1-3}$-alkyl" and "$C_{1-2}$-alkyl" include acyclic saturated or unsaturated hydrocarbon radicals, which can be branched or straight chained and unsubstituted or singly substituted or multiply identically or differently substituted, with (as in the case of $C_{1-18}$-alkyl) 1 to 18 (i.e. 1, 2, 3, 4, 5, 6, 7, 8, 9, 10, 11, 12, 13, 14, 15, 16, 17 or 18) or (as in the case of $C_{1-12}$-alkyl) 1 to 12 (i.e. 1, 2, 3, 4, 5, 6, 7, 8, 9, 10, 11 or 12) or (as in the case of $C_{1-10}$-alkyl) 1 to 10 (i.e. 1, 2, 3, 4, 5, 6, 7, 8, 9 or 10) or (as in the case of $C_{1-8}$-alkyl) 1 to 8 (i.e. 1, 2, 3, 4, 5, 6, 7 or 8) or (as in the case of $C_{1-6}$-alkyl) 1 to 6 (i.e. 1, 2, 3, 4, 5 or 6) or (as in the case of $C_{1-4}$-alkyl) 1 to 4 (i.e. 1, 2, 3 or 4) or (as in the case of $C_{1-3}$-alkyl) 1 to 3 (i.e. 1, 2 or 3) or (as in the case of $C_{1-2}$-alkyl) 1 or 2 C-atoms, i.e. $C_{1-18}$-, $C_{1-10}$-, $C_{1-8}$-, $C_{1-6}$-, $C_{1-4}$-, $C_{1-3}$- and $C_{1-2}$-alkanyls, $C_{2-18}$-, $C_{2-12}$-, $C_{2-10}$-, $C_{2-8}$-, $C_{2-6}$-, $C_{2-4}$-, $C_{2-3}$- and $C_2$-alkenyls and $C_{2-18}$-, $C_{2-12}$-, $C_{2-10}$-, $C_{2-8}$-, $C_{2-6}$-, $C_{2-4}$-, $C_{2-3}$- and $C_2$- alkinyls. Here "alkenyls" comprise at least one C-C double bond and "alkinyls" at least one C-C triple bond. Alkyl is advantageously selected from the group comprising methyl, ethyl, n-propyl, 2-propyl, n-butyl, iso-butyl, sec-butyl, tert-butyl, n-pentyl, iso-pentyl, neo-pentyl, n-hexyl, 2-hexyl, n-heptyl, n-octyl, n-nonyl, n-decyl, n-dodecyl; ethenyl (vinyl), ethinyl, propenyl ($-CH_2CH=CH_2$, $-CH=CH-CH_3$, $-C(=CH_2)-CH_3$), propinyl ($-CH_2-C\equiv CH$, $-C\equiv C-CH_3$), butenyl, butinyl, pentenyl, pentinyl, hexenyl, hexinyl, octenyl and octinyl.

According to this invention, "$C_{3-10}$-cycloalkyl" and "$C_{3-8}$-cycloalkyl" (and "cycloalkyl") represent cyclic saturated or unsaturated hydrocarbon radicals with 3, 4, 5, 6, 7, 8, 9 or 10 and 3, 4, 5, 6, 7 or 8 C-atoms, wherein any radical can be unsubstituted or singly substituted or multiply identically or differently substituted and optionally benzocondensed. It may also refer to a bi-, tri- or polycyclic ring system. By way of example cycloalkyl represents cyclopropyl, cyclobutyl, cyclopentyl, cyclohexyl, cycloheptanyl and cyclooctanyl and adamantyl and bicyclo[3.1.1]heptan-3-yl.

For the purpose of the present invention, the term "aryl" is taken to mean a radical selected from the group comprising phenyl, naphthyl, phenanthrenyl, anthracenyl and biphenyl, and which is unsubstituted or singly or multiply identically or differently substituted. Aryl is preferably an unsubstituted or singly substituted or multiply identically or differently substituted phenyl, 1-naphthyl or 2-naphthyl.

The term "heterocyclyl" represents a monocyclic or polycyclic organic radical in which at least one cyclus contains at least 1 heteroatom or 2, 3, 4 or 5 identical or different heteroatoms selected from the group comprising N, O and S, wherein the radical is saturated or unsaturated and unsubstituted or singly substituted or multiply identically or differently substituted. Examples of heterocyclyl radicals according to the invention are monocyclic five, six or seven membered organic radicals with one heteroatom or 2, 3, 4 or 5 identical or different heteroatoms, which are nitrogen, oxygen and/or sulfur, and the known benzocondensed analogues thereof. The "heteroaryl" radicals, which are heterocyclyls in which the at least one cyclus contained in the heteroatom, is heteroaromatic, is a subgroup of the heterocyclyl radicals. Each heteroaryl radical can be unsubstituted or singly substituted or multiply identically or differently substituted. Examples of heterocyclyl radicals according to the present invention are pyrrolidinyl, tetrahydrofuryl, 1,4-dioxanyl, piperidinyl, piperazinyl and in particular morpholinyl. Examples of heteroaryl radicals are pyrrolyl, furanyl, thienyl, pyrazolyl, imidazolyl, pyridazinyl, pyrimidinyl, pyrazinyl, isoxazolyl, thieno[2,3-d]pyrimidinyl, indolyl and pyridinyl and their benzocondensed analogues. All of these radicals can be respectively unsubstituted or substituted.

For the purpose of the present invention, the terms "($C_{1-12}$-alkyl)-$C_{3-10}$-cycloalkyl", "($C_{1-16}$-alkyl)-$C_{3-10}$-cycloalkyl", "($C_{1-4}$-alkyl)-$C_{3-10}$-cycloalkyl", "($C_{1-3}$-alkyl)-$C_{3-10}$-cycloalkyl", "($C_{1-12}$-alkyl) heterocyclyl", "($C_{1-6}$-alkyl)-heterocyclyl", "($C_{1-4}$-alkyl)-heterocyclyl", "($C_{1-3}$-alkyl)-heterocyclyl", "($C_{1-12}$-alkyl)-aryl", "($C_{1-6}$-alkyl)-aryl", "($C_{1-4}$-alkyl)-aryl" and "($C_{1-3}$-alkyl)-aryl" mean that the cycloalkyl, heterocyclyl and aryl radical is bound via a $C_{1-12}$-, $C_{1-6}$-, $C_{1-4}$-, or $C_{1-13}$- group to the compound substituted by it. A particularly preferred example of "alkyl-cycloalkyl" is the cyclopropylmethyl radical.

In conjunction with "alkyl", "alkanyl", "alkenyl", "alkinyl" and "cycloalkyl", the term "substituted", according to this invention, is taken to mean —provided the term is not defined somewhere else in the description or in the claims— the single or multiple substitution of one or more hydrogen atoms by, for example, F, Cl, Br, I, —CN, $NH_2$, NH-alkyl, NH-aryl, NH-alkyl-aryl, NH-heterocyclyl, $N(alkyl)_2$, $N(alkyl-aryl)_2$, N-alkyl-N-aryl, $NO_2$, OH, O-alkyl, S-alkyl, O-aryl, O-alkyl-aryl, O-alkyl-O-alkyl, $C(=O)C_{1-6}$-alkyl, $C(=O)$aryl, $C(=O)C_{1-6}$-alkyl-aryl, $C(=O)$-heterocyclyl, $CO_2H$, $CO_2$-alkyl, $CO_2$-alkyl-aryl, $C(=O)NH_2$, $C(=O)NH$-alkyl, $C(=O)NH$-aryl, $C(=O)NH$-heterocyclyl, $C(=O)N(alkyl)_2$, $C(=O)N(alkyl-aryl)_2$, cycloalkyl, aryl or heterocyclyl, wherein the multiple substitution is made either on different or on the same atoms multiply, for example doubly or triply, for example triply on the same carbon atom as in the case of $CF_3$ or $-CH_2CF_3$ or at different positions as in the case of $-CH(OH)-CH=CCl-CH_2Cl$. Multiple substitution can be effected with the same or with different substituents. $CF_3$ is particularly preferred as a substituted alkyl for the purpose of the present invention.

With respect to "aryl", "heterocyclyl" and "heteroaryl", according to the invention "substituted" is taken to mean single or multiple, for example double, triple or quadruple, substitution of one or more hydrogen atoms of the ring system by a suitable substituent. Provided the meaning of this suitable substituent in conjunction with "aryl", "heterocyclyl" or "heteroaryl" is not defined elsewhere in the description or in the claims, suitable substituents are F, Cl, Br, I, —CN, $NH_2$, NH-alkyl, NH-aryl, NH-alkyl-aryl, NH-heterocyclyl, $N(alkyl)_2$, $N(alkyl-aryl)_2$, $NO_2$, SH, S-alkyl, OH, O-alkyl, O-cycloalkyl, O-aryl, O-alkyl-aryl, O-heterocyclyl, CHO, $C(=O)C_{1-6}$-alkyl, $C(=O)$aryl, $C(=O)-C_{1-6}$-alkyl-aryl, $CO_2H$, $CO_2$-alkyl, $CO_2$-alkyl-aryl, $C(=O)NH_2$, $C(=O)NH$-alkyl, $C(=O)NH$aryl, $C(=O)NH$-heterocyclyl, $C(=O)N(alkyl)_2$, $SO_2NH_2$, $SO_3H$, $CF_3$, $CHF_2$, $CH_2F$, $OCF_3$, $OCHF_2$, $OCH_2F$, $SCF_3$, $SCHF_2$, $SCH_2F$; alkyl, cycloalkyl, aryl and/or heterocyclyl; on one or optionally various atoms (wherein a substituent can optionally be substituted in turn). Multiple substitution is made here with the same or with different substituents. Particularly preferred substituents for aryl and heterocyclyl are $C_{1-6}$-alkyl, F, Cl, Br, I, $CF_3$, Oalkyl, $OCF_3$, phenyl, CN and/or $NO_2$.

For the purpose of the present invention, "benzocondensed" means that a benzene ring is fused to another cyclus.

Pharmaceutically acceptable or physiologically acceptable salts according to this invention are salts of the compounds according to the invention of general formula (I) which are physiologically acceptable in pharmaceutical use, in particular when used on mammals and/or humans, i.e. do not cause any (acute) fundamental impairment of the physiological functions of the respective species. Pharmaceutically acceptable (physiologically acceptable) salts can, for example, be formed with inorganic or organic acids or, if the compounds according to the invention are acids, in particular carboxylic acids, with bases.

The pharmaceutically acceptable salts of the compounds according to the invention of general formula (I) are preferably formed with hydrochloric acid, hydrobromic acid, sulfuric acid, phosphoric acid, methane sulfonic acid, p-toluene sulfonic acid, carbon dioxide, formic acid, acetic acid, oxalic acid, succinic acid, tartaric acid, mandelic acid, fumaric acid, lactic acid, citric acid, glutamic acid or aspartic acid. If the compounds according to the invention are acids, for example carboxylic acids, the pharmaceutically acceptable salts can also be formed by reaction with bases, such as sodium hydroxide, sodium hydrogen carbonate or sodium carbonate. The salts formed are inter alia hydrochlorides, hydrobromides, phosphates, carbonates, hydrogen carbonates, formiates, acetates, oxalates, succinates, tartrates, fumarates, citrates and glutaminates and sodium salts. The hydrates of the compounds according to the invention, which can be obtained, for example, by crystallization from aqueous solution, are also preferred.

Provided compounds according to the invention of formula (I) contain at least one asymmetric center they can be present in the form of their racemates, in the form of the pure enantiomers and/or (in the case of a plurality of asymmetric centers) of the diastereomers or in the form of blends of these enantiomers or diastereomers and, more precisely, both in substance and as physiologically acceptable salts of these compounds. The mixtures can be present in any mixing ratio of the stereoisomers. The compounds of general structure (I) are preferably present as enantiomer-pure compounds.

Preferred compounds according to the invention of general formula (I) are those which are characterized in that $R^1$ and $R^2$ independently of one another represent H, $C_{1-8}$-alkyl, $C_{3-8}$-cycloalkyl, ($C_{1-4}$-alkyl)-$C_{3-8}$-cycloalkyl, aryl, ($C_{1-4}$-alkyl)-aryl, heterocyclyl, ($C_{1-4}$-alkyl)-heterocyclyl or NH—C(=O)-aryl, wherein at least one of the radicals $R^1$ and $R^2$ does not represent H, or together represent —($CR^4R^5$)$_m$—($CR^6R^7$)$_n$—Y—($CR^8R^9$)$_p$—($CR^{10}R^{11}$)$_q$— where m=1, n=0 or 1, p=1 or 2 and q=1 or 2, or —$CH_2$—$CH_2$—C (-aryl)=CH—$CH_2$;

$R^3$ represents $SO_2R^{12}$ or $COR^{13}$;

$R^4$, $R^5$, $R^6$, $R^7$, $R^8$, $R^9$, $R^{10}$ and $R^{11}$ independently of one another represent H, $C_{1-8}$-alkyl or C(=O)$R^{14}$;

Y represents $CR^{15}R^{16}$ or $NR^{17}$;

$R^{12}$ represents $C_{1-4}$-alkyl, ($C_{1-4}$-alkyl)-$C_{3-8}$-cycloalkyl, aryl, ($C_{1-4}$-alkyl)-aryl, heterocyclyl or $NR^{18}R^{19}$;

$R^{13}$ represents $C_{1-6}$-alkyl, $C_{3-10}$-cycloalkyl, aryl, ($C_{1-4}$-alkyl)-aryl or heterocyclyl;

$R^{14}$ represents $OR^{20}$;

$R^{15}$ and $R^{16}$ independently of one another represent H, aryl or ($C_{1-4}$-alkyl)-aryl;

$R^{17}$ represents H, $C_{3-8}$-cycloalkyl, aryl, ($C_{1-4}$-alkyl)-aryl, heterocyclyl or C(=O)$R^{22}$;

$R^{18}$ and $R^{19}$ independently of one another represent H or $C_{1-6}$-alkyl;

$R^{20}$ represents $C_{1-6}$-alkyl;

$R^{22}$ represents aryl, ($C_{1-4}$-alkyl)-aryl, heterocyclyl or $OR^{24}$; and $R^{24}$ represents $C_{1-6}$-alkyl or ($C_{1-4}$-alkyl)-aryl.

A particularly preferred sub-group of these preferred compounds of formula (I) is formed by compounds in which $R^1$ represents $C_{1-6}$-alkyl, $C_{3-8}$-cycloalkyl, ($C_{1-3}$-alkyl)-$C_{3-8}$-cycloalkyl, aryl, ($C_{1-3}$-alkyl)-aryl, heterocyclyl, ($C_{1-3}$-alkyl-)heterocyclyl or NH—C(=O)-aryl; and $R^2$ represents H, $C_{1-4}$-alkyl, ($C_{1-3}$-alkyl)-aryl or ($C_{1-3}$-alkyl)-heterocyclyl, wherein more particularly preferred compounds are those in which $R^1$ represents methyl, ethyl, n-propyl, iso-propyl, 2-methylpropyl, n-butyl, tert.-butyl, n-phenyl, 3-methylbutyl or $CH_2$—C($CH_3$)=$CH_2$, in particular methyl, ethyl, $CH_2$—C($CH_3$)=$CH_2$, CH(C(=O)O$CH_2$=$CH_2$)—$CH_2$C(=O)O-tert.-butyl, 2-cyanoethyl, $CH_2$—$CH_2$—NH—C(=O)$CH_3$, 2-(N-ethyl-N-(3-methylphenyl)amino)-ethyl, 2-(N,N-dimethylamino)-ethyl, 2-(C(=O)—NH—(β-naphthyl)-ethyl, 1,2-(di(C(=O)O-tert.-butyl)ethyl, 3-(N-methyl-N-phenylamino)-propyl, 1-(C(=O)O-benzyl)-3-methyl-butyl, 1-(C(=O)O-butyl)-3-methyl-butyl, $CH_2CO_2$ethyl, $CH_2$—$CH_2CO_2$ethyl, $CH_2$–$CH_2$-Ophenyl, $CH_2$—$CH_2$—S—$CH_2$—$CH_3$, unsubstituted or substituted by F, Cl, Br, I, —CN, N-alkyl-N-arylamine, N,N-dialkylamine, amide, carboxyalkyl, carboxybenzyl;

cyclopropyl, cyclobutyl, cyclopentyl, cyclohexyl, cycloheptyl, cyclooctyl, bicyclo[3.1.1]heptan-3-yl, in particular 2-phenylcyclopropyl, 2-(O-benzyl)-cyclopentyl, 2-(carboxyethyl)cyclohexyl, 7,7-dimethyl-2-methylbicyclo[3.1.1]-heptan-3-yl; cyclopropylmethyl, 7,7-dimethyl-2-oxo-bicyclo[2.2.1]hept-1-ylmethyl, unsubstituted or substituted by F, Cl, Br, I, —CN, alkyl, aryl, carboxyalkyl, carboxybenzyl, O-alkyl, O-benzyl;

phenyl, 1-naphthyl or 2-naphthyl, unsubstituted or substituted by phenoxy, —$CH_2$P(=O)(Oethyl)$_2$;

$CH_2$-aryl, $CH_2$—$CH_2$-aryl, $CH_2$—$CH_2$—$CH_2$-aryl, $CH_2$—$CH_2$—$CH_2$—$CH_2$-aryl CH($CH_3$)-aryl, CH($CH_3$)—$CH_2$-aryl, $CH_2$CH-(aryl)$_2$, CH($CO_2$alkyl)—$CH_2$-aryl, $CH_2$—$CH_2$—CH-(aryl)$_2$, wherein aryl is unsubstituted phenyl, 1-naphthyl or 2-naphthyl or phenyl, in particular benzyl, —$CH_2$-naphth-1-yl, 2-fluorobenzyl, 3-fluorobenzyl, 3-chlorobenzyl, 3-methoxybenzyl, 2-ethoxybenzyl, 2,4-difluorobenzyl, 3,5-dichlorobenzyl, 3-fluoro-5-trifluoromethylbenzyl, 3-fluoro-4-trifluoromethylbenzyl, 2-chloro-6-fluorobenzyl, 2,5-dimethoxybenzyl, 2-chloro-6-methyl-benzyl, 3,4-dimethoxybenzyl, 3,4-dioxymethylenebenzyl, CH($CH_3$)phenyl, CH($CH_3$)-(4-$CH_3$-phenyl), CH($CH_3$)-(4nitrophenyl), CH($CH_3$)-(2,3-dioxyethylenephenyl), $CH_2CH_2$-phenyl, $CH_2$—$CH_2$-(2-fluorophenyl), $CH_2$-$CH_2$-(3-fluorophenyl), $CH_2$—$CH_2$-(4-fluorophenyl), $CH_2$-$CH_2$-(4-chlorophenyl), $CH_2$-$CH_2$-(3,4-dichlorophenyl), $CH_2$—$CH_2$(3-methoxyphenyl), $CH_2$—$CH_2$-(2,5-dimethoxyphenyl), CH($CO_2$-tert.-butyl)- $CH_2$-phenyl, CH($CO_2$-methyl)-$CH_2$(4-chlorophenyl), $CH_2$-CH(phenyl)$_2$, CH($CH_3$)—$CH_2$-(4-chlorophenyl), $CH_2$—$CH_2$—CH(phenyl)$_2$, $CH_2$—$CH_2$—$CH_2$-phenyl, substituted by F, Cl, Br, I, —CN, —$NO_2$, alkyl, $CF_3$, alkoxy, alkylene dioxy;

pyrrolidine or piperidine, in particular pyrrolidin-3-yl, N-(4-trifluorobenzyl)pyrrolidin-3-yl, N-(3-methoxy-benzyl)-pyrrolidin-3-yl, N-(CH$_2$-(β-naphthyl)-pyrrolidin-3-yl or N-(carboxyethyl)-piperidin-4-yl, unsubstituted or substituted by aryl, alkylaryl or carboxyethyl;

(CH$_2$)$_{1-3}$-heterocyclyl, unsubstituted or substituted by alkyl, F, Cl, Br, I, —CN, aryl, alkylaryl, wherein heterocyclyl represents furanyl, benzofuranyl, 1,4-dioxanyl, benzo-1,4-dioxanyl, thienyl, pyridinyl, pyrrolidinyl, 1H-indolyl, imidazolyl, piperidinyl, tetrahydrofuranyl, in particular CH$_2$-furan-2-yl, 5-methylfuran-2-yl CH$_2$-benzofuran-2-yl,

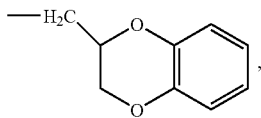

CH$_2$-thien-2-yl, CH$_2$-pyridin-3-yl, CH$_2$-pyridin-4-yl, CH$_2$CH$_2$-pyridin-2-yl, CH$_2$—CH$_2$-(1H-indol-3-yl), CH$_2$—CH$_2$-pyrrolidin-1-yl, CH$_2$-(N-2,6-dichlorobenzyl-pyrrolidin-3-yl), CH$_2$—CH$_2$-(N-methyl-pyrrolidin-2-yl), —(CH2)3-imidazol-1-yl, CH$_2$-(tetrahydrofuran-2-yl) or

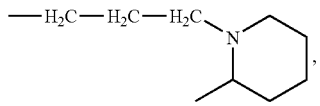

or CH(CO$_2$ methyl)-CH$_2$-(1H-indol-3-yl); NH—C(=O)-(4-diethylaminophenyl); and R$^2$ represents H;
methyl, ethyl or CH$_2$—C(CH$_3$)=CH$_2$, in particular methyl, ethyl, 2-cyanoethyl, CH$_2$—C(CH$_3$)=CH$_2$, unsubstituted or substituted by F, Cl, Br, I, —CN;
benzyl or phenethyl, in particular benzyl, 4-fluorobenzyl, 2-chloro-6-fluorobenzyl, 2,5-dimethoxybenzyl, phenethyl, unsubstituted or substituted by F, Cl, Br, I, —CN, methoxy, ethoxy; or CH$_2$-furanyl, in particular CH$_2$-furan-2-yl, CH$_2$-benzofuranyl, in particular CH$_2$-benzofuran-2-yl, CH$_2$-pyridinyl, in particular CH$_2$-pyridin-3-yl, CH$_2$-tetrahydrofuranyl, in particular CH$_2$-tetrahydrofuran-2-yl, CH$_2$—CH$_2$-pyridinyl, in particular CH$_2$—CH$_2$-pyridin-2-yl.

A further group of preferred compounds according to the invention of formula (I) is formed by those which are characterized in that R$^1$ and R$^2$ together represent

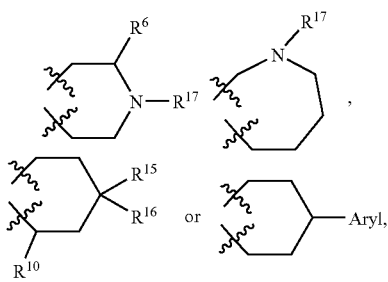

wherein aryl represents phenyl, or phenyl, in particular 4-fluorophenyl, substituted by F, Cl, Br, I;

R$^6$ represents H or C$_{1-4}$ alkyl, in particular methyl;
R$^{10}$ represents H, C(=O)Omethyl, C(=O)Oethyl, C(=O)O-n-propyl, C(=O)O-iso-propyl, C(=O)O-n-butyl, C(=O)O-tert.-butyl;
R$^{15}$ represents H or CH$_2$-aryl;
R$^{16}$ represents H;
R$^{17}$ represents H;
C$_{3-8}$-cycloalkyl, in particular cycloheptyl;
aryl, in particular phenyl or naphthyl, unsubstituted or substituted by methyl, ethyl, n-propyl, iso-propyl, n-butyl, tert.-butyl, CF$_3$, F, Cl, Br, I, —CN, methoxy, ethoxy, n-propoxy, isopropoxy, n-butoxy, tert.-butoxy;
((CH$_2$)$_{1-3}$-alkyl)-aryl or CH(CH$_3$)-aryl, wherein aryl represents phenyl or naphthyl, unsubstituted or substituted by alkyl, CF$_3$, F, Cl, Br, I, —CN, alkoxy;
pyridinyl, pyrazinyl or thieno[2,3-d]pyrimidinyl, unsubstituted or substituted by alkyl, CF$_3$, F, Cl, Br, I, —CN, alkoxy; or
C(=O)R$^{22}$; and
R$^{22}$ represents phenyl or alkoxy-substituted phenyl, O-methyl, O-ethyl, O-n-propyl, O-iso-propyl, O-n-butyl, O-tert.butyl, O-benzyl, unsubstituted benzyl, benzyl substituted by F, unsubstituted pyrazinyl or pyrazinyl substituted by alkyl;

wherein the more particularly preferred of these compounds are those in which
R$^6$ represents H or methyl;
R$^{10}$ represents H or C(=O)Oethyl;
R$^{15}$ represents H or benzyl;
R$^{16}$ represents H; and
R$^{17}$ represents H;
cycloheptyl;
phenyl, 2-methylphenyl, 3-methylphenyl, 2,4-dimethylphenyl, 2-ethylphenyl, 3-trifluoromethyl, 4-fluorophenyl, 4-chlorophenyl, 2-methoxyphenyl, 3,5-dimethoxyphenyl, 3-chloro-6-methylphenyl;
benzyl, CH$_2$-(4-tert.-butylphenyl), CH$_2$-(β-naphthyl), CH(CH$_3$)-phenyl, (CH$_2$)$_3$-phenyl;
pyridin-2-yl, (4-trifluoromethyl)-pyridin-2-yl, thieno[2,3-d]pyrimidin-4-yl;
or
C(=O)-(4-methoxyphenyl), C(=O)-benzyl, C(=O)—CH$_2$-(3,4-difluorophenyl),
C(=O)-(2-methylpyrazin-5-yl), C(=O)O-tert.-butyl or O-benzyl.

It is also preferred, when R$^3$ represents SO$_2$R$^{12}$ in the compounds according to the invention of general formula (I), if
R$^{12}$ represents methyl, ethyl, n-propyl, iso-propyl, in particular n-propyl;
7,7-dimethyl-2-oxo-bicyclo [2.2.1]hept- 1-ylmethyl;
phenyl, or phenyl, in particular 4-methylphenyl, 3-trifluoromethylphenyl, 4-fluorophenyl, 2-chlorophenyl, 3-chlorophenyl, 4-chlorophenyl, 4-methoxyphenyl, 4-trifluoromethoxyphenyl, 4-nitrophenyl, 2-CO$_2$-methyl-phenyl, 2,5-dichlorophenyl, 3-fluoro-6-methylphenyl, 3-bromo-6-methoxyphenyl, 2-methyl- 5-nitrophenyl, 2,4,6-trimethylphenyl substituted by methyl, ethyl, n-propyl, iso-propyl, n-butyl, tert.-butyl, CF$_3$, F, Cl, Br, I, —CN, NO$_2$, methoxy, ethoxy, n-propoxy, iso-propoxy, n-butoxy, tert.-butoxy, OCF$_3$, CO$_2$-methyl; benzyl or benzyl substituted by methyl, ethyl, n-propyl, iso-propyl, n-butyl, tert.-butyl, CF$_3$, F, Cl, Br, I, —CN, NO$_2$, methoxy, ethoxy, n-propoxy, iso-propoxy, n-butoxy, tert.-butoxy, OCF$_3$; furanyl or thienyl, in particular thien-2-yl, 5-chlorothien-2-yl, unsubstituted or substituted by methyl, ethyl, n-propyl, iso-propyl, n-butyl, tert.-butyl, CF$_3$, F, Cl, Br, I, —CN, NO$_2$, methoxy, ethoxy, n-propoxy, iso-propoxy, n-butoxy, tert.-butoxy; or NR$^{13}$R$^{19}$; and R$^{18}$ and R$^{19}$ independently of one another represent H, methyl or ethyl.

It is also preferred, when R$^3$ represents COR$^{13}$ in the compounds according to the invention of general formula (I), if R$^{13}$ represents methyl, ethyl, C(=O)Omethyl, n-propyl, isopropyl, 2-methylpropyl, n-butyl, tert.-butyl, n-pentyl or 3-methylbutyl, in particular methyl, ethyl, n-propyl, n-butyl, tert.-butyl, n-pentyl, CH$_2$—O—CH$_2$—CH$_2$—OCH$_3$, CH(CH$_3$)-O-phenyl, CH$_2$—CH$_2$—C(=O)OCH$_3$, C(CH$_3$)$_2$—OC(=O)CH$_3$, CH$_2$—O-benzyl, CH$_2$—O—(3-chlorophenyl), CH$_2$—CH$_2$—CH$_2$—O-phenyl, CH(OC(=O)methyl)CH$_3$; cyclopropyl, 2-phenylcyclopropyl, 1-adamantyl, unsubstituted or substituted by O-methyl, O-ethyl, O—(CH$_2$)$_2$. OCH$_3$, O-benzyl, O-phenyl, wherein phenyl is unsubstituted or substituted by F, Cl, Br, I, —CN, O—C(=O)-methyl, O—C(=O)-ethyl;

phenyl or naphthyl, in particular 4-fluorophenyl, 2-chlorophenyl, 3-chlorophenyl, 4-bromophenyl, 4-phenylphenyl (4-biphenyl), 4-ethylphenyl, 4-CF$_3$-phenyl, 4methoxyphenyl, 2-ethoxyphenyl, 4-tert.-butyl, 3-OCF$_3$-phenyl, 4-OCF$_3$-phenyl, 4-SCF$_3$-phenyl, 3-SCF$_2$-phenyl, 2-CH$_2$—OC(=O)phenyl, 3-dimethylaminophenyl, 2,3-dichlorophenyl, 2,4-difluorophenyl, 3-chloro-4-fluorophenyl, 3-chloro-2-fluorophenyl, 4-CF$_3$-3-fluorophenyl, 3-CF$_3$-6-fluorophenyl, 4-bromo-3-methylphenyl, 2-chloro-4-nitrophenyl, 2,3,4,5,6-pentafluorophenyl, 2,6-difluoro-3-methylphenyl, 2,3-difluoro-4-methylphenyl, 2-chloro-5-methyl-6-fluorophenyl, 1-naphthyl, 2-naphthyl, unsubstituted or substituted by F, Cl, Br, I, —CN, phenyl, methyl, ethyl, n-propyl, iso-propyl, n-butyl, tert.-butyl, CF$_3$, F, Cl, Br, I, —CN, NO$_2$, methoxy, ethoxy, n-propoxy, iso-propoxy, n-butoxy, tert.-butoxy, OCF$_3$, OCHF$_2$, OCH$_2$F, SCF$_3$, SCHF$_2$, SCH$_2$F, SCH$_3$, CH$_2$ OC(=O)phenyl, —N(CH$_3$);

unsubstituted or substituted (C$_{1-2}$-alkyl)-aryl, in particular benzyl, phenethyl, CH(C$_2$H$_5$)-phenyl, CH(NH—SO$_2$-(4-methylphenyl))-CH$_2$-phenyl, CH=CH-phenyl, CH=CH-(3-trifluorophenyl); or unsubstituted or alkyl-substituted furanyl, benzofuranyl, or thienyl, pyridinyl, pyrazolyl, benzodihydropyranyl, isooxazolyl, in particular 1,5-dimethylfuran-3-yl, 2methyl-5-tert.-butyl-furan-3-yl, 3-chlorothien-2-yl 1-(4-chlorophenyl)-5-trifluoro-methyl-pyrazol-4-yl, 1-methyl-3-tert.-butyl-pyrazol-5-yl,

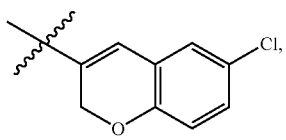

pyridin-4-yl, 2-methylthiopyridin-3-yl, 2-ethylthiopyridin-3-yl, 2-phenoxypyridin-3-yl, 2-chloropyridin-3-yl, 5-methyl-3-(2,6-dichlorophenyl)-isoxazol-4-yl, 5-methyl-3-(2-chloro-6-fluorophenyl)-isoxazol-4-yl, unsubstituted or substituted by alkyl, CF$_3$, aryl, O-phenyl, chlorine, S-methyl, S-ethyl.

Selected and particularly preferred compounds of formula (I) according to the invention are:

3-(1H-indol-3-yl)-2-{[8-(4-trifluoromethoxy-benzenesulphonyl)-1-oxa-2,8-diaza-spiro[4,5]dec-2-ene-3-carbonyl]-amino}-propionic acid methylester {4-[(8-phenylmethanesulphonyl-1-oxa-2,8-diaza-spiro[4,5]dec-2-ene-3-carbonyl)-amino]-benzyl}-phosphonic acid diethylester (4-cycloheptyl-piperazin-1-yl)-[8-(thiophene-2-sulphonyl)-1-oxa-2,8-diaza-spiro[4,5]dec-2-en-3-yl]-methanone

[8-(5-chloro-thiophene-2-sulphonyl)-1-oxa-2,8-diaza-spiro[4,5]dec-2-en-3-yl]-(4-phenyl-piperazin-1-yl)-methanone 8-(2-chloro-4-nitro-benzoyl)-1-oxa-2,8-diaza-spiro[4,5]dec-2-ene-3-carboxylic acid cyclopentylamide (4-naphthalen-2-ylmethyl-piperazin-1-yl) -(8-phenylmethanesulphonyl-1-oxa-2,8-diaza-spiro[4,5]dec-2-en-3-yl)-methanone 8-dimethylsulphamoyl-1-oxa-2,8-diaza-spiro[4,5]dec-2-ene-3-carboxylic acid phenethylamide 8-(thiophene-2-sulphonyl)-1-oxa-2,8-diaza-spiro[4,5]dec-2-ene-3-carboxylic acid (1-phenyl-ethyl) amide 8-(toluene-4-sulphonyl)-1-oxa-2,8-diaza-spiro[4,5]dec-2-ene-3-carboxylic acid [2-(3,4-dichloro-phenyl)-ethyl] amide 4-diethylamino-benzoic acid N'-[8-(thiophene-2-sulphonyl)-1-oxa-2,8-diaza-spiro[4,5]dec-2-ene-3-carbonyl]-hydrazides 8-(3-chloro-4-fluoro-benzenesulphonyl)-1-oxa-2,8-diaza-spiro[4,5]dec-2-ene-3-carboxylic acid 2-pyrrolidin-1-yl-ethyl) amide 8-phenylmethanesulphonyl-1-oxa-2,8-diaza-spiro[4,5]dec-2-ene-3-carboxylic acid phenethyl amide 8-benzenesulphonyl-1-oxa-2,8-diaza-spiro[4,5]dec-2-ene-3-carboxylic acid (2-dimethylamino-ethyl) amide

[4-(3-phenyl-propyl)-piperazin-1-yl]-[8-(thiophene-2-sulphonyl)-1-oxa-2,8-diaza-spiro[4,5]dec-2-en-3-yl]-methanone 8-(2,5-dichloro-benzenesulphonyl)-1-oxa-2,8-diaza-spiro[4,5]dec-2-ene-3-carboxylic acid [3-(2-methyl-piperidin-1-yl)-propyl] amide 8-(4-trifluoromethoxy-benzenesulphonyl)-1-oxa-2,8-diaza-spiro[4,5]dec-2-ene-3-carboxylic acid [2-(1H-indol-3-yl)-ethyl]-methyl amide 8-(5-fluoro-2-methyl-benzenesulphonyl)-1-oxa-2,8-diaza-spiro[4,5]dec-2-ene-3-carboxylic acid (2-acetylamino-ethyl) amide 8-(toluene-4-sulphonyl)-1-oxa-2,8-diaza-spiro[4,5]dec-2-ene-3-carboxylic acid benzyl-phenethyl amide 8-(2-methyl-5-nitro-benzenesulphonyl)-1-oxa-2,8-diaza-spiro[4,5]dec-2-ene-3-carboxylic acid (2-dimethylamino-ethyl) amide 8-phenylmethanesulphonyl-1-oxa-2,8-diaza-spiro[4,5]dec-2-ene-3-carboxylic acid (2-benzyloxy-cyclopentyl) amide 8-(thiophene-2-sulphonyl)-1-oxa-2,8-diaza-spiro[4,5]dec-2-ene-3-carboxylic acid (2,3-dihydro-benzo[1,4]dioxin-2-ylmethyl) amide 8-(toluene-4-sulphonyl)-1-oxa-2,8-diaza-spiro[4,5]dec-2-ene-3-carboxylic acid (4-phenoxy-phenyl) amide 8-(thiophene-2-sulphonyl)-1-oxa-2,8-diaza-spiro[4,5]dec-2-ene-3 carboxylic acid (1-p-tolyl-ethyl) amide 8-(thiophene-2-sulphonyl)-1-oxa-2,8-diaza-spiro[4,5]dec-2-ene-3-carboxylic acid 3-fluoro-benzyl amide 2-phenyl-1-{4-[8-(toluene-4-sulphonyl)-1-oxa-2,8-diaza-spiro[4,5]dec-2-ene-3-carbonyl]-piperazin-1-yl}-ethanone 8-(thiophene-2-sulphonyl)-1-oxa-2,8-diaza-spiro[4,5]dec-2-ene-3-carboxylic acid [1-(4-trifluoromethyl-benzyl)-pyrrolidin-3-yl] amide

[8-(thiophene-2-sulphonyl)-1-oxa-2,8-diaza-spiro[4,5]dec-2-en-3-yl]-(4-o-tolyl-piperazin-1-yl)-methanone 8-(toluene-4-sulphonyl)-1-oxa-2,8-diaza-spiro[4,5]dec-2-ene-3-carboxylic acid benzyl-(2-cyano-ethyl) amide

[8-(2,5-dichloro-benzenesulphonyl)-1-oxa-2,8-diaza-spiro[4,5]dec-2-en-3-yl]-(4-thieno [2,3-d]pyrimidin-4-yl-piperazin-1-yl)-methanone 8-(5-chloro-thiophene-2-sulphonyl)-1-oxa-2,8-diaza-spiro[4,5]dec-2-ene-3-carboxylic acid (benzo[1,3]dioxol-5-yl-methyl) amide (3-methyl-4-m-tolyl-piperazin-1-yl)-[8-(thiophene-2-sulphonyl)-1-oxa-2,8-diaza-spiro[4,5]dec-2-en-3-yl]-methanone

[4-(1-phenyl-ethyl)-piperazin-1-yl]-[8-(toluene-4-sulphonyl)-1-oxa-2,8-diaza-spiro[4,5]dec-2-en-3-yl]-methanone

[4-(2,4-dimethyl-phenyl)-piperazin-1-yl]-[8-(toluene-4-sulphonyl)-1-oxa-2,8-diaza-spiro[4,5]dec-2-en-3-yl]-methanone 8-(2-chloro-pyridine-3-carbonyl)-1-oxa-2,8-diaza-spiro[4,5]dec-2-ene-3-carboxylic acid cyclopentylamide (4-naphthalen-2-ylmethyl-piperazin-1-yl)-[8-(3-trifluoromethyl-benzenesulphonyl)-1-oxa-2,8-diaza-spiro[4,5]dec-2-en-3-yl]-methanone 8-[3-phenyl-2-(toluene-4-sulphonylamino)-propionyl]-1-oxa-2,8-diaza-spiro[4,5]dec-2-ene-3-carboxylic acid (pyridin-3-ylmethyl) amide 8-(5-fluoro-2-methyl-benzenesulphonyl)-1-oxa-2,8-diaza-spiro[4,5]dec-2-ene-3-carboxylic acid (2-dimethylamino-ethyl) amide 8-(4-nitro-benzenesulphonyl)-1-oxa-2,8-diaza-spiro[4,5]dec-2-ene-3-carboxylic acid (thiophen-2-ylmethyl) amide 8-(2,5-dichloro-benzenesulphonyl)-1-oxa-2,8-diaza-spiro[4, 5]dec-2-ene-3-carboxylic acid 3-fluoro-5-trifluoromethyl-benzyl amide 8-(5-chloro-thiophene-2-sulphonyl)-1-oxa-2,8-diaza-spiro[4,5]dec-2-ene-3-carboxylic acid benzhydryl amide 8-[3-phenyl-2-(toluene-4-sulphonylamino)-propionyl]-1-oxa-2,8-diaza-spiro[4,5]dec-2-ene-3-carboxylic acid (2-cyano-ethyl) amide

[(8-phenylmethanesulphonyl-1-oxa-2,8-diaza-spiro[4,5]dec-2-ene-3-carbonyl)-amino]-ethyl acetate 8-(3-dimethylamino-benzoyl)-1-oxa-2,8-diaza-spiro[4,5]dec-2-ene-3-carboxylic acid (2-cyano-ethyl) amide 8-(2,5-dichloro-benzenesulphonyl)-1-oxa-2,8-diaza-spiro[4,5]dec-2-ene-3-carboxylic acid [1-(naphthalen-2-yl-carbamoyl)-ethyl] amide 8-(toluene-4-sulphonyl)-1-oxa-2,8-diaza-spiro[4,5]dec-2-ene-3-carboxylic acid (1-p-tolyl-ethyl) amide

[4-(4-chloro-phenyl)-piperazin-1-yl]-(8-phenylmethanesulphonyl-1-oxa-2,8-diaza-spiro[4,5]dec-2-en-3-yl)-methanone 8-(thiophene-2-sulphonyl)-1-oxa-2,8-diaza-spiro[4,5]dec-2-ene-3-carboxylic acid (2-benzyloxy-cyclopentyl) amide 8-acetyl-1-oxa-2,8-diaza-spiro[4,5]dec-2-ene-3-carboxylic acid benzyl amide 8-(5-chloro-thiophene-2-sulphonyl)-1-oxa-2,8-diaza-spiro[4,5]dec-2-ene-3-carboxylic acid 2,5-difluoro-benzyl amide 8-(5-chloro-thiophene-2-sulphonyl)-1-oxa-2,8-diaza-spiro[4,5]dec-2-ene-3-carboxylic acid (1-naphthalen-2-ylmethyl-pyrrolidin-3-yl) amide 8-phenylmethanesulphonyl-1-oxa-2,8-diaza-spiro[4,5]dec-2-ene-3-carboxylic acid 2-ethoxy-benzyl amide 8-(4-ethyl-benzoyl)-1-oxa-2,8-diaza-spiro[4,5]dec-2-ene-3-carboxylic acid (thiophen-2-ylmethyl) amide 2-{[8-(2,5-dichloro-benzenesulphonyl)-1-oxa-2,8-diaza-spiro[4,5]dec-2-ene-3-carbonyl]-amino}-succinic acid 1-allylester-4-tert-butylester 8-(4-trifluoromethoxy-benzenesulphonyl)-1-oxa-2,8-diaza-spiro[4,5]dec-2-ene-3-carboxylic acid naphthalen-2-ylamide 4-{[8-(2-phenyl-cyclopropanecarbonyl)-1-oxa-2,8-diaza-spiro[4,5]dec-2-ene-3-carbonyl]-amino}-piperidine-1-carboxylic acid ethylester 4-{[8-(2,4-difluoro-benzoyl)-1-oxa-2,8-diaza-spiro[4,5]dec-2-ene-3-carbonyl]-amino}-piperidine-1-carboxylic acid ethylester 8-(toluene-4-sulphonyl)-1-oxa-2,8-diaza-spiro[4,5]dec-2-ene-3-carboxylic acid (2-dimethylamino-ethyl) amide 8-dimethylsulphamoyl-1-oxa-2,8-diaza-spiro[4,5]dec-2-ene-3-carboxylic acid [2-(4-chloro-phenyl)-ethyl] amide 8-(4-methoxy-benzoyl)-1-oxa-2,8-diaza-spiro[4,5]dec-2-ene-3-carboxylic acid (5-methyl-furan-2-ylmethyl) amide 8-(thiophene-2-sulphonyl)-1-oxa-2,8-diaza-spiro[4,5]dec-2-ene-3-carboxylic acid [2-(4-chloro-phenyl)-ethyl] amide 8-(5-chloro-thiophene-2-sulphonyl)-1-oxa-2,8-diaza-spiro[4,5]dec-2-ene-3-carboxylic acid [2-(1-methyl-pyrrolidin-2-yl)-ethyl] amide 4-{[8-(4-bromo-benzoyl)-1-oxa-2,8-diaza-spiro[4,5]dec-2-ene-3-carbonyl]-amino}-piperidine-1-carboxylic acid ethylester 8-(toluene-4-sulphonyl)-1-oxa-2,8-diaza-spiro[4,5]dec-2-ene-3-carboxylic acid 3,5-dichloro-benzyl amide 8-(2,5-dichloro-benzenesulphonyl)-1-oxa-2,8-diaza-spiro[4,5]dec-2-ene-3-carboxylic acid [1-(3-methoxy-benzyl)-pyrrolidin-3-yl] amide 3-(4-naphthalen-2-ylmethyl-piperazine-1-carbonyl)-1-oxa-2,8-diaza-spiro[4,5]dec-2-ene-8-sulphonic acid dimethylamide 3-{[8-(7,7-dimethyl-2-oxo-bicyclo [2.2.1]hept-1-yl-methanesulphonyl)-1-oxa-2,8-diaza-spiro[4,5]dec-2-ene-3-carbonyl]-amino}propionic acid ethylester 8-(toluene-4-sulphonyl)-1-oxa-2,8-diaza-spiro[4,5]dec-2-ene-3-carboxylic acid (2-benzyloxy-cyclopentyl) amide 8-(2,5-dichloro-benzenesulphonyl)-1-oxa-2,8-diaza-spiro[4,5]dec-2-ene-3-carboxylic acid 3,4-dimethoxy-benzyl amide (8-phenylmethanesulphonyl-1-oxa-2,8-diaza-spiro[4,5]dec-2-en-3-yl)-[4(3-phenyl-propyl)-piperazin-1-yl]-methanone 3-(4-thieno [2,3-d]pyrimidin-4-yl-piperazine-1-carbonyl)-1-oxa-2,8-diaza-spiro[4,5]dec-2-ene-8-sulphonic acid dimethylamide

[8-(5-chloro-thiophene-2-sulphonyl)-1-oxa-2,8-diaza-spiro[4,5]dec-2-en-3-yl]-[4- (3,5-dimethoxy-phenyl)-piperazin-1-yl]-methanone 8-dimethylsulphamoyl-1-oxa-2,8-diaza-spiro[4,5]dec-2-ene-3-carboxylic acid 3-fluoro-4-trifluoromethyl-benzyl amide 8-(toluene-4-sulphonyl)-1-oxa-2,8-diaza-spiro[4,5]dec-2-ene-3-carboxylic acid (2-benzyloxy-cyclopentyl) amide 4-[(8-Butyryl-1-oxa-2,8-diaza-spiro[4,5]dec-2-ene-3-carbonyl)-amino]-piperidine-1-carboxylic acid ethylester 8-(toluene-4-sulphonyl)-1-oxa-2,8-diaza-spiro[4,5]dec-2-ene-3-carboxylic acid (2-phenyl-cyclopropyl) amide

[8-(4-fluoro-benzenesulphonyl)-1-oxa-2,8-diaza-spiro[4,5]dec-2-en-3-yl]-[4 5-methyl-pyrazine-2-carbonyl)-piperazin-1-yl]-methanone 8-dimethylsulphamoyl-1-oxa-2,8-diaza-spiro[4,5]dec-2-ene-3-carboxylic acid 2,4-difluoro-benzyl amide 8-phenylmethanesulphonyl-1-oxa-2,8-diaza-spiro[4,5]dec-2-ene-3-arboxylic acid [2-(3-fluoro-phenyl)-ethyl] amide 8-(5-chloro-thiophene-2-sulphonyl)-1-oxa-2,8-diaza-spiro[4,5]dec-2-ene-3-carboxylic acid (2,2-diphenyl-ethyl) amide 3-[4-(3-phenyl-propyl)-piperazine-1-carbonyl]-1-oxa-2,8-diaza-piro[4,5]dec-2-ene-8-sulphonic acid dimethylamide 3-{[8-(3,5-difluoro-benzoyl)-1-oxa-2,8-diaza-spiro[4,5]dec-2-ene-3-carbonyl]-amino}-propionic acid ethyl ester 8-(propane-1-sulphonyl)-1-oxa-2,8-diaza-spiro[4,5]dec-2-ene-3-carboxylic cid isobutyl amide

[4-(3-phenyl-propyl)-piperazin-1-yl]-[8-(3-trifluoromethyl-enzenesulphonyl) 1-oxa-2,8-diaza-spiro[4,5]dec-2-en-3-yl]-methanone 8-(thiophene-2-sulphonyl)-1-oxa-2,8-diaza-spiro[4,5]dec-2-ene-3-carboxylic cid [1-(2,3-dihydro-benzo[1,4]dioxin-5-yl)-ethyl] amide 8-butyryl-1-oxa-2,8-diaza-spiro[4,5]dec-2-ene-3-carboxylic acid henylamide 8-(4-trifluoromethoxy-benzenesulphonyl)-1-oxa-2,8-diaza-spiro[4,5]dec-2-ene-3-carboxylic acid cyclooctylamide 8-[2-(2-methoxy-ethoxy)-acetyl]-1-oxa-2,8-diaza-spiro[4,5]dec-2-ene-3-carboxylic acid benzyl amide 8-(4-bromo-3-methyl-benzoyl)-1-oxa-2,8-diaza-spiro[4,5]dec-2-ene-3-carboxylic acid isobutyl amide 8-(5-chloro-thiophene-2-sulphonyl)-1-oxa-2,8-diaza-spiro[4,5]dec-2-ene-3-carboxylic acid [3-(methyl-phenyl-amino)-propyl] amide 4-{[8-(2-methyl-5-nitro-benzenesulphonyl)-1-oxa-2,8-diaza-spiro[4,5]dec-2-ene-3-carbonyl]-amino}-piperidine-1-carboxylic acid ethylester

[8-(5-chloro-thiophene-2-sulphonyl)-1-oxa-2,8-diaza-spiro[4,5]dec-2-en-3-yl]-[4-(4-fluoro-phenyl)-piperazin-1-yl]-methanone 8-(2,5-dichloro-benzenesulphonyl)-1-oxa-2,8-diaza-spiro[4,5]dec-2-ene-3-carboxylic acid methyl-pyridin-3-ylmethyl amide 2-(3,4-difluoro-phenyl)-1-{4-[8-(3-trifluoromethyl-benzenesulphonyl)-1-oxa-2,8-diaza-spiro[4,5]dec-2-ene-3-carbonyl]-piperazin-1-yl}-ethanone 8-(3-trifluoromethyl-benzenesulphonyl)-1-oxa-2,8-diaza-spiro[4,5]dec-2-ene-3-carboxylic acid cyclopropylmethyl amide 3-{[8-(2-methyl-5-nitro-benzenesulphonyl)-1-oxa-2,8-diaza-spiro[4,5]dec-2-ene-3-carbonyl]-amino}-propionic acid ethylester 8-[2-(3-chloro-phenoxy)-acetyl]-1-oxa-2,8-diaza-spiro[4,5]dec-2-ene-3-carboxylic acid (thiophen-2-ylmethyl) amide 8-(4-trifluoromethoxy-benzenesulphonyl)-1-oxa-2,8-diaza-spiro[4,5]dec-2-ene-3-carboxylic acid benzyl-phenethyl amide 8-(2,5-dichloro-benzenesulphonyl)-1-oxa-2,8-diaza-spiro[4,5]dec-2-ene-3-carboxylic acid benzyl-phenethyl amide 8-(2,5-dichloro-benzenesulphonyl)-1-oxa-2,8-diaza-spiro[4,5]dec-2-ene-3-carboxylic acid (2-cyano-ethyl)-pyridin-3-ylmethyl amide 8-(2,5-dichloro-benzenesulphonyl)-1-oxa-2,8-diaza-spiro[4,5]dec-2-ene-3-carboxylic acid (2-cyano-ethyl)-(tetrahydrofuran-2-ylmethyl) amide 8-(3-trifluoromethyl-benzenesulphonyl)-1-oxa-2,8-diaza-spiro[4,5]dec-2-ene-3-carboxylic acid methyl-pyridin-3-ylmethyl amide 8-(pyridine-4-carbonyl)-1-oxa-2,8-diaza-spiro[4,5]dec-2-ene-3-carboxylic acid benzyl amide 8-(4-trifluoromethoxy-benzenesulphonyl)-1-oxa-2,8-diaza-spiro[4,5]dec-2-ene-3-carboxylic acid ethyl-(2-methyl-allyl) amide 8-(4-methoxy-benzenesulphonyl)-1-oxa-2,8-diaza-spiro[4,5]dec-2-ene-3-carboxylic acid [2-(2-fluoro-phenyl)-ethyl] amide 8-(5-tert-butyl-2-methyl-furan-3-carbonyl)-1-oxa-2,8-diaza-spiro[4,5]dec-2-ene-3-carboxylic acid isobutyl amide 8-(3-phenyl-acryloyl)-1-oxa-2,8-diaza-spiro[4,5]dec-2-ene-3-carboxylic acid (thiophen-2-ylmethyl) amide 8-(4-trifluoromethyl-benzoyl)-1-oxa-2,8-diaza-spiro[4,5]dec-2-ene-3-carboxylic acid cyclopropylmethyl amide 8-(4-trifluoromethylsulphanyl-benzoyl)-1-oxa-2,8-diaza-spiro[4,5]dec-2-ene-3-carboxylic acid cyclopropylmethyl amide 8-(4-bromo-benzoyl)-1-oxa-2,8-diaza-spiro[4,5]dec-2-ene-3-carboxylic acid (5-methyl-furan-2-ylmethyl) amide 8-(3-fluoro-4-trifluoromethyl-benzoyl)-1-oxa-2,8-diaza-spiro[4,5]dec-2-ene-3-carboxylic acid cyclopropylmethyl amide 8-(7,7-dimethyl-2-oxo-bicyclo [2.2.1]hept-1-ylmethanesulphonyl)-1-oxa-2,8-diaza-spiro[4,5]dec-2-ene-3-carboxylic acid (2-ethylsulphanyl-ethyl) amide 8-(2,4-difluoro-benzoyl)-1-oxa-2,8-diaza-spiro[4,5]dec-2-ene-3-carboxylic acid (tetrahydrofuran-2-ylmethyl) amide {[8-(3-chloro-thiophene-2-carbonyl)-1-oxa-2,8-diaza-spiro[4,5]dec-2-ene-3-carbonyl]-amino}-acetic acid ethylester 4-oxo-4-{3-[(thiophen-2-ylmethyl)-carbamoyl]-1-oxa-2,8-diaza-spiro[4,5]dec-2-ene-8-yl}-butyric acid methylester 8-(2-ethylsulphanyl-pyridine-3-carbonyl)-1-oxa-2,8-diaza-spiro[4,5]dec-2-ene-3-carboxylic acid benzyl amide 3-{[8-(2-chloro-benzenesulphonyl)-1-oxa-2,8-diaza-spiro[4,5]dec-2-ene-3-carbonyl]-amino}-propionic acid ethylester 8-(4-trifluoromethoxy-benzoyl)-1-oxa-2,8-diaza-spiro[4,5]dec-2-ene-3-carboxylic acid cyclopropylmethyl amide 8-(4-phenoxy-butyryl)-1-oxa-2,8-diaza-spiro[4,5]dec-2-ene-3-carboxylic acid cyclopropylmethyl amide

[8-(3-trifluoromethyl-benzenesulphonyl)-1-oxa-2,8-diaza-spiro[4,5]dec-2-en-3-yl]-[4-(4-trifluoromethyl-pyridin-2-yl)-piperazin-1-yl]-methanone 8-(2-chloro-5-trifluoromethyl-benzoyl)-1-oxa-2,8-diaza-spiro[4,5]dec-2-ene-3-carboxylic acid cyclopropylmethyl amide 8-(4-methoxy-benzenesulphonyl)-1-oxa-2,8-diaza-spiro [4,5]dec-2-ene-3-carboxylic acid (2-benzyloxy-cyclopentyl) amide
4-{[8-(3-trifluoromethyl-benzenesulphonyl)-1-oxa-2,8-diaza-spiro[4,5]dec-2-ene-3-carbonyl]-amino}-piperidine-1-carboxylic acid ethylester
8-(2-phenoxy-propionyl)-1-oxa-2,8-diaza-spiro[4,5]dec-2-ene-3-carboxylic acid cyclopropylmethyl amide
8-(4-fluoro-benzenesulphonyl)-1-oxa-2,8-diaza-spiro[4,5]dec-2-ene-3-carboxylic acid [2-(3-methoxy-phenyl)-ethyl] amide
8-(2-methylsulphanyl-pyridine-3-carbonyl)-1-oxa-2,8-diaza-spiro[4,5]dec-2-ene-3-carboxylic acid isobutyl amide
8-(5-tert-butyl-2-methyl-furan-3-carbonyl)-1-oxa-2,8-diaza-spiro[4,5]dec-2-ene-3-carboxylic acid cyclopentyl amide
8-(4-chloro-benzenesulphonyl)-1-oxa-2,8-diaza-spiro[4,5]dec-2-ene-3-carboxylic acid (thiophen-2-ylmethyl) amide
8-(5-chloro-thiophene-2-sulphonyl)-1-oxa-2,8-diaza-spiro[4,5]dec-2-ene-3-carboxylic acid (naphthalen-1-ylmethyl) amide
8-(4-trifluoromethoxy-benzenesulphonyl)-1-oxa-2,8-diaza-spiro[4,5]dec-2-ene-3-carboxylic acid [2-(4-fluoro-phenyl)-ethyl] amide
8-(4-bromo-3-methyl-benzoyl)-1-oxa-2,8-diaza-spiro[4,5]dec-2-ene-3-carboxylic acid (pyridin-4-ylmethyl) amide
8-(4-methoxy-benzoyl)-1-oxa-2,8-diaza-spiro[4,5]dec-2-ene-3-carboxylic acid benzyl amide
8-(3-trifluoromethyl-benzenesulphonyl)-1-oxa-2,8-diaza-spiro[4,5]dec-2-ene-3-carboxylic acid 3-chloro-benzyl amide
(8-phenylmethanesulphonyl-1-oxa-2,8-diaza-spiro[4,5]dec-2-en-3-yl)-(4-o-tolyl-piperazin-1-yl)-methanone
(8-phenylmethanesulphonyl-1-oxa-2,8-diaza-spiro[4,5]dec-2-en-3-yl)-(4-2-yl-piperazin-1-yl))-methanone
8-(4-trifluoromethylsulphanyl-benzoyl)-1-oxa-2,8-diaza-spiro[4,5]dec-2-ene-3-carboxylic acid (thiophen-2-ylmethyl) amide
8-(thiophene-2-sulphonyl)-1-oxa-2,8-diaza-spiro[4,5]dec-2-ene-3-carboxylic acid benzyl amide
8-(4-fluoro-benzoyl)-1-oxa-2,8-diaza-spiro[4,5]dec-2-ene-3-carboxylic acid isobutyl amide
2-(3-isobutylcarbamoyl-1-oxa-2,8-diaza-spiro[4,5]dec-2-ene-8-sulphonyl) benzoic acid methylester
2-[(8-dimethylsulphamoyl-1-oxa-2,8-diaza-spiro[4,5]dec-2-ene-3-carbonyl) amino]-3-phenyl-propionic acid tert-butylester
8-(5-chloro-thiophene-2-sulphonyl)-1-oxa-2,8-diaza-spiro[4,5]dec-2-ene-3-carboxylic acid [1-(2,3-dihydro-benzo[1,4]dioxin-5-yl)-ethyl] amide
8-(4-bromo-benzoyl)-1-oxa-2,8-diaza-spiro[4,5]dec-2-ene-3-carboxylic acid (thiophen-2-ylmethyl) amide
8-(4-fluoro-benzenesulphonyl)-1-oxa-2,8-diaza-spiro[4,5]dec-2-ene-3-carboxylic acid (3-imidazol-1-yl-propyl) amide
4-[8-(4-fluoro-benzenesulphonyl)-1-oxa-2,8-diaza-spiro[4,5]dec-2-ene-3-carbonyl]-piperazine-1-carboxylic acid benzylester
3-(4-cycloheptyl-piperazine-1-carbonyl)-1-oxa-2,8-diaza-spiro[4,5]dec-2-ene-8-sulphonic acid dimethylamide
4-methyl-2-{[8-(thiophene-2-sulphonyl)-1-oxa-2,8-diaza-spiro[4,5]dec-2-ene-3-carbonyl]-amino}-pentanoic acid tert-butylester
8-(3-chloro-2-fluoro-benzoyl)-1-oxa-2,8-diaza-spiro[4,5] dec-2-ene-3-carboxylic acid (thiophen-2-ylmethyl) amide
2-{[8-(4-methoxy-benzenesulphonyl)-1-oxa-2,8-diaza-spiro[4,5]dec-2-ene-3-carbonyl]-amino}-4-methyl-pentanoic acid tert-butylester
3-{[8-(6-chloro-2-fluoro-3-methyl-benzoyl)-1-oxa-2,8-diaza-spiro[4,5]dec-2-ene-3- carbonyl]-amino}-propionic acid ethylester
8-(2-phenoxy-propionyl)-1-oxa-2,8-diaza-spiro[4,5]dec-2-ene-3-carboxylic acid benzyl amide
8-(5-fluoro-2-methyl-benzenesulphonyl)-1-oxa-2,8-diaza-spiro[4,5]dec-2-ene-3-carboxylic acid (thiophen-2-ylmethyl) amide
[8-(5-chloro-thiophene-2-sulphonyl)-1-oxa-2,8-diaza-spiro[4,5]dec-2-en-3-yl]-[4-(2-methoxy-phenyl)-piperidin-1-yl]-methanone
8-(2-chloro-benzoyl)-1-oxa-2,8-diaza-spiro[4,5]dec-2-ene-3-carboxylic acid (thiophen-2-ylmethyl) amide
8-(2-phenoxy-pyridine-3-carbonyl)-1-oxa-2,8-diaza-spiro[4,5]dec-2-ene-3-carboxylic acid cyclopentylamide
8-(4-bromo-benzoyl)-1-oxa-2,8-diaza-spiro[4,5]dec-2-ene-3-carboxylic acid (2-ethylsulphanyl-ethyl) amide
1-[8-(5-chloro-thiophene-2-sulphonyl)-1-oxa-2,8-diaza-spiro[4,5]dec-2-ene-3-carbonyl]-piperidin-2-carboxylic acid ethylester
8-(2-chloro-benzenesulphonyl)-1-oxa-2,8-diaza-spiro[4,5]dec-2-ene-3-carboxylic acid (thiophen-2-ylmethyl) amide
8-(2,3-dichloro-benzoyl)-1-oxa-2,8-diaza-spiro[4,5]dec-2-ene-3-carboxylic acid cyclopropylmethyl amide
8-hexanoyl-1-oxa-2,8-diaza-spiro[4,5]dec-2-ene-3-carboxylic acid cyclopropylmethyl amide
8-(2,3-difluoro-4-methyl-benzoyl)-1-oxa-2,8-diaza-spiro [4,5]dec-2-ene-3-carboxylic acid cyclopropylmethyl amide
8-(4-fluoro-benzenesulphonyl)-1-oxa-2,8-diaza-spiro[4,5]dec-2-ene-3-carboxylic acid (2,5-dimethoxy-benzyl)-furan-2-ylmethyl amide
8-dimethylsulphamoyl-1-oxa-2,8-diaza-spiro[4,5]dec-2-ene-3-carboxylic acid (2-ethylsulphanyl-ethyl) amide
8-(4-trifluoromethoxy-benzenesulphonyl)-1-oxa-2,8-diaza-spiro[4,5]dec-2-ene-3-carboxylic acid 3-methoxy-benzyl amide
8-dimethylsulphamoyl-1-oxa-2,8-diaza-spiro[4,5]dec-2-ene-3-carboxylic acid (2-benzyloxy-cyclopentyl) amide
8-(4-methoxy-benzenesulphonyl)-1-oxa-2,8-diaza-spiro [4,5]dec-2-ene-3-carboxylic acid [2-(4-chloro-phenyl)-1-methyl-ethyl] amide
8-(4-trifluoromethoxy-benzenesulphonyl)-1-oxa-2,8-diaza-spiro[4,5]dec-2-ene-3-carboxylic acid [2-(3,4-dichloro-phenyl)-ethyl] amide
8-[2-(3-chloro-phenoxy)-acetyl]-1-oxa-2,8-diaza-spiro[4,5]dec-2-ene-3-carboxylic acid benzyl amide
8-(4-fluoro-benzenesulphonyl)-1-oxa-2,8-diaza-spiro [4,5]dec-2-ene-3-carboxylic acid (2-cyano-ethyl)-(2-pyridin-2-yl-ethyl) amide
8-(5-chloro-thiophene-2-sulphonyl)-1-oxa-2,8-diaza-spiro[4,5]dec-2-ene-3-carboxylic acid [2-(4-chloro-phenyl)-1-methyl-ethyl] amide
8-(4-methoxy-benzenesulphonyl)-1-oxa-2,8-diaza-spiro [4,5]dec-2-ene-3-carboxylic acid (2-benzyloxy-cyclopentyl) amide
8-(2,6-difluoro-3-methyl-benzoyl)-1-oxa-2,8-diaza-spiro [4,5]dec-2-ene-3-carboxylic acid (thiophen-2-ylmethyl) amide 8-(2-benzyloxy-acetyl)-1-oxa-2,8-diaza-spiro[4,5]dec-2-ene-3-carboxylic acid benzyl amide
8-(2,3-dichloro-benzoyl)-1-oxa-2,8-diaza-spiro[4,5]dec-2-ene-3-carboxylic acid phenylamide
8-(5-bromo-2-methoxy-benzenesulphonyl)-1-oxa-2,8-diaza-spiro[4,5]dec-2-ene-3-carboxylic acid cyclopentylamide
acetic acid 2-(3-benzylcarbamoyl-1-oxa-2,8-diaza-spiro[4,5]dec-2-en-8-yl)-1,1-dimethyl-2-oxo-ethylester
8-[3-(2-chloro-6-fluoro-phenyl)-5-methyl-isoxazole-4-carbonyl]-1-oxa-2,8-diaza-spiro[4,5]dec-2-ene-3-carboxylic acid (2-ethylsulphanyl-ethyl) amide
[4-(3-phenyl-propyl)-piperazin-1-yl]-[8-(4-trifluoromethoxy-benzenesulphonyl)-1-oxa-2,8-diaza-spiro[4,5]dec-2-en-3-yl]-methanone
8-[3-(2-chloro-6-fluoro-phenyl)-5-methyl-isoxazole-4-carbonyl]-1-oxa-2,8-diaza-spiro[4,5]dec-2-ene-3-carboxylic acid benzyl amide
8-(naphthalene carbonyl)-1-oxa-2,8-diaza-spiro[4,5]dec-2-ene-3-carboxylic acid isobutyl amide
1-[8-(5-tert-butyl-2-methyl-furan-3-carbonyl)-1-oxa-2,8-diaza-spiro[4,5]dec-2-ene-3-carbonyl]-piperidin-2-carboxylic acid ethylester
8-(3-difluoromethylsulphanyl-benzoyl)-1-oxa-2,8-diaza-spiro[4,5]dec-2-ene-3-carboxylic acid benzyl amide
8-(4-bromo-benzoyl)-1-oxa-2,8-diaza-spiro[4,5]dec-2-ene-3-carboxylic acid phenylamide
8-(4-methoxy-benzenesulphonyl)-1-oxa-2,8-diaza-spiro[4,5]dec-2-ene-3-carboxylic acid (2-phenyl-cyclopropyl) amide
8-(4-phenoxy-butyryl)-1-oxa-2,8-diaza-spiro[4,5]dec-2-ene-3-carboxylic acid (thiophen-2-ylmethyl) amide
8-(3-chloro-4-fluoro-benzoyl)-1-oxa-2,8-diaza-spiro[4,5]dec-2-ene-3-carboxylic acid (thiophen-2-ylmethyl) amide
8-(5-tert-butyl-2-methyl-2H-pyrazole-3-carbonyl)-1-oxa-2,8-diaza-spiro[4,5]dec-2-ene-3-carboxylic acid (2-ethylsulphanyl-ethyl) amide
[8-(4-fluoro-benzenesulphonyl)-1-oxa-2,8-diaza-spiro[4,5]dec-2-en-3-yl]-[4(3-phenyl-propyl)-piperazin-1-yl]-methanone
8-(4-trifluoromethoxy-benzoyl)-1-oxa-2,8-diaza-spiro[4,5]dec-2-ene-3-carboxylic acid (pyridin-4-ylmethyl) amide
benzoic acid 2-(3-cyclopentylcarbamoyl-1-oxa-2,8-diaza-spiro[4,5]dec-2-ene-8-carbonyl)-benzyl ester
3-[4-(4-tert-butyl-benzyl)-piperazine-1-carbonyl]-1-oxa-2,8-diaza-spiro[4,5]dec-2-ene-8-sulphonic acid dimethylamide
{[8-(2-ethoxy-benzoyl)-1-oxa-2,8-diaza-spiro[4,5]dec-2-ene-3-carbonyl]-amino}-acetic acid ethylester
8-(5-chloro-thiophene-2-sulphonyl)-1-oxa-2,8-diaza-spiro[4,5]dec-2-ene-3-carboxylic acid (2-benzyloxy-cyclopentyl) amide
8-(naphthalene-1-carbonyl)-1-oxa-2,8-diaza-spiro[4,5]dec-2-ene-3-carboxylic acid (thiophen-2-ylmethyl) amide
8-(4-fluoro-benzenesulphonyl)-1-oxa-2,8-diaza-spiro[4,5]dec-2-ene-3-carboxylic acid (3-phenyl-propyl) amide
8-(5-chloro-thiophene-2-sulphonyl)-1-oxa-2,8-diaza-spiro[4,5]dec-2-ene-3-carboxylic acid (2,3-dihydro-benzo[1,4]dioxin-2-ylmethyl) amide
1-[8-(4-tert-butyl-benzoyl)-1-oxa-2,8-diaza-spiro[4,5]dec-2-ene-3-carbonyl]-piperidine-2-carboxylic acid ethyl ester
8-(4-fluoro-benzenesulphonyl)-1-oxa-2,8-diaza-spiro[4,5]dec-2-ene-3-carboxylic acid [2-(3-trifluoromethyl-phenyl)-ethyl] amide
8-[3-(2,6-dichloro-phenyl)-5-methyl-isoxazole-4-carbonyl]-1-oxa-2,8-diaza-spiro[4,5]dec-2-ene-3-carboxylic acid (thiophen-2-ylmethyl) amide
8-(4-fluoro-benzenesulphonyl)-1-oxa-2,8-diaza-spiro[4,5]dec-2-ene-3-carboxylic acid [1-(naphthalen-2-ylcarbamoyl)-ethyl] amide
8-(4-fluoro-benzenesulphonyl)-1-oxa-2,8-diaza-spiro[4,5]dec2-ene-3-carboxylic acid (2-benzyloxy-cyclopentyl) amide
3-(4-chloro-phenyl)-2-{[8-(4-methoxy-benzenesulphonyl)-1-oxa-2,8-diaza-spiro[4,5]dec-2-ene-3-carbonyl]-amino}-propionic acid methyl ester
8-(3-trifluoromethyl-benzenesulphonyl)-1-oxa-2,8-diaza-spiro[4,5]dec-2-ene-3-carboxylic acid (2-benzyloxy-cyclopentyl) amide
8-(3-trifluoromethyl-benzenesulphonyl)-1-oxa-2,8-diaza-spiro[4,5]dec-2-ene-3-carboxylic acid (2-phenoxy-ethyl) amide
8-(2-phenoxy-pyridine-3-carbonyl)-1-oxa-2,8-diaza-spiro[4,5]dec-2-ene-3-carboxylic acid benzyl amide
8-(naphthalene-2-carbonyl)-1-oxa-2,8-diaza-spiro[4,5]dec-2-ene-3-carboxylic acid cyclopropylmethyl amide
8-(3-chloro-4-fluoro-benzoyl)-1-oxa-2,8-diaza-spiro[4,5]dec-2-ene-3-carboxylic acid benzyl amide
8-(2-phenyl-butyryl)-1-oxa-2,8-diaza-spiro[4,5]dec-2-ene-3-carboxylic acid (2-cyano-ethyl) amide
8-(4-fluoro-benzenesulphonyl)-1-oxa-2,8-diaza-spiro[4,5]dec-2-ene-3-carboxylic acid 2-fluoro-benzyl amide
8-(3-chloro-benzoyl)-1-oxa-2,8-diaza-spiro[4,5]dec-2-ene-3-carboxylic acid (thiophen-2-ylmethyl) amide
(4-benzyl-piperazin-1-yl)-[8-(2,5-dichloro-benzenesulphonyl)-1-oxa-2,8-diaza-spiro[4,5]dec-2-en-3-yl]-methanone
8-(3-chloro-benzenesulphonyl)-1-oxa-2,8-diaza-spiro[4,5]dec-2-ene-3-carboxylic acid benzyl amide
(4-benzyl-piperidin-1-yl)-[8-(3-trifluoromethyl-benzenesulphonyl)-1-oxa-2,8-diaza-spiro[4,5]dec-2-en-3-yl]-methanone
8-(4-bromo-benzoyl)-1-oxa-2,8-diaza-spiro[4,5]dec-2-ene-3-carboxylic acid benzyl amide
8-(4-fluoro-benzenesulphonyl)-1-oxa-2,8-diaza-spiro[4,5]dec-2-ene-3-carboxylic acid [1-(4-nitro-phenyl)-ethyl] amide
4-methyl-2-{[8-(3-trifluoromethyl-benzenesulphonyl)-1-oxa-2,8-diaza-spiro[4,5]dec-2-ene-3-carbonyl]-amino)-pentanoic acid tert.-butyl ester
[4-(4-fluoro-phenyl)-3,6-dihydro-2H-pyridin-1-yl]-(8-phenylmethanesulphonyl-1-oxa-2,8-diaza-spiro[4,5]dec-2-en-3-yl) methanone
8-dimethylsulphamoyl-1-oxa-2,8-diaza-spiro[4,5]dec-2-ene-3-carboxylic acid [2-(ethyl-m-tolyl-amino)-ethyl] amide
8-(2,5-dimethyl-furan-3-carbonyl)-1-oxa-2,8-diaza-spiro[4,5]dec-2-ene-3-carboxylic acid benzyl amide
(4-cycloheptyl-piperazin-1-yl)-[8-(4-fluoro-benzenesulphonyl)-1-oxa-2,8-diaza-spiro[4,5]dec-2-en-3-yl]-methanone
8-(2-benzyloxy-acetyl)-1-oxa-2,8-diaza-spiro[4,5]dec-2-ene-3-carboxylic acid benzyl amide
R,R-8-(5-chloro-thiophene-2-sulphonyl)-1-oxa-2,8-diaza-spiro[4,5]dec-2-ene-3-carboxylic acid (2-benzyloxy-cyclopentyl) amide and the hydrochlorides thereof.

The present invention also relates to a process for producing 1-oxa-2,8-diaza-spiro[4,5]dec-2-ene derivatives according to the invention of general formula (I). This process is characterized in that (a) the compound of formula (II)

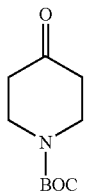

II which is commercially available or easily accessible from piperidin-4-one and a BOC cyclization agent, is reacted with a methylating agent, preferably $Ph_3PCH_3Br$ in the presence of potassium-tert.-butylate in THF, to form compound (III)

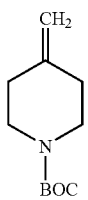

III (b) compound (III) is subjected to a reaction with ethyl-chloroximidoacetate (IV)

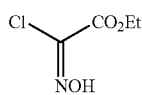

IV in the presence of a base, preferably sodium hydrogen carbonate or lithium hydroxide, preferably in an organic solvent, in particular methanol, dichloromethane or THF to form the 1-oxa-2,8-diaza-spiro[4,5]dec-2-ene derivative of formula (V);

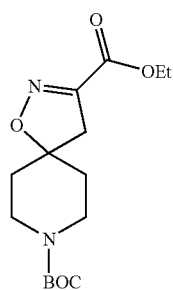

V (c) compound (V) is reacted either directly or after previous saponification of the carboxylic acid ethylester function of compound (V) and optionally with activation of the carboxylic acid function thus formed with an amine of formula $HNR^1R^2$, wherein $R^1$ and $R^2$ are defined as in any of claims 1 to 8, to form the 1-oxa-2,8-diaza-spiro[4,5]dec-2-ene derivative of formula (VI);

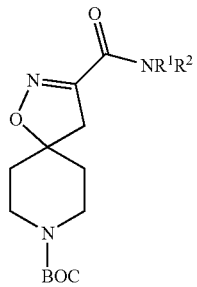

VI (d) by removing the BOC protective group from compound (VI), compound (I) where $R^3$=H

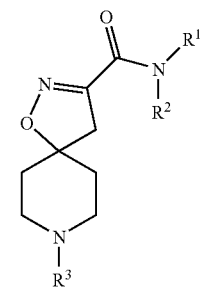

is obtained; and (e) optionally compound (I) where $R^3$=H is converted with an acid chloride of formula $R^{12}SO_2Cl$ into a compound (I) where $R^3$=$SO_2R^{12}$, wherein $R^{12}$ is as defined in any of claims 1 to 8, or with a carboxylic acid chloride of formula $R^{13}COCl$ into a compound (I) where $R^3$=$COR^{13}$, wherein $R^{13}$ is as defined in any of claims 1 to 8.

Here, the BOC protective group (BOC=tert.-butyloxycarbonyl) is introduced before step (a) and the formation of the exo-methylene group in step (a) and the 1,3-dipolar cycloaddition in step (b) of the process according to the invention analogously to an instruction known from the literature according to WO 97/33887, pages 78 to 82, the entirety of which is hereby incorporated by reference. The following reaction steps (c), (d) and optionally (e)—proceeding from the spiroester (V) with amide formation by reaction with a primary or secondary amine ((c)) (optionally after previous splitting of the ethylester and optionally with activation of the free carboxylic acid function, for example with dicyclohexylcarbodiimide (DCC), 1-hydroxylbenzotriazole and triethylamine or N-methylmorpholine and castro reagent (BOP reagent) in, for example, DMF), removal of the BOC protective group from amide (VI) ((d)) and optionally reaction with acid chlorides or sulphonic acid chlorides ((e)), —are carried out using the methods generally known to the person skilled in the art, as indicated, for example, in "Peptide Chemistry", M. Bodansky, Springer-Verlag, 1993, which is incorporated by reference herein. The following reaction sequence summarizes the synthesis sequence according to the invention.

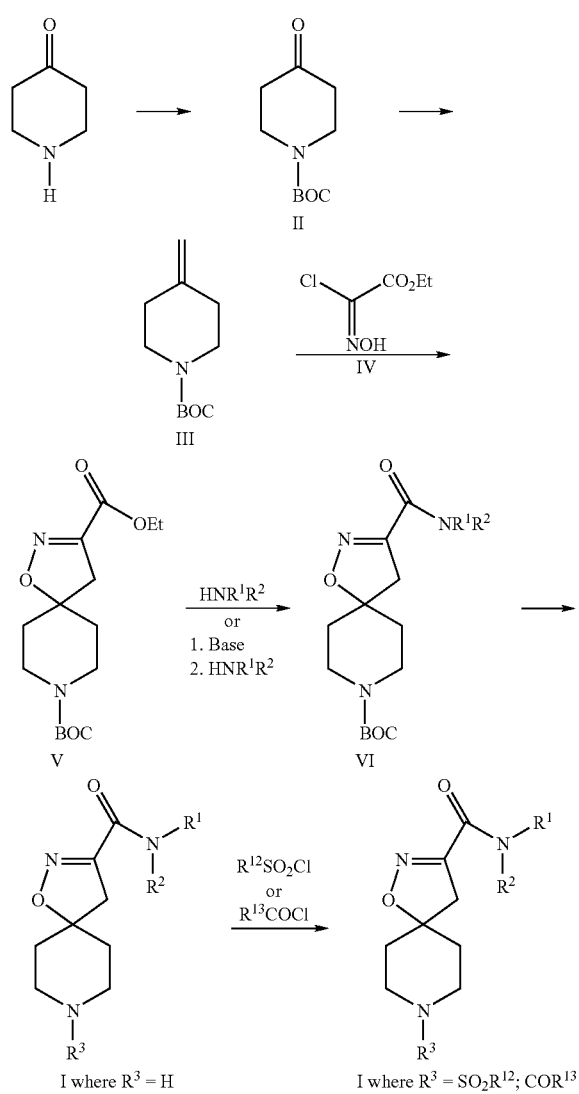

The compounds used in the process according to the invention and the reagents, if not commercially available, may be obtained by processes known to the person skilled in the art, from the state of the art.

The 1-oxa-2,8-diaza-spiro[4,5]dec-2-ene derivatives according to the invention are toxicologically harmless, so they are suitable as pharmaceutically active ingredients in pharmaceutical preparations.

The subject of the invention therefore also relates to a pharmaceutical composition containing at least one substituted 1-oxa-2,8-diaza-spiro[4,5]dec-2-ene derivative of general formula (I) as described above in the form of its racemates, its pure stereoisomers, in particular enantiomers or diastereomers, or in the form of blends of stereoisomers, in particular the enantiomers or diastereomers, in any mixing ratio; in the illustrated form or in the form of its acids or its bases or in the form of its salts, in particular the physiologically acceptable salts, more particularly preferably in the form of its solvates, in particular the hydrates.

The pharmaceutical compositions according to the invention can be administered as liquid pharmaceutical compositions in the form of injection solutions, drops or syrups, as semi-solid pharmaceutical compositions in the form of granules, tablets, pellets, patches, capsules, plasters or aerosols and contain, in addition to at least one substituted 1-oxa-2,8-diaza-spiro[4,5]dec-2-ene derivative according to the invention of formula I, optionally excipients, fillers, solvents, diluents, dyes and/or binders, depending on the galenic form. The choice of auxiliary agents and the quantities thereof to be used depend on whether the pharmaceutical composition is to be applied orally, perorally, parenterally, intravenously, intraperitoneally, intradermally, intramuscularly, intranasally, buccally, rectally or topically, for example to infections of the skin, the mucus membranes or the eyes. Preparations in the form of tablets, dragees, capsules, granules, drops and syrups are suitable for oral application, and solutions, suspensions, easily reconstitutable dry preparations and sprays are suitable for parenteral, topical and inhalative applications. 1-oxa-2,8-diaza-spiro[4,5]dec-2-ene derivatives according to the invention in a deposit, in dissolved form or in a plaster, optionally with the addition of agents promoting skin penetration, are suitable percutaneous application preparations. Orally or percutaneously applicable forms of preparation can release the substituted C-cyclohexylmethylamine derivatives according to the invention after a delay. The quantity of active ingredient to be administered to the patient varies as a function of the weight of the patient, the method of application, the indication and the severity of the disease. Conventionally, 2 to 500 mg/kg of at least one 1-oxa-2,8-diaza-spiro[4,5]dec-2-ene derivative according to the invention are applied.

The 1-oxa-2,8-diaza-spiro[4,5]dec-2-ene derivatives according to the invention are used to treat pain, in particular neuropathic pain and/or chronic pain, but also for migraines, so the invention also relates to the use of at least one 1-oxa-2,8-diaza-spiro[4,5]dec-2-ene derivative according to formula I also in the form its racemates; enantiomers or diastereomers, in particular blends of its enantiomers or diastereomers or of an individual enantiomer or diastereomers; its bases and/or salts of physiologically acceptable acids, in particular of the hydrochloride salt, to produce a pharmaceutical composition to treat pain, in particular neuropathic pain and/or chronic pain and/or to treat and/or prevent migraines.

It has surprisingly been found that the 1-oxa-2,8-diaza-spiro[4,5]dec-2-ene derivatives of general formula I are also very suitable for treating urinary incontinence, irritation, Tinnitus aurium and/or diarrhea. The application therefore also relates to the use of at least one 1-oxa-2,8-diaza-spiro[4,5] dec-2-ene derivative according to formula I also in the form its racemates; enantiomers or diastereomers, in particular blends of its enantiomers or diastereomers or of an individual enantiomer or diastereomers; its bases and/or salts of physiologically acceptable acids, in particular of the hydrochloride salt, to produce a pharmaceutical composition to treat and/or prevent urinary incontinence, irritation, Tinnitus aurium and/or diarrhea.

Further therapeutic fields of application result from the affinity to the BTX binding site, so the 1-oxa-2,8-diaza-spiro [4,5]dec-2-ene derivatives of general formula I are used in the form of their racemates, their pure stereoisomers, in particular enantiomers or diastereomers, or in the form of blends of stereoisomers, in particular the enantiomers or diastereomers, in any mixing ratio; in the illustrated form or in the form of their acids or their bases or in the form of their salts, in particular the physiologically acceptable salts, more particularly preferably in the form of their solvates, in particular the hydrates; for producing a pharmaceutical composition for anaesthesia, in particular local anaesthesia, and/or to treat and/or prevent arrhythmia and/or emesis and/or cardiovascular diseases and/or cerebral ischemia and/or alcohol dependency and/or drug dependency and/or medicine dependency and/or inflammations and/or vertigo and/or as a nootropivum (neurotropivum) and/or a muscle relaxant.

Further therapeutic fields of application result from the affinity to the NMDA receptor as NMDA antagonists have inter alia a neuroprotective effect, as is known, and therefore can also be effectively used for symptoms accompanying neurodegeneration and damage such as Parkinson's disease and Huntington's chorea, etc. Further indications of the NMDA antagonists according to the invention are epilepsy, glaucoma, osteoporosis, ototoxicity, withdrawal symptoms accompanying alcohol and/or drug abuse, strokes, and cerebral ischemia connected therewith, cerebral infarcts, brain oedema, hypoxy, anoxy, and use for anxiolysis and in anaesthesia. The invention therefore also relates to the use of at least one 1-oxa-2,8-diaza-spiro[4,5]dec-2-ene derivative according to formula (I) also in the form of its racemates; enantiomers, diastereomers, in particular blends of its enantiomers or diastereomers or of an individual enantiomer or diastereomers; its bases and/or salts of physiologically acceptable acids, in particular of the hydrochloride salt, to produce a pharmaceutical composition to treat/prevent pain in cases of epilepsy, Parkinson's disease, Huntington's chorea, glaucoma, ototoxicity, withdrawal symptoms in cases of alcohol and/or drug abuse, strokes, cerebral ischemia, cerebral infarcts, brain oedema, hypoxy, anoxy, and/or for anxiolysis and/or anaesthesia.

Compounds according to the invention of formula (I) also effectively bind to the $\alpha_{2\delta}$-receptor and have proven themselves as NA-uptake/5HT-uptake inhibitors. Therefore the invention also relates to the use of a substituted 1-oxa-2,8-diaza-spiro[4,5]dec-2-ene derivative according to formula (I) also in the form of its racemates, its pure stereoisomers, in particular enantiomers or diastereomers, or in the form of blends of stereoisomers, in particular the enantiomers or diastereomers, in any mixing ratio; in the illustrated form or in the form of its acids or its bases or in the form of its salts, in particular the physiologically acceptable salts, more particularly preferably in the form of its hydrochlorides or in the form of its solvates, in particular the hydrates to produce a pharmaceutical composition to treat and/or prevent inflammatory and/or allergic reactions and/or gastritis and/or ulcers and/or depression and/or states of shock and/or narcolepsy and/or epilepsy and/or excess weight and/or asthma and/or glaucoma and/or hyperkinetic syndrome; lack of drive and/or bulimia and/or anorexia and/or catalepsy and/or for anxiolysis and/or for increasing alertness and/or libido; bipolar disturbances and/or postmenopausal hot flashes and/or amyotropic lateral sclerosis (ALS) and/or reflex-sympathetic dystrophy (RSD) and/or spastic paralysis and/or restless leg syndrome and/or acquired nystagmus and/or multiple sclerosis and/or Parkinson's disease and/or Alzheimer's disease and/or Huntington's chorea.

The invention also relates to a process for treating a non-human mammal or a human requiring treatment of medically-relevant symptoms by administering a therapeutically effective dose of a substituted 1-oxa-2,8-diaza-spiro[4,5]dec-2-ene derivative according to formula (I) also in the form of its racemates, its pure stereoisomers, in particular enantiomers or diastereomers, or in the form of blends of stereoisomers, in particular the enantiomers or diastereomers, in any mixing ratio; in the illustrated form or in the form of its acids or its bases or in the form of its salts, in particular the physiologically acceptable salts, more particularly preferably in the form of its hydrochlorides or in the form of its solvates, in particular the hydrates; or of a pharmaceutical composition according to the invention. The invention relates in particular to a corresponding process for treating pain, in particular neuropathic pain and/or chronic pain and/or migraines and/or urinary incontinence and/or irritation and/or Tinnitus aurium and/or diarrhea and/or arrhythmia and/or emesis and/or cardiovascular diseases and/or cerebral ischemia and/or alcohol dependency and/or drug dependency and/or medicine dependency and/or inflammations and/or vertigo and/or inflammatory reactions and/or allergic reactions and/or gastritis and/or ulcers and/or depression and/or states of shock and/or narcolepsy and/or epilepsy and/or excess weight and/or asthma and/or glaucoma and/or hyperkinetic syndrome; inertia and/or bulimia and/or anorexia and/or catalepsy and/or for anxiolysis and/or for increasing alertness and/or libido; bipolar disturbances and/or postmenopausal hot flushes and/or amyotropic lateral sclerosis (ALS) and/or reflex-sympathetic dystrophy (RSD) and/or spastic paralysis and/or restless leg syndrome and/or acquired nystagmus and/or multiple sclerosis and/or Parkinson's disease and/or Alzheimer's disease and/or Huntington's chorea.

The invention will be described in more detail hereinafter by examples, without being limited thereto.

EXAMPLES

The chemicals and solvents used were obtained commercially from one of the following suppliers: Acros, Geel; Avocado, Port of Heysham; Aldrich, Deisenhofen; Fluka, Seelze; Lancaster, Mulheim; Maybridge, Tintagel; Merck, Darmstadt; Sigma, Deisenhofen; TC1, Japan; or produced by processes generally known in the prior art and particularly known to persons skilled in the art.

The thin layer chromatographic tests were carried out using HPTLC chromatoplates, silica gel 60 F 154 from E. Merck, Darmstadt.

Each sample was analysed by ESI-MS and/or NMR. Mass spectrometric tests (ESI-MS) were carried out using a mass spectrometer from Finnegan, LCQ Classic. $^1$H-NMR tests of the compounds according to the invention were carried out using a 300 MHz DPX Advance NMR device from Bruker.
Production of Substituted 1-oxa-2,8-diaza-spiro[4,5]dec-2-ene Derivatives According to the Invention
4-methylene-piperidine-1-carboxylic Acid Tert-butylester 1.6 g (14 mmol) potassium tert-butylate were added while stirring at 0° C. (ice bath) to a suspension of 5.34 g (15 mmol) methyltriphenylphosphonium bromide in 50 ml diethylether. After stirring for 15 minutes a solution of 2.00 g (10 mmol) 1-boc-4-piperidone (from Merck KGaA) in 15 mmol diethylether was slowly added. The suspension was stirred for a further 30 min at 0° C. After adding 60 ml 10% aqueous NH$_4$Cl solution, the organic phase was separated, dried over magnesium sulphate and the solvent removed under vacuum. After chromatography on silica gel (hexane:ethylacetate=5:1) 1.71 g (89%) 4-methylene-piperdine-1-carboxylic acid tert-butylester were obtained as a colorless liquid.

$^1$H-NMR-spectrum (d$_6$-DMSO/TMS$_{ext.}$): δ=1.47 ppm (s, 9H, C(CH$_3$)$_3$); 2.16-2.19 ppm (m, 4H, CH$_2$); 3.40-3.44 ppm (m, 4H, CH$_2$); 4.74 (s, 2H, C=CH$_2$).
1-oxa-2,8-diaza-spiro[4,5]dec-2-ene-3,8-dicarboxylic Acid 8-tert-butylester 3-ethylester 0.55 ml (3.9 mmol) of previously freshly distilled triethylamine were slowly added at 0° C. (ice bath) to a mixture of 0.50 g (2.6 mmol) 4-methylene-piperidine-1-carboxylic acid tert-butylester and 0.60 g (3.9 mmol) 2-chloro-2-hydroxyiminoethylacetate in 10 ml dichloromethane. After stirring for 12 hours at ambient temperature, 0.79 g (5.1 mmol) of 2-chloro-2-hydroxyiminoethylacetate and 0.72 ml (5.1 mmol) triethylamine were added at 0° C. and stirred for a further 24 hours.

After washing with 10% aqueous citric acid and saturated aqueous NaCl a yellow oil was obtained after drying the organic phase (MgSO$_4$) and removing the solvent under vacuum. After column chromatography on silica gel (hexane: diethylether=4:1) 320 mg (39%) 1-oxa-2,8-diaza-spiro[4,5] dec-2-ene-3,8-dicarboxylic acid 8-tert-butylester 3-ethylester was obtained in the form of a slightly yellow colored oil.

$^1$H-NMR-spectrum (d$_6$-DMSO/TMS$_{ext.}$): δ=1.37 ppm (t, J=6.0Hz, 3H, CH$_3$); 1.46 ppm (s, 9H, C(CH$_3$)$_3$); 1.67-1.75 ppm (m, 2H, CH$_2$); 1.85-1.92 ppm (m, 2H, CH$_2$); 2.96 ppm (s, 2H, CH$_2$); 3.39-3.49 ppm (m, 2H, CH$_2$); 3.60-3.70 ppm (m, 2H, CH$_2$); 4.35 (q, J=6.0Hz, 2H, CH$_2$).

1-oxa-2,8-diaza-spiro[4,5]dec-2-ene-3,8-dicarboxylic Acid 8-tert-butylester

A mixture of 320 mg (1 mmol) of 4-methylene-piperidine-1-carboxylic acid tert-butylester-3-ethylester in 2 ml MeOH and 70 mg (1.5 mmol) lithium hydroxide monohydrate in 1.3 ml H$_2$O were stirred for 1.5 hours at ambient temperature. After removing the solvent mixture under vacuum the residue was absorbed in water and ethylacetate and partitioned, the aqueous phase being adjusted with citric acid to pH=4. The organic phase was dried (MgSO$_4$) and of solvent removed under vacuum. 280 mg (98%) of the free acid in the form of a colorless solid were obtained.

$^1$H-NMR-spectrum (d$_6$-DMSO/TMS$_{ext.}$): δ=1.47 ppm (s, 9H, C(CH$_3$)3); 1.73-1.78 ppm (m, 2H, CH$_2$); 1.88-1.93 ppm (m, 2H, CH$_2$); 2.97 ppm (s, 2H, CH$_2$); 3.39-3.48 ppm (m, 2H, CH$_2$); 3.65-3.74 ppm (m, 2H, CH$_2$); 9.35 (s, 1H, COOH).

General Instructions for Reacting 1-oxa-2,8-diaza-spiro[4,5] dec-2-ene-3,8-dicarboxylic Acid 8-tert-butyl Ester with Primary or Secondary Amines A mixture of one equivalent of 1-oxa-2,8-diaza-spiro[4,5] dec-2-ene-3.8-dicarboxylic acid 8-tert-butyl ester, one equivalent of the respective amine, 2.7 equivalents of N-methylmorpholine and 1.8 equivalents castro-reagent (BOP reagent) in DMF was stirred for 12 hours at ambient temperature. After removing the DMF under vacuum the residue was mixed with H$_2$O and ethyl acetate and partitioned. The organic phase was washed with H$_2$O, 10% citric acid, saturated Na$_2$CO$_3$ solution and saturated NaCl solution, dried (MgSO$_4$) and the solvent removed under vacuum. After column chromatography (silica gel, diethyl ether: hexane=10:1) the respective coupling products were obtained.

In some cases the coupling with DCC (1 equivalent), 1-hydroxybenzotriazole (1 equivalent) and triethylamine (1 equivalent) in DMF was carried out at 0° C. After 1 hour at 0° C. the mixture was heated to ambient temperature and stirred for a further 12 hours. The mixture was then filtered and the filtrate partitioned between aqueous saturated NaHCO$_3$ solution and diethylether. The organic phase was washed with 10% citric acid, saturated NaHCO$_3$ solution and saturated NaCl solution, dried (MgSO$_4$) and the from solvent removed under vacuum. After column chromatography (silica gel, diethyl ether: hexane=10:1) the respective coupling products were obtained.

3-benzylcarbamoyl-1-oxa-2,8-diaza-spiro[4,5]dec-2-ene-8-carboxylic Acid tert-butylester 250 mg (56%) of 3-benzylcarbamoyl-1-oxa-2,8-diazaspiro[4,5]dec-2-ene-8-carboxylic acid tert-butylester were obtained in form of a colorless solid analogously to the above-described general instructions (with castro-reagent) from 340 mg (1.2 mmol) 1-oxa-2,8-diaza-spiro[4,5]dec-2-ene-3.8-dicarboxylic acid 8-tert-butylester and 130 mg (1.2 mmol) benzylamine.

$^1$H-NMR-spectrum (d$_6$-DMSO/TMS$_{ext.}$): δ=1.46 ppm (s, 9H, C(CH$_3$)$_3$); 1.63-1.70 ppm (m, 2H, CH$_2$); 1.79-1.89 ppm (m, 2H, CH$_2$); 2.98 ppm (s, 2H, CH$_2$); 3.-3.45 ppm (m, 2H, CH$_2$); 3.55-3.65 ppm (m, 2H, CH$_2$); 4,51 ppm (d, J=6Hz, 2H, N—CH$_2$); 7.15-7.20 ppm (m, 1H, NH); 7.26-7.33 ppm (m, 5H, aryl-H).

R,R-3-(2-benzyloxy-cyclopentylcarbamoyl)-1-oxa-2,8-diaza-spiro[4,5]dec-2-ene-8-carboxylic Acid Tert-butylester 700 mg (55%) R,R-3-(2-benzyloxy-cyclopentylcarbamoyl)-1-oxa-2,8-diaza-spiro[4,5]dec-2-ene-8-carboxylic acid tert-butylester were obtained in the form of a colorless solid analogously to the foregoing general instructions (with DCC) from 800 mg (2.8 mmol) 1-oxa-2,8-diaza-spiro[4,5]dec-2-ene-3.8-dicarboxylic acid 8-tert-butylester and 540 mg (2.8 mmol) R,R-2-benzyloxy-cyclopentylamine.

$^1$H-NMR-spectrum (d$_6$-DMSO/TMS$_{ext.}$): δ=1.46 ppm (s, 9H, C(CH$_3$)$_3$); 1.60-2.00 ppm (m, 9H, CH$_2$); 2.15-2.30 ppm (m, 1H, CH$_2$); 2.99 ppm (s, 2H, CH$_2$); 3.40-3.50 ppm (m, 2H, CH$_2$); 3.59-3.65 ppm (m, 2H, CH$_2$); 3.80-3.90 ppm (m, 1H, CH); 4.25-4.35 ppm (m, 1H, CH); 4.61 ppm (m, 2H, O—CH$_2$); 6,51-6,53 ppm (m, 1H, NH); 7.25-7.34 ppm (m, 5H, aryl-H).

General Instructions for Splitting the Boc Group

The appropriate N-Boc-piperidine was mixed with an excess of a 4M methanolic HCl solution at ambient temperature and stirred (DC control). After complete reaction the solution was evaporated to the first clouding, then mixed with diethylether and stored overnight at 4° C. to complete the precipitation. The precipitated solid was filtered, washed with small portions of diethylether and dried under vacuum.

1-oxa-2,8-diaza-spiro[4,5]dec-2-ene-3-carboxylic Acid Benzylamide-hydrochloride 130 mg (60%) 1-oxa-2,8-diaza-spiro[4,5]dec-2-ene-3-carboxylic acid benzylamide were obtained as a hydrochloride in the form of a colorless solid analogously to the above-described instructions from 250 mg (0.7 mmol) 3-benzylcarbamoyl-1-oxa-2,8-diaza-spiro[4,5]dec-2-ene-8-carboxylic acid tert-butylester.

$^1$H-NMR-spectrum (d$_6$-DMSO/TMS$_{ext.}$): δ=1.92-2.06 ppm (m, 4H, CH$_2$); 3.10-3.18 ppm (m, 6H, CH$_2$); 4.31-4.40 ppm (m, 2H, CH$_2$); 7.15-7.33 ppm (m, 5H, aryl-H); 8.99-9.13 ppm (m, 3H, NH).

R,R-1-oxa-2,8-diaza-spiro[4,5]dec-2-ene-3-carboxylic Acid (2-benzyloxy-cyclopentyl)-amide Hydrochloride 490 mg (50%) R,R-1-oxa-2,8-diaza-spiro[4,5]dec-2-ene-3-carboxylic acid (2-benzyloxy-cyclopentyl)-amide were obtained as a hydrochloride in the form of a colorless solid analogously to the general instructions from 700 mg (2.5 mmol) R,R-3-(2-benzyloxy-cyclopentylcarbamoyl)-1-oxa-2,8-diaza-spiro[4,5]dec-2-ene-8-carboxylic acid tert-butylester.

$^1$H-NMR-spectrum (d$_6$-DMSO/TMS$_{ext.}$): δ=1.50-1.75 ppm (m, 4H, CH$_2$); 1.92-2.11 ppm (m, 6H, CH$_2$); 3.06-3.20 ppm (m, 6H, CH$_2$); 3.82-3.95 ppm (m, 1H, CH); 4.10-4.20 ppm (m, 1H, CH); 4.42-4.60 ppm (m, 2H, O—CH$_2$); 7.20-7.34 ppm (m, 5H, aryl-H); 8.47-8.54 ppm (m, 1H, NH); 9.05-9.15 ppm (m, 2H, NH).

General Instructions for Reacting the Piperidines with Carboxylic Acid Halides or Sulphonic Acid Halides The respective piperidine (1 equivalent) was added at 0° C. to a solution of the corresponding acid halide (1.5 equivalents), triethylamine (2 equivalents) and N,N-dimethyl-4-aminopyridine (DMAP; catalytic quantities) in dichloromethane. The mixture was heated to ambient temperature and stirred overnight. After hydrolysis with 10% aqueous NH$_4$Cl solution, the organic phase was dried (MgSO$_4$) and the solvent removed under vacuum. After column chromatography on silica gel (ethylacetate-hexane mixtures of variable composition) the target compounds were obtained.

8-(2-benzyloxy-acetyl)-1-oxa-2,8-diaza-spiro[4,5]dec-2-ene-3-carboxylic Acid Benzylamide (Example 219)

120 mg (0.42 mmol) 1-oxa-2,8-diaza-spiro[4,5]dec-2-ene-3-carboxylic acid benzylamide (base, freed using aqueous NaOH) were reacted analogously to the above-mentioned general instructions with 116 mg (0.63 mmol) benzyloxyacetyl chloride to 60 mg (34% 8-(2-benzyloxy-acetyl)-1-oxa-2,8-diaza-spiro[4,5]dec-2-ene-3-carboxylic acid benzylamide. A colorless oil which crystallized slowly after being set aside at ambient temperature for a prolonged period was obtained.

$^1$H-NMR-spectrum (d$_6$-DMSO/TMS$_{ext.}$): δ=1.55-1.69 ppm (m, 2H, CH$_2$); 1.75-1.85 ppm (m, 2H, CH$_2$); 2.92 ppm (s, 2H, CH$_2$); 3.20-3.32 ppm (m, 1H, CH$_2$); 3.35-3.48 ppm (m, 1H, CH$_2$); 3.50-3.60 (m, 1H, CH$_2$); 3.94-4.05 ppm (m, 1H, CH$_2$); 6,95-7.05 ppm (m, 1H, NH); 7.15-7.35 ppm (m, 10H, aryl-H).

R,R-8-(5-chloro-thiophene-2-sulphonyl)-1-oxa-2,8-diaza-spiro[4,5]dec-2-ene-3-carboxylic Acid (2-benzyloxy-cyclopentyl)-amide (Example 220)

490 mg (1.24 mmol) of R,R-1-oxa-2,8-diaza-spiro[4,5]dec-2-ene-3-carboxylic acid (2-benzyloxy-cyclopentyl)-amide (base, freed using aqueous NaOH) were reacted as described above with 410 mg (1.86 mmol) 5-chlorothiophene-2-sulphonylchloride to form 480 mg (72%) 8-(5-chloro-thiophene-2-sulphonyl)-1-oxa-2,8-diaza-spiro[4,5]dec-2-ene-3-carboxylic acid (2-benzyloxy-cyclopentyl)-amide. A colorless crystalline solid was obtained.

$^1$H-NMR-spectrum (d$_6$-DMSO/TMS$_{ext.}$): δ=1.40-1.55 ppm (m, 1H, CH$_2$); 1.60-2.05 ppm (m, 8H, CH$_2$); 2.10-2.30 ppm (m, 1H, CH$_2$); 2.93-3.05 ppm (m, 2H, CH$_2$); 2.00 ppm (m, 2H, CH$_2$); 3.41-3.55 ppm (m, 2H, CH$_2$); 3.75-3.88 ppm (m, 1H, CH); 4.20-4.32 ppm (m, 1H, CH); 4.42-4.60 ppm (m, 2H, O—CH$_2$); 6.42-6.48 (d, 1H, aryl-H); 7.00 ppm (d, J=3Hz, 1H, aryl-H); 7.22-7.40 ppm (m, 5H, aryl-H).

The compounds listed in Table 1 were produced by this process. Alternatively, simultaneous synthetic, semi-automatic production is also possible.

TABLE 1

| Example | Compound |
|---|---|
| 1 | 3-(1H-indol-3-yl)-2-{[8-(4-trifluoromethoxy-benzenesulphonyl)-1-oxa-2,8-diaza-spiro[4,5]dec-2-ene-3-carbonyl]-amino}-propionic acid methyl ester |
| 2 | {4-[(8-phenylmethanesulphonyl-1-oxa-2,8-diaza-spiro[4,5]dec-2-ene-3-carbonyl) amino-benzyl}phosphonic acid diethylester |
| 3 | (4-cycloheptyl-piperazin-1-yl)-[8-(thiophene-2-sulphonyl)-1-oxa-2,8-diaza-spiro [4,5]dec-2-en-3-yl]-methanone |
| 4 | [8-(5-chloro-thiophene-2-sulphonyl)-1-oxa-2,8-diaza-spiro[4,5]dec-2-en-3-yl]-(4-phenyl-piperazin-1-yl)-methanone |
| 5 | 8-(2-chloro-4-nitro-benzoyl)-1-oxa-2,8-diaza-spiro[4,5]dec-2-ene-3-carboxylic acid cyclopentylamide |
| 6 | (4-naphthalen-2-ylmethyl-piperazin-1-yl)-(8-phenylmethanesulphonyl-1-oxa-2,8 diaza-spiro[4,5]dec-2-en-3-yl)-methanone |
| 7 | 8-dimethylsulphamoyl-1-oxa-2,8-diaza-spiro[4,5]dec-2-ene-3-carboxylic acid phenethyl-amide |
| 8 | 8-(thiophene-2-sulphonyl)-1-oxa-2,8-diaza-spiro[4,5]dec-2-ene-3-carboxylic acid (1-phenyl-ethyl)-amide |
| 9 | 8-(toluene-4-sulphonyl)-1-oxa-2,8-diaza-spiro[4,5]dec-2-ene-3-carboxylic acid [2-(3,4-dichloro-phenyl-ethyl)]-amide |
| 10 | 4-diethylamino-benzoic acid N'-[8-(thiophene-2-sulphonyl)-1-oxa-2,8-diaza-spiro[4,5]dec-2-ene-3-carbonyl]-hydrazide |
| 11 | 8-(3-chloro-4-fluorobenzenesulphonyl)-1-oxa-2,8-diaza-spiro[4,5]dec-2-ene-3 carboxylic acid 2-pyrrolidin-1-yl-ethyl)-amide |
| 12 | 8-phenylmethanesulphonyl-1-oxa-2,8-diaza-spiro[4,5]dec-2-ene-3-carboxylic acid phenethyl-amide |
| 13 | 8-benzenesulphonyl-1-oxa-2,8-diaza-spiro[4,5]dec-2-ene-3-carboxylic acid (2-dimethylamino-ethyl)-amide |
| 14 | [4-(3-phenyl-propyl)-piperazin-1-yl]-[8-(thiophene-2-sulphonyl)-1-oxa-2,8-diaza-spiro[4,5]dec-2-en-3-yl]-methanone |
| 15 | 8-(2,5-dichloro-benzenesulphonyl)-1-oxa-2,8-diaza-spiro[4,5]dec-2-ene-3-carboxylic acid[3-(2-methyl-piperidin-1-yl)-propyl]-amide |
| 16 | 8-(4-trifluoromethoxy-benzenesulphonyl)-1-oxa-2,8-diaza-spiro[4,5]dec-2-ene-3 carboxylic acid [2-(1 H-indol-3-yl)-ethyl]-methyl-amide |
| 17 | 8-(5-fluoro-2-methyl-benzenesulphonyl)-1-oxa-2,8-diaza-spiro[4,5]dec-2-ene-3 carboxylic acid (2-acetylamino-ethyl)-amide |
| 18 | 8-(toluene-4-sulphonyl)-1-oxa-2,8-diaza-spiro[4,5]dec-2-ene-3-carboxylic acid benzyl-phenethyl-amide |
| 19 | 8-(2-methyl-5-nitro-benzenesulphonyl)-1-oxa-2,8-diaza-spiro[4,5]dec-2-ene-3 carboxylic acid (2-dimethylamino-ethyl)-amide |
| 20 | 8-phenylmethanesulphonyl-1-oxa-2,8-diaza-spiro[4,5]dec-2-ene-3-carboxylic acid (2-benzyloxy-cyclopentyl)-amide |
| 21 | 8-(thiophene-2-sulphonyl)-1-oxa-2,8-diaza-spiro[4,5]dec-2-ene-3-carboxylic acid (2,3-dihydro-benzo[1,4]dioxin-2-ylmethyl)-amide |
| 22 | 8-(toluene-4-sulphonyl)-1-oxa-2,8-diaza-spiro[4,5]dec-2-ene-3-carboxylic acid (4-phenoxy-phenyl)-amide |
| 23 | 8-(thiophene-2-sulphonyl)-1-oxa-2,8-diaza-spiro[4,5]dec-2-ene-3-carboxylic acid (1-p-tolyl-ethyl)-amide |
| 24 | 8-(thiophene-2-sulphonyl)-1-oxa-2,8-diaza-spiro[4,5]dec-2-ene-3-carboxylic acid 3-fluorobenzylamide |
| 25 | 2-phenyl-l-{4-[8-(toluene-4-sulphonyl)-1-oxa-2,8-diaza-spiro[4,5]dec-2-ene-3 carbonyl]-piperazin-1-yl}-ethanone |
| 26 | 8-(thiophene-2-sulphonyl)-1-oxa-2,8-diaza-spiro[4,5]dec-2-ene-3-carboxylic acid [1-(4-trifluoromethyl-benzyl)-pyrrolidin-3-yl]-amide |

TABLE 1-continued

| Example | Compound |
|---|---|
| 27 | [8-(thiophene-2-sulphonyl)-1-oxa-2,8-diaza-spiro[4,5]dec-2-en-3-yl]-(4-o-tolyl-piperazin-1-yl)-methanone |
| 28 | 8-(toluene-4-sulphonyl)-1-oxa-2,8-diaza-spiro[4,5]dec-2-ene-3-carboxylic acid benzyl-(2-cyano-ethyl)-amide |
| 29 | [8-(2,5-dichloro-benzenesulphonyl)-1-oxa-2,8-diaza-spiro[4,5]dec-2-en-3-yl]-(4thieno[2,3-d]pyrimidin-4-yl-piperazin-1-yl-methanone |
| 30 | 8-(5-chloro-thiophene-2-sulphonyl)-1-oxa-2,8-diaza-spiro[4,5]dec-2-ene-3-carboxylic acid (benzo[1,3]dioxol-5-ylmethyl)-amide |
| 31 | (3-methyl-4-m-tolyl-piperazin-1-yl)-[8-(thiophene-2-sulphonyl)-1-oxa-2,8-diaza-spiro[4,5]dec-2-en-3-yl]-methanone |
| 32 | [4-(1-phenyl-ethyl)-piperazin-1-yl]-[8-(toluene-4-sulphonyl)-1-oxa-2,8-diaza-spiro[4,5]dec-2-en-3-yl]-methanone |
| 33 | [4-(2,4-dimethyl-phenyl)-piperazin-1-yl]-[8-(toluene-4-sulphonyl)-1-oxa-2,8-diaza spiro[4,5]dec-2-en-3-yl]-methanone |
| 34 | 8-(2-chloro-pyridine-3-carbonyl)-1-oxa-2,8-diaza-spiro[4,5]dec-2-ene-3-carboxylic acid cyclopentylamide |
| 35 | (4-naphthalen-2-ylmethyl-piperazin-1-yl)-[8-(3-trifluoromethyl-benzenesulphonyl)-1-oxa-2,8-diaza-spiro[4,5]dec-2-en-3-yl]-methanone |
| 36 | 8-[3-phenyl-2-(toluene-4-sulphonylamino)-propionyl]-1-oxa-2,8-diaza-spiro[4,5]dec-2-ene-3-carboxylic acid pyridin-3-ylmethyl)-amide |
| 37 | 8-(5-fluoro-2-methyl-benzenesulphonyl)-1-oxa-2,8-diaza-spiro[4,5]dec-2-ene-3-carboxylic acid (2-dimethylamino-ethyl)-amide |
| 38 | 8-(4-nitro-benzenesulphonyl)-1-oxa-2,8-diaza-spiro[4,5]dec-2-ene-3-carboxylic acid (thiophen-2-ylmethyl)-amide |
| 39 | 8-(2,5-dichloro-benzenesulphonyl)-1-oxa-2,8-diaza-spiro[4,5]dec-2-ene-3-carboxylic acid 3-fluoro-5-trifluoromethyl-benzylamide |
| 40 | 8-(5-chloro-thiophene-2-sulphonyl)-1-oxa-2,8-diaza-spiro[4,5]dec-2-ene-3 carboxylic acid benzhydryl-amide |
| 41 | 8-[3-phenyl-2-(toluene-4-sulphonylamino)-propionyl]-1-oxa-2,8-diaza-spiro[4,5]dec-2-ene-3-carboxylic acid (2-cyano-ethyl)-amide |
| 42 | [(8-phenylmethanesulphonyl-1-oxa-2,8-diaza-spiro[4,5]dec-2-ene-3-carbonyl) amino]-ethyl acetate |
| 43 | 8-(3-dimethylamino-benzoyl)-1-oxa-2,8-diaza-spiro[4,5]dec-2-ene-3-carboxylic acid (2-cyano-ethyl)-amide |
| 44 | 8-(2,5-dichloro-benzenesulphonyl)-1-oxa-2,8-diaza-spiro[4,5]dec-2-ene-3-carboxylic acid [1-(naphthalen-2-ylcarbamoyl)-ethyl]amide |
| 45 | 8-(toluene-4-sulphonyl)-1-oxa-2,8-diaza-spiro[4,5]dec-2-ene-3-carboxylic acid (1-p-tolyl-ethyl)-amide |
| 46 | [4-(4-chloro-phenyl)-piperazin-1-yl]-(8-phenylmethanesulphonyl-1-oxa-2,8-diaza-spiro[4,5]dec-2-en-3-yl)-methanone |
| 47 | 8-(thiophene-2-sulphonyl)-1-oxa-2,8-diaza-spiro[4,5]dec-2-ene-3-carboxylic acid (2-benzyloxy-cyclopentyl)-amide |
| 48 | 8-acetyl-1-oxa-2,8-diaza-spiro[4,5]dec-2-ene-3-carboxylic acid benzylamide |
| 49 | 8-(5-chloro-thiophene-2-sulphonyl)-1-oxa-2,8-diaza-spiro[4,5]dec-2-ene-3 carboxylic acid 2,5-difluoro-benzylamide |
| 50 | 8-(5-chloro-thiophene-2-sulphonyl)-1-oxa-2,8-diaza-spiro[4,5]dec-2-ene-3 carboxylic acid (1-naphthalen-2-ylmethyl-pyrrolidin-3-yl)-amide |
| 51 | 8-phenylmethanesulphonyl-1-oxa-2,8-diaza-spiro[4,5]dec-2-ene-3-carboxylic acid 2-ethoxy-benzylamide |
| 52 | 8-(4-ethyl-benzoyl)-1-oxa-2,8-diaza-spiro[4,5]dec-2-ene-3-carboxylic acid (thiophen-2-ylmethyl)-amide |
| 53 | 2-{[8-(2,5-dichloro-benzenesulphonyl)-1-oxa-2,8-diaza-spiro[4,5]dec-2-ene-3-carbonyl]-amino-succinic acid 1-allyl ester 4-tert-butyl ester |
| 54 | 8-(4-trifluoromethoxy-benzenesulphonyl)-1-oxa-2,8-diaza-spiro[4,5]dec-2-ene-3-carboxylic acid naphthalen-2-ylamide |
| 55 | 4-{[8-(2-phenyl-cyclopropanecarbonyl)-1-oxa-2,8-diaza-spiro[4,5]dec-2-ene-3-carbonyl]-amino}-piperidine-1-carboxylic acid ethyl ester |
| 56 | 4-{[8-(2,4-difluoro-benzoyl)-1-oxa-2,8-diaza-spiro[4,5]dec-2-ene-3-carbonyl]-amino}-piperidine-1-carboxylic acid ethyl ester |
| 57 | 8-(toluene-4-sulphonyl)-1-oxa-2,8-diaza-spiro[4,5]dec-2-ene-3-carboxylic acid (2-dimethylamino-ethyl)-amide |
| 58 | 8-dimethylsulphamoyl-1-oxa-2,8-diaza-spiro[4,5]dec-2-ene-3-carboxylic acid [2-(4-chlorophenyl)-ethyl]-amide |
| 59 | 8-(4-methoxy-benzoyl)-1-oxa-2,8-diaza-spiro[4,5]dec-2-ene-3-carboxylic acid (5-methyl-furan-2-ylmethyl-amide |
| 60 | 8-(thiophene-2-sulphonyl)-1-oxa-2,8-diaza-spiro[4,5]dec-2-ene-3-carboxylic acid [2-(4-chlorophenyl)-ethyl]-amide |
| 61 | 8-(5-chloro-thiophene-2-sulphonyl)-1-oxa-2,8-diaza-spiro[4,5]dec-2-ene-3-carboxylic acid [2-(1-methyl-pyrrolidin-2-yl)-ethyl]-amide |
| 62 | 4-{[8-(4-bromo-benzoyl)-1-oxa-2,8-diaza-spiro[4,5]dec-2-ene-3-carbonyl]-amino)-piperidine-1-carboxylic acid ethyl ester |
| 63 | 8-(toluene-4-sulphonyl)-1-oxa-2,8-diaza-spiro[4,5]dec-2-ene-3-carboxylic acid 3,5-dichlorobenzylamide |
| 64 | 8-(2,5-dichloro-benzenesulphonyl)-1-oxa-2,8-diaza-spiro[4,5]dec-2-ene-3-carboxylic acid[1-(3-methoxy-benzyl-pyrrolidin-3-yl]-amide |
| 65 | 3-(4-naphthalen-2-ylmethyl-piperazine-1-carbonyl)-1-oxa-2,8-diaza-spiro[4,5]dec-2-ene-8-sulphonic acid dimethylamide |

TABLE 1-continued

| Example | Compound |
|---|---|
| 66 | 3-{[8-(7,7-dimethyl-2-oxo-bicyclo[2.2.1]hept-1-ylmethanesulphonyl)-1-oxa-2,8-diaza-spiro[4,5]dec-2-ene-3-carbonyl]-amino}-propionic acid ethyl ester |
| 67 | 8-(toluene-4-sulphonyl)-1-oxa-2,8-diaza-spiro[4,5]dec-2-ene-3-carboxylic acid (2-benzyloxy-cyclopentyl)-amide |
| 68 | 8-(2,5-dichloro-benzenesulphonyl)-1-oxa-2,8-diaza-spiro[4,5]dec-2-ene-3-carboxylic acid 3,4-dimethoxy-benzylamide |
| 69 | (8-phenylmethanesulphonyl-1-oxa-2,8-diaza-spiro[4,5]dec-2-en-3-yl)-[4-(3-phenyl-propyl-piperazin-1-yl)]-methanone |
| 70 | 3-(4-thieno[2,3-d]pyrimidin-4-yl-piperazine-1-carbonyl)-1-oxa-2,8-diaza-spiro[4,5]dec-2-ene-8-sulphonic acid dimethylamide |
| 71 | [8-(5-chloro-thiophene-2-sulphonyl)-1-oxa-2,8-diaza-spiro[4,5]dec-2-en-3-yl]-[4-(3,5-dimethoxy-phenyl)-piperazin-1-yl]-methanone |
| 72 | 8-dimethylsulphamoyl-1-oxa-2,8-diaza-spiro[4,5]dec-2-ene-3-carboxylic acid 3-fluoro-4-trifluoromethyl-benzylamide |
| 73 | 8-(toluene-4-sulphonyl)-1-oxa-2,8-diaza-spiro[4,5]dec-2-ene-3-carboxylic acid (2-benzyloxy-cyclopentyl)-amide |
| 74 | 4-[(8-butyryl-1-oxa-2,8-diaza-spiro[4,5]dec-2-ene-3-carbonyl)-amino]-piperidine-1-carboxylic acid ethyl ester |
| 75 | 8-(toluene-4-sulphonyl)-1-oxa-2,8-diaza-spiro[4,5]dec-2-ene-3-carboxylic acid (2-phenyl-cyclopropyl)-amide |
| 76 | [8-(4-fluoro-benzenesulphonyl)-1-oxa-2,8-diaza-spiro[4,5]dec-2-ene-3-yl]-[4-(5-methyl-pyrazine-2-carbonyl)-piperazin-1-yl]-methanone |
| 77 | 8-dimethylsulphamoyl-1-oxa-2,8-diaza-spiro[4,5]dec-2-ene-3-carboxylic acid 2,4-difluorobenzylamide |
| 78 | 8-phenylmethanesulphonyl-1-oxa-2,8-diaza-spiro[4,5]dec-2-ene-3-carboxylic acid [2-(3-fluorophenyl)-ethyl]-amide |
| 79 | 8-(5-chloro-thiophene-2-sulphonyl)-1-oxa-2,8-diaza-spiro[4,5]dec-2-ene-3-carboxylic acid (2,2-diphenyl-ethyl)-amide |
| 80 | 3-[4-(3-phenyl-propyl)-piperazine-1-carbonyl]-1-oxa-2,8-diaza-spiro[4,5]dec-2-ene-8-sulphonic acid dimethylamide |
| 81 | 3-{[8-(3,5-difluoro-benzoyl)-1-oxa-2,8-diaza-spiro[4,5]dec-2-ene-3-carbonyl]-amino}-propionic acid ethyl ester |
| 82 | 8-(propane-1-sulphonyl)-1-oxa-2,8-diaza-spiro[4,5]dec-2-ene-3-carboxylic acid isobutyl-amide |
| 83 | [4-(3-phenyl-propyl)-piperazin-1-yl]-[8-(3-trifluoromethyl-benzenesulphonyl)-1-oxa-2,8-diaza-spiro[4,5]dec-2-en-3-yl]-methanone |
| 84 | 8-(thiophene-2-sulphonyl)-1-oxa-2,8-diaza-spiro[4,5]dec-2-ene-3-carboxylic acid [1-(2,3-dihydro-benzo[1,4]dioxin-5-yl)-ethyl]-amide |
| 85 | 8-butyryl-1-oxa-2,8-diaza-spiro[4,5]dec-2-ene-3-carboxylic acid phenylamide |
| 86 | 8-(4-trifluoromethoxy-benzenesulphonyl)-1-oxa-2,8-diaza-spiro[4,5]dec-2-ene-3-carboxylic acid cyclooctylamide |
| 87 | 8-[2-(2-methoxy-ethoxy)-acetyl]-1-oxa-2,8-diaza-spiro[4,5]dec-2-ene-3-carboxylic acid benzylamide |
| 88 | 8-(4-bromo-3-methyl-benzoyl)-1-oxa-2,8-diaza-spiro[4,5]dec-2-ene-3-carboxylic acid isobutyl-amide |
| 89 | 8-(5-chloro-thiophene-2-sulphonyl)-1-oxa-2,8-diaza-spiro[4,5]dec-2-ene-3-carboxylic acid [3-methyl-phenyl-amino)-propyl]-amide |
| 90 | 4-{[8-(2-methyl-5-nitro-benzenesulphonyl)-1-oxa-2,8-diaza-spiro[4,5]dec-2-ene-3-carbonyl]-amino}-piperidine-1-carboxylic acid ethyl ester |
| 91 | [8-(5-chloro-thiophene-2-sulphonyl)-1-oxa-2,8-diaza-spiro[4,5]dec-2-en-3-yl]-[4-(4-fluorophenyl)-piperazin-1-yl]-methanone |
| 92 | 8-(2,5-dichloro-benzenesulphonyl)-1-oxa-2,8-diaza-spiro[4,5]dec-2-ene-3-carboxylic acid methyl-pyridin-3-ylmethyl-amide |
| 93 | 2-(3,4-difluoro-phenyl)-1-{4-[8-(3-trifluoromethyl-benzenesulphonyl)-1-oxa-2,8-diaza-spiro[4,5]dec-2-ene-3-carbonyl]-piperazin-1-yl-ethanone |
| 94 | 8-(3-trifluoromethyl-benzenesulphonyl)-1-oxa-2,8-diaza-spiro[4,5]dec-2-ene-3 carboxylic acid cyclopropylmethyl-amide |
| 95 | 3-{[8-(2-methyl-5-nitro-benzenesulphonyl)-1-oxa-2,8-diaza-spiro[4,5]dec-2-ene-3-carbonyl]-amino}-propionic acid ethyl ester |
| 96 | 8-[2-(3-chloro-phenoxy)-acetyl]-1-oxa-2,8-diaza-spiro[4,5]dec-2-ene-3-carboxylic acid (thiophen-2-ylmethyl)-amide |
| 97 | 8-(4-trifluoromethoxy-benzenesulphonyl)-1-oxa-2,8-diaza-spiro[4,5]dec-2-ene-3-carboxylic acid benzyl-phenethyl-amide |
| 98 | 8-(2,5-dichloro-benzenesulphonyl)-1-oxa-2,8-diaza-spiro[4,5]dec-2-ene-3-carboxylic acid benzyl-phenethyl-amide |
| 99 | 8-(2,5-dichloro-benzenesulphonyl)-1-oxa-2,8-diaza-spiro[4,5]dec-2-ene-3-carboxylic acid (2-cyano-ethyl)-pyridin-3-ylmethyl-amide |
| 100 | 8-(2,5-dichloro-benzenesulphonyl)-1-oxa-2,8-diaza-spiro[4,5]dec-2-ene-3-carboxylic acid (2-cyano-ethyl)-(tetrahydro-furan-2-ylmethyl-amide |
| 101 | 8-(3-trifluoromethyl-benzenesulphonyl)-1-oxa-2,8-diaza-spiro[4,5]dec-2-ene-3 carboxylic acid methyl-pyridin-3-ylmethyl-amide |
| 102 | 8-(pyridine-4-carbonyl)-1-oxa-2,8-diaza-spiro[4,5]dec-2-ene-3-carboxylic acid benzylamide |
| 103 | 8-(4-trifluoromethoxy-benzenesulphonyl)-1-oxa-2,8-diaza-spiro[4,5]dec-2-ene-3-carboxylic acid ethyl-(2-methyl-allyl)-amide |

TABLE 1-continued

| Example | Compound |
|---|---|
| 104 | 8-(4-methoxy-benzenesulphonyl)-1-oxa-2,8-diaza-spiro[4,5]dec-2-ene-3-carboxylic acid [2-(2-fluorophenyl)-ethyl-amide |
| 105 | 8-(5-tert-butyl-2-methyl-furan-3-carbonyl)-1-oxa-2,8-diaza-spiro[4,5]dec-2-ene-3-carboxylic acid isobutyl-amide |
| 106 | 8-(3-phenyl-acryloyl)-1-oxa-2,8-diaza-spiro[4,5]dec-2-ene-3-carboxylic acid (thiophen-2-ylmethyl-amide |
| 107 | 8-(4-trifluoromethyl-benzoyl)-1-oxa-2,8-diaza-spiro[4,5]dec-2-ene-3-carboxylic acid cyclopropylmethyl-amide |
| 108 | 8-(4-trifluoromethylsulphanyl-benzoyl)-1-oxa-2,8-diaza-spiro[4,5]dec-2-ene-3-carboxylic acid cyclopropylmethyl-amide |
| 109 | 8-(4-bromo-benzoyl)-1-oxa-2,8-diaza-spiro[4,5]dec-2-ene-3-carboxylic acid (5-methyl-furan-2-ylmethyl)-amide |
| 110 | 8-(3-fluoro-4-trifluoromethyl-benzoyl)-1-oxa-2,8-diaza-spiro[4,5]dec-2-ene-3-carboxylic acid cyclopropylmethyl-amide |
| 111 | 8-(7,7-dimethyl-2-oxo-bicyclo[2.2.1]hept-1-ylmethanesulphonyl)-1-oxa-2,8-diaza-spiro[4,5]dec-2-ene-3-carboxylic acid (2-ethylsulphanyl-ethyl)-amide |
| 112 | 8-(2,4-difluoro-benzoyl)-1-oxa-2,8-diaza-spiro[4,5]dec-2-ene-3-carboxylic acid tetrahydro-furan-2-ylmethyl)-amide |
| 113 | {[8-(3-chloro-thiophene-2-carbonyl)-1-oxa-2,8-diaza-spiro[4,5]dec-2-ene-3-carbonyl]-amino}-ethyl acetate |
| 114 | 4-oxo-4-{3-[(thiophen-2-ylmethyl)-carbamoyl]-1-oxa-2,8-diaza-spiro[4,5]dec-2-ene-8-yl}-butyric acid methyl ester |
| 115 | 8-(2-ethylsulphanyl-pyridine-3-carbonyl)-1-oxa-2,8-diaza-spiro[4,5]dec-2-ene-3-carboxylic acid benzylamide |
| 116 | 3-{[8-(2-chloro-benzenesulphonyl)-1-oxa-2,8-diaza-spiro[4,5]dec-2-ene-3-carbonyl]-amino}-propionic acid ethyl ester |
| 117 | 8-(4-trifluoromethoxy-benzoyl)-1-oxa-2,8-diaza-spiro[4,5]dec-2-ene-3-carboxylic acid cyclopropylmethyl-amide |
| 118 | 8-(4-phenoxy-butyryl)-1-oxa-2,8-diaza-spiro[4,5]dec-2-ene-3-carboxylic acid cyclopropylmethyl-amide |
| 119 | [8-(3-trifluoromethyl-benzenesulphonyl)-1-oxa-2,8-diaza-spiro[4,5]dec-2-en-3-yl]-[4-(4-trifluoromethyl-pyridin-2-yl)-piperazin-1-yl-methanone |
| 120 | 8-(2-chloro-5-trifluoromethyl-benzoyl)-1-oxa-2,8-diaza-spiro(4,5]dec-2-ene-3-carboxylic acid cyclopropylmethyl-amide |
| 121 | 8-(4-methoxy-benzenesulphonyl)-1-oxa-2,8-diaza-spiro[4,5]dec-2-ene-3-carboxylic acid (2-benzyloxy-cyclopentyl)-amide |
| 122 | 4-{[8-(3-trifluoromethyl-benzenesulphonyl)-1-oxa-2,8-diaza-spiro[4,5]dec-2-ene-3 carbonyl]-amino}-piperidine-1-carboxylic acid ethyl ester |
| 123 | 8-(2-phenoxy-propionyl)-1-oxa-2,8-diaza-spiro[4,5]dec-2-ene-3-carboxylic acid cyclopropylmethyl-amide |
| 124 | 8-(4-fluoro-benzenesulphonyl)-1-oxa-2,8-diaza-spiro[4,5]dec-2-ene-3-carboxylic acid [2-(3-methoxy-phenyl)-ethyl]-amide |
| 125 | 8-(2-methylsulphanyl-pyridine-3-carbonyl)-1-oxa-2,8-diaza-spiro[4,5]dec-2-ene-3-carboxylic acid isobutyl-amide |
| 126 | 8-(5-tert-butyl-2-methyl-furan-3-carbonyl)-1-oxa-2,8-diaza-spiro[4,5]dec-2-ene-3-carboxylic acid cyclopentylamide |
| 127 | 8-(4-chloro-benzenesulphonyl)-1-oxa-2,8-diaza-spiro[4,5]dec-2-ene-3-carboxylic acid (thiophen-2-ylmethyl)-amide |
| 128 | 8-(5-chloro-thiophene-2-sulphonyl)-1-oxa-2,8-diaza-spiro[4,5]dec-2-ene-3-carboxylic acid naphthalen-1-ylmethyl-amide |
| 129 | 8-(4-trifluoromethoxy-benzenesulphonyl)-1-oxa-2,8-diaza-spiro[4,5]dec-2-ene-3-carboxylic acid [2-(4-fluorophenyl)-ethyl]-amide |
| 130 | 8-(4-bromo-3-methyl-benzoyl)-1-oxa-2,8-diaza-spiro[4,5]dec-2-ene-3-carboxylic acid (pyridin-4-ylmethyl)-amide |
| 131 | 8-(4-methoxy-benzoyl)-1-oxa-2,8-diaza-spiro[4,5]dec-2-ene-3-carboxylic acid benzylamide |
| 132 | 8-(3-trifluoromethyl-benzenesulphonyl)-1-oxa-2,8-diaza-spiro[4,5]dec-2-ene-3-carboxylic acid 3-chlorobenzylamide |
| 133 | (8-phenylmethanesulphonyl-1-oxa-2,8-diaza-spiro[4,5]dec-2-en-3-yl)-(4-o-tolyl-piperazin-1-yl)-methanone |
| 134 | (8-phenylmethanesulphonyl-1-oxa-2,8-diaza-spiro[4,5]dec-2-en-3-yl)-(4-pyridin-2-yl-piperazin-1-yl)-methanone |
| 135 | 8-(4-trifluoromethylsulphanyl-benzoyl)-1-oxa-2,8-diaza-spiro[4,5]dec-2-ene-3-carboxylic acid (thiophen-2-ylmethyl)-amide |
| 136 | 8-(thiophene-2-sulphonyl)-1-oxa-2,8-diaza-spiro[4,5]dec-2-ene-3-carboxylic acid benzylamide |
| 137 | 8-(4-fluoro-benzoyl)-1-oxa-2,8-diaza-spiro[4,5]dec-2-ene-3-carboxylic acid isobutyl-amide |
| 138 | 2-(3-isobutylcarbamoyl-1-oxa-2,8-diaza-spiro[4,5]dec-2-ene-8-sulphonyl)-benzoic acid methyl ester |
| 139 | 2-[(8-dimethylsulphamoyl-1-oxa-2,8-diaza-spiro[4,5]dec-2-ene-3-carbonyl)-amino]-3-phenyl-propionic acid tert-butyl ester |
| 140 | 8-(5-chloro-thiophene-2-sulphonyl)-1-oxa-2,8-diaza-spiro[4,5]dec-2-ene-3-carboxylic acid [1-(2,3-dihydro-benzo[1,4]dioxin-5-yl)-ethyl]-amide |
| 141 | 8-(4-bromo-benzoyl)-1-oxa-2,8-diaza-spiro[4,5]dec-2-ene-3-carboxylic acid (thiophen-2-ylmethyl-amide |

TABLE 1-continued

| Example | Compound |
|---|---|
| 142 | 8-(4-fluoro-benzenesulphonyl)-1-oxa-2,8-diaza-spiro[4,5]dec-2-ene-3-carboxylic acid (3-imidazol-1-yl-propyl)-amide |
| 143 | 4-[8-(4-fluoro-benzenesulphonyl)-1-oxa-2,8-diaza-spiro[4,5]dec-2-ene-3-carbonyl]-piperazine-1-carboxylic acid benzyl ester |
| 144 | 3-(4-cycloheptyl-piperazine-1-carbonyl)-1-oxa-2,8-diaza-spiro[4,5]dec-2-ene-8 sulphonic acid dimethylamide |
| 145 | 4-methyl-2-{[8-(thiophene-2-sulphonyl)-1-oxa-2,8-diaza-spiro[4,5]dec-2-ene-3-carbonyl]-amino}-pentanoic acid tert-butyl ester |
| 146 | 8-(3-chloro-2-fluorobenzoyl)-1-oxa-2,8-diaza-spiro[4,5]dec-2-ene-3-carboxylic acid (thiophen-2-ylmethyl)-amide |
| 147 | 2-{[8-(4-methoxy-benzenesulphonyl)-1-oxa-2,8-diaza-spiro[4,5]dec-2-ene-3-carbonyl]-amino}-4-methyl-pentanoic acid tert-butyl ester |
| 148 | 3-{[8-(6-chloro-2-fluoro-3-methyl-benzoyl)-1-oxa-2,8-diaza-spiro[4,5]dec-2-ene-3-carbonyl-amino}-propionic acid ethyl ester |
| 149 | 8-(2-phenoxy-propionyl)-1-oxa-2,8-diaza-spiro[4,5]dec-2-ene-3-carboxylic acid benzylamide |
| 150 | 8-(5-fluoro-2-methyl-benzenesulphonyl)-1-oxa-2,8-diaza-spiro[4,5]dec-2-ene-3-carboxylic acid (thiophen-2-ylmethyl)-amide |
| 151 | [8-(5-chloro-thiophene-2-sulphonyl)-1-oxa-2,8-diaza-spiro[4,5]dec-2-en-3-yl]-[4-(2-methoxy-phenyl)-piperidin-1-yl]-methanone |
| 152 | 8-(2-chloro-benzoyl)-1-oxa-2,8-diaza-spiro[4,5]dec-2-ene-3-carboxylic acid (thiophen-2-ylmethyl)-amide |
| 153 | 8-(2-phenoxy-pyridine-3-carbonyl)-1-oxa-2,8-diaza-spiro[4,5]dec-2-ene-3-carboxylic acid cyclopentylamide |
| 154 | 8-(4-bromo-benzoyl)-1-oxa-2,8-diaza-spiro[4,5]dec-2-ene-3-carboxylic acid (2-ethylsulphanyl-ethyl-amide |
| 155 | 1-[8-(5-chloro-thiophene-2-sulphonyl)-1-oxa-2,8-diaza-spiro[4,5]dec-2-ene-3-carbonyl]-piperidine-2-carboxylic acid ethyl ester |
| 156 | 8-(2-chloro-benzenesulphonyl)-1-oxa-2,8-diaza-spiro[4,5]dec-2-ene-3-carboxylic acid (thiophen-2-ylmethyl)-amide |
| 157 | 8-(2,3-dichloro-benzoyl)-1-oxa-2,8-diaza-spiro[4,5]dec-2-ene-3-carboxylic acid cyclopropylmethyl-amide |
| 158 | 8-hexanoyl-1-oxa-2,8-diaza-spiro[4,5]dec-2-ene-3-carboxylic acid cyclopropylmethyl-amide |
| 159 | 8-(2,3-difluoro-4-methyl-benzoyl)-1-oxa-2,8-diaza-spiro[4,5]dec-2-ene-3-carboxylic acid cyclopropylmethyl-amide |
| 160 | 8-(4-fluoro-benzenesulphonyl)-1-oxa-2,8-diaza-spiro[4,5]dec-2-ene-3-carboxylic acid (2,5-dimethoxy-benzyl-furan-2-ylmethyl-amide |
| 161 | 8-dimethylsulphamoyl-1-oxa-2,8-diaza-spiro[4,5]dec-2-ene-3-carboxylic acid (2-ethylsulphanyl-ethyl-amide |
| 162 | 8-(4-trifluoromethoxy-benzenesulphonyl)-1-oxa-2,8-diaza-spiro[4,5]dec-2-ene-3-carboxylic acid 3-methoxy-benzylamide |
| 163 | 8-dimethylsulphamoyl-1-oxa-2,8-diaza-spiro[4,5]dec-2-ene-3-carboxylic acid (2-benzyloxy-cyclopentyl)-amide |
| 164 | 8-(4-methoxy-benzenesulphonyl)-1-oxa-2,8-diaza-spiro[4,5]dec-2-ene-3-carboxylic acid [2-(4-chloro-phenyl)-1-methyl-ethyl]-amide |
| 165 | 8-(4-trifluoromethoxy-benzenesulphonyl)-1-oxa-2,8-diaza-spiro[4,5]dec-2-ene-3-carboxylic acid [2-(3,4-dichloro-phenyl)-ethyl-amide |
| 166 | 8-[2-(3-chloro-phenoxy)-acetyl]-1-oxa-2,8-diaza-spiro[4,5]dec-2-ene-3-carboxylic acid benzylamide |
| 167 | 8-(4-fluoro-benzenesulphonyl)-1-oxa-2,8-diaza-spiro[4,5]dec-2-ene-3-carboxylic acid (2-cyano-ethyl)-(2-pyridin-2-yl-ethyl)-amide |
| 168 | 8-(5-chloro-thiophene-2-sulphonyl)-1-oxa-2,8-diaza-spiro[4,5]dec-2-ene-3-carboxylic acid [2-(4-chloro-phenyl)-1-methyl-ethyl]-amide |
| 169 | 8-(4-methoxy-benzenesulphonyl)-1-oxa-2,8-diaza-spiro[4,5]dec-2-ene-3-carboxylic acid (2-benzyloxy-cyclopentyl)-amide |
| 170 | 8-(2,6-difluoro-3-methyl-benzoyl)-1-oxa-2,8-diaza-spiro[4,5]dec-2-ene-3-carboxylic acid (thiophen-2-ylmethyl)-amide |
| 171 | 8-(2-benzyloxy-acetyl)-1-oxa-2,8-diaza-spiro[4,5]dec-2-ene-3-carboxylic acid benzylamide |
| 172 | 8-(2,3-dichloro-benzoyl)-1-oxa-2,8-diaza-spiro[4,5]dec-2-ene-3-carboxylic acid phenylamide |
| 173 | 8-(5-bromo-2-methoxy-benzenesulphonyl)-1-oxa-2,8-diaza-spiro[4,5]dec-2-ene-3-carboxylic acid cyclopentylamide |
| 174 | Acetic acid 2-(3-benzylcarbamoyl-1-oxa-2,8-diaza-spiro[4,5]dec-2-ene-8-yl)-1,1-dimethyl-2-oxo-ethyl ester |
| 175 | 8-[3-(2-chloro-6-fluorophenyl)-5-methyl-isoxazole-4-carbonyl]-1-oxa-2,8-diaza-spiro[4,5]dec-2-ene-3-carboxylic acid (2-ethylsulphanyl-ethyl)-amide |
| 176 | [4-(3-phenyl-propyl)-piperazin-1-yl]-[8-(4-trifluoromethoxy-benzenesulphonyl)-1-oxa-2,8-diaza-spiro[4,5]dec-2-en-3-yl]-methanone |
| 177 | 8-[3-(2-chloro-6-fluorophenyl)-5-methyl-isoxazole-4-carbonyl]-1-oxa-2,8-diaza-spiro[4,5]dec-2-ene-3-carboxylic acid benzylamide |
| 178 | 8-(naphthalene-1-carbonyl)-1-oxa-2,8-diaza-spiro[4,5]dec-2-ene-3-carboxylic acid isobutyl-amide |
| 179 | 1-[8-(5-tert-butyl-2-methyl-furan-3-carbonyl)-1-oxa-2,8-diaza-spiro[4,5]dec-2-ene-3-carbonyl]-piperidine-2-carboxylic acid ethyl ester |

TABLE 1-continued

| Example | Compound |
|---|---|
| 180 | 8-(3-difluoromethylsulphanyl-benzoyl)-1-oxa-2,8-diaza-spiro[4,5]dec-2-ene-3-carboxylic acid benzylamide |
| 181 | 8-(4-bromo-benzoyl)-1-oxa-2,8-diaza-spiro[4,5]dec-2-ene-3-carboxylic acid phenylamide |
| 182 | 8-(4-methoxy-benzenesulphonyl)-1-oxa-2,8-diaza-spiro[4,5]dec-2-ene-3-carboxylic acid (2-phenyl-cyclopropyl)-amide |
| 183 | 8-(4-phenoxy-butyryl)-1-oxa-2,8-diaza-spiro[4,5]dec-2-ene-3-carboxylic acid (thiophen-2-ylmethyl-amide |
| 184 | 8-(3-chloro-4-fluorobenzoyl)-1-oxa-2,8-diaza-spiro[4,5]dec-2-ene-3-carboxylic acid (thiophen-2-ylmethyl)-amide |
| 185 | 8-(5-tert-butyl-2-methyl-2H-pyrazole-3-carbonyl)-1-oxa-2,8-diaza-spiro[4,5]dec-2-ene-3-carboxylic acid (2-ethylsulphanyl-ethyl)-amide |
| 186 | [8-(4-fluoro-benzenesulphonyl)-1-oxa-2,8-diaza-spiro[4,5]dec-2-en-3-yl]-[4-(3-phenyl-propyl)-piperazin-1-yl]-methanone |
| 187 | 8-(4-trifluoromethoxy-benzoyl)-1-oxa-2,8-diaza-spiro[4,5]dec-2-ene-3-carboxylic acid (pyridin-4-ylmethyl)-amide |
| 188 | benzoic acid 2-(3-cyclopentylcarbamoyl-1-oxa-2,8-diaza-spiro[4,5]dec-2-ene-8-carbonyl-benzyl ester |
| 189 | 3-[4-(4-tert-butyl-benzyl)-piperazine-1-carbonyl]-1-oxa-2,8-diaza-spiro[4,5]dec-2-ene-8-sulphonic acid dimethylamide |
| 190 | {[8-(2-ethoxy-benzoyl)-1-oxa-2,8-diaza-spiro[4,5]dec-2-ene-3-carbonyl]-amino}-ethyl acetate |
| 191 | 8-(5-chloro-thiophene-2-sulphonyl)-1-oxa-2,8-diaza-spiro[4,5]dec-2-ene-3-carboxylic acid 2-benzyloxy-cyclopentyl)-amide |
| 192 | 8-(naphthalene-1-carbonyl)-1-oxa-2,8-diaza-spiro[4,5]dec-2-ene-3-carboxylic acid (thiophen-2-ylmethyl)-amide |
| 193 | 8-(4-fluoro-benzenesulphonyl)-1-oxa-2,8-diaza-spiro[4,5]dec-2-ene-3-carboxylic acid (3-phenyl-propyl)-amide |
| 194 | 8-(5-chloro-thiophene-2-sulphonyl)-1-oxa-2,8-diaza-spiro[4,5]dec-2-ene-3-carboxylic acid (2,3-dihydro-benzo[1,4]dioxin-2-ylmethyl)-amide |
| 195 | 1-[8-(4-tert-butyl-benzoyl)-1-oxa-2,8-diaza-spiro[4,5]dec-2-ene-3-carbonyl]-piperidine-2-carboxylic acid ethyl ester |
| 196 | 8-(4-fluoro-benzenesulphonyl)-1-oxa-2,8-diaza-spiro[4,5]dec-2-ene-3-carboxylic acid[2-(3-trifluoromethyl-phenyl-ethyl]-amide |
| 197 | 8-[3-(2,6-dichloro-phenyl)-5-methyl-isoxazole-4-carbonyl]-1-oxa-2,8-diaza-spiro[4,5]dec-2-ene-3-carboxylic acid (thiophen-2-ylmethyl)-amide |
| 198 | 8-(4-fluoro-benzenesulphonyl)-1-oxa-2,8-diaza-spiro[4,5]dec-2-ene-3-carboxylic acid[1-(naphthalen-2-ylcarbamoyl)ethyl]-amide |
| 199 | 8-(4-fluoro-benzenesulphonyl)-1-oxa-2,8-diaza-spiro[4,5]dec-2-ene-3-carboxylic acid (2-benzyloxy-cyclopentyl-amide |
| 200 | 3-(4-chloro-phenyl)-2-{[8-(4-methoxy-benzenesulphonyl)-1-oxa-2,8-diaza-spiro[4,5]dec-2-ene-3-carbonyl]-amino}-propionic acid methyl ester |
| 201 | 8-(3-trifluoromethyl-benzenesulphonyl)-1-oxa-2,8-diaza-spiro[4,5]dec-2-ene-3-carboxylic acid (2-benzyloxy-cyclopentyl)-amide |
| 202 | 8-(3-trifluoromethyl-benzenesulphonyl)-1-oxa-2,8-diaza-spiro[4,5]dec-2-ene-3-carboxylic acid (2-phenoxy-ethyl)-amide |
| 203 | 8-(2-phenoxy-pyridine-3-carbonyl)-1-oxa-2,8-diaza-spiro[4,5]dec-2-ene-3-carboxylic acid benzylamide |
| 204 | 8-(naphthalene-2-carbonyl)-1-oxa-2,8-diaza-spiro[4,5]dec-2-ene-3-carboxylic acid cyclopropylmethyl-amide |
| 205 | 8-(3-chloro-4-fluorobenzoyl)-1-oxa-2,8-diaza-spiro[4,5]dec-2-ene-3-carboxylic acid benzylamide |
| 206 | 8-(2-phenyl-butyryl)-1-oxa-2,8-diaza-spiro[4,5]dec-2-ene-3-carboxylic acid (2-cyano-ethyl)-amide |
| 207 | 8-(4-fluoro-benzenesulphonyl)-1-oxa-2,8-diaza-spiro[4,5]dec-2-ene-3-carboxylic acid 2 fluorobenzylamide |
| 208 | 8-(3-chloro-benzoyl)-1-oxa-2,8-diaza-spiro[4,5]dec-2-ene-3-carboxylic acid (thiophen-2-ylmethyl-amide |
| 209 | (4-benzyl-piperazin-1-yl)-[8-(2,5-dichloro-benzenesulphonyl)-1-oxa-2,8-diaza-spiro[4,5]dec-2-en-3-yl]-methanone |
| 210 | 8-(3-chloro-benzenesulphonyl)-1-oxa-2,8-diaza-spiro[4,5]dec-2-ene-3-carboxylic acid benzylamide |
| 211 | (4-benzyl-piperidin-1-yl)-[8-(3-trifluoromethyl-benzenesulphonyl)-1-oxa-2,8-diaza-spiro[4,5]dec-2-en-3-yl]-methanone |
| 212 | 8-(4-bromo-benzoyl)-1-oxa-2,8-diaza-spiro[4,5]dec-2-ene-3-carboxylic acid benzylamide |
| 213 | 8-(4-fluoro-benzenesulphonyl)-1-oxa-2,8-diaza-spiro[4,5]dec-2-ene-3-carboxylic acid[1-(4-nitro-phenyl)-ethyl]-amide |
| 214 | 4-methyl-2-{[8-(3-trifluoromethyl-benzenesulphonyl)-1-oxa-2,8-diaza-spiro[4,5]dec-2-ene-3-carbonyl]-amino}-pentanoic acid tert-butyl ester |
| 215 | [4-(4-fluoro-phenyl)-3,6-dihydro-2H-pyridin-1-yl]-(8-phenylmethanesulphonyl-1-oxa-2,8-diaza-spiro[4,5]dec-2-en-3-yl)-methanone |
| 216 | 8-dimethylsulphamoyl-1-oxa-2,8-diaza-spiro[4,5]dec-2-ene-3-carboxylic acid[2-(ethyl-m-tolyl-amino)-ethyl]amide |

TABLE 1-continued

| Example | Compound |
|---|---|
| 217 | 8-(2,5-dimethyl-furan-3-carbonyl)-1-oxa-2,8-diaza-spiro[4,5]dec-2-ene-3-carboxylic acid benzylamide |
| 218 | (4-cycloheptyl-piperazin-1-yl)-[8-(4-fluorobenzenesulphonyl)-1-oxa-2,8-diaza-spiro[4,5]dec-2-en-3-yl-methanone |
| 219 | 8-(2-benzyloxy-acetyl)-1-oxa-2,8-diaza-spiro[4,5]dec-2-ene-3-carboxylic acid benzylamide |
| 220 | R,R-8-(5-chloro-thiophene-2-sulphonyl)-1-oxa-2,8-diaza-spiro[4,5]dec-2-ene-3-carboxylic acid (2-benzyloxy-cyclopentyl)-amide |

Pharmacological Testing

Substituted 1-oxa-2,8-diaza-spiro[4,5]dec-2-ene derivatives according to the invention were subjected to the following pharmacological tests:

Bond Tests on the Sodium Channel

Binding Site 2 (BTX bond):

The binding site 2 of the sodium channel is what is known as the batrachotoxin (BTX) binding site. [$^3$H]-batrachotoxinin A20 α-benzoate (10 nM in a batch) was used as the ligand. These ion channel particles (synaptosomes) were enriched from rat cerebrocortex according to Gray and Whittaker (E. G. Gray and V. P. Whittaker (1962) J. Anat. 76, 79-88). The radioactivity measured in the presence of veratridine is defined as the unspecific bond. Incubation was carried out at 37° C. The assay conditions were adopted according to the publication by Pauwels, Leysen and Laduron (P. J. Pauwels, J. E. Leysen and P. M. Laduron (1986) Eur. J. Pharmacol. 124, 291-298).

TABLE 2

| Example | BTX bond, 10 µM, % inhibition |
|---|---|
| 1 | 68 |
| 2 | 55 |
| 3 | 78 |
| 5 | 64 |
| 6 | 49 |
| 8 | 63 |
| 11 | 69 |
| 14 | 79 |
| 15 | 88 |
| 16 | 60 |
| 18 | 53 |
| 19 | 66 |
| 20 | 69 |
| 21 | 63 |
| 23 | 60 |
| 24 | 41 |
| 26 | 84 |
| 27 | 74 |
| 28 | 52 |
| 30 | 56 |
| 31 | 80 |
| 32 | 66 |
| 33 | 67 |
| 35 | 50 |
| 37 | 70 |
| 38 | 65 |
| 40 | 47 |
| 45 | 49 |
| 47 | 71 |
| 48 | 43 |
| 50 | 87 |
| 52 | 63 |
| 53 | 47 |
| 55 | 47 |
| 57 | 45 |
| 61 | 79 |
| 62 | 49 |
| 63 | 38 |
| 64 | 91 |
| 65 | 67 |
| 67 | 80 |
| 69 | 50 |
| 71 | 54 |
| 73 | 75 |
| 74 | 47 |
| 79 | 83 |
| 80 | 44 |
| 83 | 72 |
| 84 | 58 |
| 85 | 62 |
| 87 | 42 |
| 88 | 45 |
| 89 | 81 |
| 91 | 72 |
| 92 | 65 |
| 93 | 52 |
| 96 | 72 |
| 97 | 79 |
| 98 | 56 |
| 99 | 50 |
| 102 | 43 |
| 103 | 53 |
| 106 | 62 |
| 108 | 43 |
| 115 | 48 |
| 119 | 72 |
| 121 | 42 |
| 124 | 54 |
| 126 | 56 |
| 127 | 70 |
| 133 | 47 |
| 135 | 85 |
| 136 | 44 |
| 140 | 60 |
| 141 | 61 |
| 144 | 53 |
| 146 | 67 |
| 149 | 40 |
| 150 | 86 |
| 152 | 56 |
| 153 | 41 |
| 155 | 48 |
| 156 | 70 |
| 160 | 75 |
| 163 | 40 |
| 164 | 52 |
| 166 | 58 |
| 168 | 69 |
| 169 | 48 |
| 170 | 59 |
| 171 | 44 |
| 172 | 60 |
| 173 | 62 |
| 176 | 76 |
| 177 | 45 |
| 179 | 55 |
| 180 | 57 |
| 181 | 50 |
| 182 | 47 |
| 183 | 68 |
| 184 | 73 |

TABLE 2-continued

| Example | BTX bond, 10 μM, % inhibition |
|---|---|
| 186 | 56 |
| 188 | 77 |
| 189 | 69 |
| 191 | 75 |
| 192 | 87 |
| 193 | 66 |
| 194 | 68 |
| 195 | 85 |
| 196 | 51 |
| 197 | 70 |
| 199 | 67 |
| 201 | 61 |
| 205 | 53 |
| 207 | 56 |
| 208 | 74 |
| 209 | 61 |
| 210 | 62 |
| 211 | 48 |
| 212 | 58 |
| 214 | 61 |
| 216 | 64 |
| 217 | 51 |
| 218 | 79 |

Tests on Noradrenalin Uptake Inhibition (NA-uptake Inhibition)

In order to be able to carry out these in vitro studies, synaptosomes from rat brain region were freshly isolated. A "P$_2$" fraction, prepared according to Gray and Whittaker's instructions (E. G. Gray and V. P. Whittaker (1962) J. Anat. 76, 79-88) was used in each case. These vesicular particles were isolated from the hypothalamus of male rats' brains for NA uptake.

The following characteristic data was ascertained for the NA transporter:

| | |
|---|---|
| NA-uptake: | Km = 0.32 ± 0.11 μM |

(N=4 in each case, i,e. average values±SEM from 4 independent test series which were carried out in three simultaneous tests).

A detailed description of the method can be found in the literature (M. Ch. Frink, H.-H. Hennies, W. Englberger, M. Haurand and B. Wilffert (1996) Arznein.-Forsch./Drug Res. 46 (III), 11, 1029-1036).

Compounds according to the invention were tested in this assay; the measured results are recited in Table 3:

TABLE 3

| Example | NA-uptake, 10 μM, % inhibition |
|---|---|
| 3 | 59 |
| 4 | 45 |
| 5 | 53 |
| 7 | 50 |
| 8 | 48 |
| 9 | 77 |
| 11 | 41 |
| 12 | 54 |
| 13 | 43 |
| 14 | 70 |
| 15 | 41 |
| 18 | 64 |
| 20 | 70 |
| 21 | 61 |
| 22 | 42 |
| 23 | 49 |
| 27 | 80 |
| 30 | 48 |
| 31 | 66 |
| 32 | 43 |
| 33 | 42 |
| 37 | 52 |
| 38 | 44 |
| 42 | 47 |
| 44 | 48 |
| 45 | 59 |
| 47 | 92 |
| 50 | 50 |
| 55 | 50 |
| 64 | 61 |
| 65 | 63 |
| 67 | 59 |
| 69 | 56 |
| 73 | 93 |
| 75 | 65 |
| 78 | 42 |
| 79 | 58 |
| 80 | 60 |
| 84 | 67 |
| 89 | 68 |
| 96 | 49 |
| 97 | 83 |
| 98 | 82 |
| 101 | 43 |
| 102 | 48 |
| 103 | 47 |
| 104 | 49 |
| 105 | 53 |
| 106 | 47 |
| 107 | 42 |
| 108 | 42 |
| 109 | 40 |
| 110 | 45 |
| 111 | 40 |
| 112 | 45 |
| 113 | 50 |
| 114 | 42 |
| 115 | 55 |
| 116 | 60 |
| 117 | 46 |
| 118 | 46 |
| 119 | 43 |
| 120 | 40 |
| 121 | 55 |
| 122 | 41 |
| 123 | 42 |
| 124 | 49 |
| 125 | 40 |
| 126 | 67 |
| 127 | 51 |
| 128 | 45 |
| 129 | 43 |
| 130 | 61 |
| 131 | 57 |
| 132 | 46 |
| 133 | 48 |
| 134 | 51 |
| 135 | 56 |
| 136 | 53 |
| 137 | 49 |
| 138 | 49 |
| 139 | 51 |
| 140 | 83 |
| 141 | 61 |
| 142 | 49 |
| 143 | 47 |
| 144 | 56 |
| 145 | 46 |
| 146 | 61 |
| 149 | 50 |
| 150 | 48 |
| 153 | 45 |
| 155 | 41 |
| 156 | 60 |

TABLE 3-continued

| Example | NA-uptake, 10 μM, % inhibition |
| --- | --- |
| 163 | 62 |
| 164 | 80 |
| 165 | 55 |
| 166 | 53 |
| 167 | 63 |
| 168 | 79 |
| 169 | 64 |
| 170 | 43 |
| 171 | 73 |
| 172 | 41 |
| 173 | 60 |
| 176 | 52 |
| 177 | 47 |
| 178 | 51 |
| 179 | 49 |
| 180 | 61 |
| 181 | 51 |
| 182 | 73 |
| 183 | 67 |
| 184 | 62 |
| 185 | 45 |
| 186 | 63 |
| 187 | 44 |
| 188 | 49 |
| 189 | 45 |
| 191 | 74 |
| 192 | 41 |
| 193 | 47 |
| 194 | 65 |
| 195 | 41 |
| 196 | 40 |
| 197 | 41 |
| 198 | 52 |
| 199 | 78 |
| 200 | 43 |
| 201 | 58 |
| 203 | 58 |
| 204 | 48 |
| 205 | 46 |
| 207 | 50 |
| 208 | 52 |
| 209 | 51 |
| 210 | 42 |
| 211 | 49 |
| 212 | 55 |
| 213 | 46 |
| 214 | 45 |
| 215 | 42 |
| 216 | 40 |
| 217 | 40 |
| 218 | 44 |

Tests on Serotonin Uptake (5HT Uptake Inhibition)

In order to be able to carry out these in vitro studies, synaptosomes from rat brain regions were freshly isolated. A "$P_2$" fraction prepared according to Gray and Whittaker's instructions (E. G. Gray and V. P. Whittaker (1962) J. Anat. 76, 79-88) was used in each case. These vesicular particles were isolated from the hypothalamus of male rats' brains for NA uptake.

A detailed description of the method can be found in the literature (M.Ch. Frink, H.-H. Hennies, W. Englberger, M. Haurand and B. Wilffert (1996) Arznein.-Forsch./Drug Res. 46 (III), 11, 1029-1036).

Compounds according to the invention were tested in this assay; the measured results are recited in Table 4:

TABLE 4

| Example | 5HT-uptake, 10 μM, % inhibition |
| --- | --- |
| 1 | 47 |
| 2 | 55 |
| 3 | 51 |
| 4 | 54 |
| 5 | 59 |
| 6 | 54 |
| 9 | 75 |
| 10 | 40 |
| 14 | 78 |
| 15 | 55 |
| 16 | 60 |
| 17 | 46 |
| 19 | 80 |
| 24 | 40 |
| 25 | 51 |
| 26 | 65 |
| 27 | 49 |
| 28 | 43 |
| 29 | 42 |
| 31 | 69 |
| 33 | 57 |
| 35 | 44 |
| 37 | 70 |
| 39 | 65 |
| 40 | 45 |
| 41 | 70 |
| 43 | 41 |
| 44 | 80 |
| 46 | 40 |
| 48 | 41 |
| 49 | 50 |
| 50 | 57 |
| 51 | 49 |
| 52 | 60 |
| 53 | 53 |
| 54 | 43 |
| 55 | 65 |
| 56 | 52 |
| 57 | 41 |
| 58 | 55 |
| 59 | 45 |
| 60 | 65 |
| 61 | 72 |
| 62 | 73 |
| 63 | 55 |
| 64 | 61 |
| 65 | 81 |
| 66 | 40 |
| 67 | 58 |
| 68 | 52 |
| 69 | 63 |
| 70 | 54 |
| 71 | 43 |
| 72 | 42 |
| 73 | 46 |
| 74 | 43 |
| 76 | 42 |
| 77 | 41 |
| 81 | 46 |
| 82 | 42 |
| 83 | 52 |
| 84 | 68 |
| 85 | 41 |
| 86 | 46 |
| 87 | 40 |
| 88 | 46 |
| 90 | 48 |
| 91 | 45 |
| 92 | 51 |
| 93 | 42 |
| 94 | 57 |
| 95 | 54 |
| 99 | 44 |
| 100 | 43 |
| 101 | 46 |
| 104 | 41 |
| 109 | 56 |
| 130 | 64 |
| 144 | 41 |
| 147 | 67 |

TABLE 4-continued

| Example | 5HT-uptake, 10 µM, % inhibition |
|---|---|
| 148 | 47 |
| 150 | 70 |
| 152 | 41 |
| 154 | 48 |
| 156 | 41 |
| 157 | 52 |
| 158 | 42 |
| 159 | 40 |
| 160 | 50 |
| 161 | 44 |
| 162 | 40 |
| 164 | 54 |
| 165 | 41 |

$\alpha_{2A}$-assay

The bond was measured here by the displacement of a marked ligand. The test was carried out according to J. P. Devlin's instructions, "High throughput screening—the discovery of bioactive substances", p. 275-453, Marcel Dekker, New York, 1997. Membranes containing α receptors of the subtypes (human) were obtained commercially.

Compounds according to the invention were tested in this assay: the measured results are recited in Table 5:

TABLE 5

| Example | alpha2A human, 1 µM, % inhibition |
|---|---|
| 21 | 31 |
| 27 | 37 |
| 151 | 33 |

Receptor bond (glycine binding site of the NMDA receptor channel)

Tests to determine the affinity of the compounds according to the invention to the glycine binding site of the NMDA receptor channel were carried on brain membrane homogenates (homogenate of cortex and hippocampus region from the brain of male rats, Wistar strain) [B. M. Baron, B. W. Siegel, B. L. Harrison, R. S. Gross, C. Hawes and P. Towers, Journal of Pharmacology and Experimental Therapeutics, Vol. 279, p. 62, 1996].

For this purpose, cortex and hippocampus from freshly removed rats' brains were freshly prepared and homogenized with ice cooling in 5 mmol/l TRIS-acetate buffer, 0.32 mol/l saccharose pH 7.4 (10 ml/g fresh weight) with a Potter homogenizer (Braun/Melsungen 10 piston strokes at 500 rpm) and then centrifuged for 10 minutes at 1,000 g and 4° C. The first supernatant was collected and the sediment again homogenized with 5 mmol/l TRIS-acetate buffer, 0.32 mol/l saccharose pH 7.4 (5 ml/g original fresh weight) with the Potter homogenizer (10 piston strokes at 500 rpm) with ice cooling and centrifuged for 10 minutes at 1,000 g and 4° C. The resultant supernatant was combined with the supernatant from the first centrifuging and centrifuged at 17,000 g for 20 minutes at 4° C. The supernatant after this centrifuging was discarded and the membrane sediment taken up with 5 mmol/l TRIS-acetate buffer pH 8.0 (20 ml/g original fresh weight) and homogenized with 10 piston strokes at 500 rpm. The membrane homogenate was then incubated for 1 hour at 4° C. and centrifuged for 30 minutes at 50,000 g and 4° C. The supernatant was discarded and the centrifuge tube with the membrane sediment sealed with parafilm and frozen for 24 hours at −20° C. The following day the membrane sediment was thawed and taken up with 5 mmol ice cold TRIS-acetate buffer, 0.1% saponin (w/v) pH 7.0 (10 ml/g original fresh weight) and homogenized with 10 piston strokes at 500 rpm and then centrifuged for 20 minutes at 50,000 g and 4° C. The resultant supernatant was discarded and the sediment taken up in a small volume with 5 mmol/l TRIS-acetate buffer pH 7.0 (about 2 ml/g original fresh weight) and again homogenized with 10 piston strokes at 500 rpm. After determining the protein content, the membrane homogenate was adjusted with 5 mmol/l TRIS-acetate buffer pH 7.0 to a protein concentration of 10 mg protein/ml and frozen in aliquots until testing.

For the receptor binding test aliquots were thawed, diluted 1:10 with 5 mmol/l TRIS-acetate buffer pH 7.0, homogenized with ice cooling with 10 piston strokes at 500 rpm using the Potter homogenizer (10 piston strokes at 500 rpm) and centrifuged for 60 minutes at 55,000 g at 4° C. The supernatant was decanted and the membrane sediment adjusted with 50 mmol ice cold TRIS-acetate buffer pH 7.0 to a protein concentration of 1 mg/ml and again homogenized with 10 piston strokes at 500 rpm and held in suspension in the ice bath while stirring on a magnetic stirrer. This membrane homogenate was used in the receptor binding test.

In the binding test 50 mmol/l TRIS-acetate buffer pH 7.0 was used as buffer and 1 mmol/l ($^3$H)-MDL 105.519 (B. M. Baron et al. 1996) was used as radioactive ligand. The non-specific bond content was determined in the presence of 1 mmol/l glycine.

In further batches the compounds according to the invention were added in concentration series and the displacement of the radioactive ligand from its specific bond to the glycine binding site of the NMDA receptor channel was ascertained. The batches were incubated for 120 minutes at 4° C. and then harvested to determine the radioactive ligand bound to the membrane homogenate by filtration through glass fiber filter mats (GF/B). The radioactivity retained on the glass fibre filters was measured in the β-counter after adding scintillator.

Compounds according to the invention were tested in this assay; the measured results are recited in Table 6:

TABLE 6

| Example | GlyB-bond, 10 µM, % inhibition |
|---|---|
| 34 | 37 |
| 36 | 38 |
| 137 | 36 |
| 174 | 41 |
| 175 | 91 |
| 190 | 89 |
| 202 | 59 |
| 206 | 39 |

Pharmaceutical Formulation of a Pharmaceutical Composition According to the Invention 1 g of the hydrochlorides of 8-(2,5-dichlorobenzenesulphonyl)-1-oxa-2,8-diaza5 spiro[4,5]dec-2-ene-3-carboxylic acid[1-(3-methoxybenzyl)-pyrrolidin-3-yl]amide (Example 64) was dissolved in 1 l water at ambient temperature for injection purposes and subsequently adjusted to isotonic conditions by adding sodium chloride.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A substituted 1-oxa-2,8-diaza-spiro[4,5]dec-2-ene compound corresponding to formula I

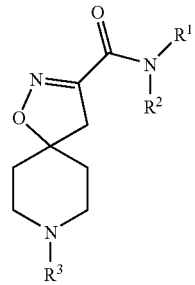

wherein
R$^1$ and R$^2$ independently of one another represent H, C$_{1-8}$-alkyl, C$_{3-8}$-cycloalkyl, (C$_{1-4}$-alkyl)-C$_{3-8}$-cycloalkyl, aryl, (C$_{1-4}$-alkyl)-aryl, heterocyclyl, (C$_{1-4}$-alkyl)-heterocyclyl or NH—C(=O)-aryl, wherein at least one of the radicals R$^1$ and R$^2$ does not represent H, or together represent —(CR$^4$R$^5$)$_m$—(CR$^6$R$^7$)$_n$—Y—(CR$^8$R$^9$)$_p$—(CR$^{10}$R$^{11}$)$_q$— where m=1, n=0 or 1, p=1 or 2 and q=1 or 2, or —CH$_2$—CH$_2$—C(-aryl)=CH—CH$_2$—;
R$^3$ represents COR$^{13}$;
R$^4$, R$^5$, R$^6$, R$^7$, R$^8$, R$^9$, R$^{10}$ and R$^{11}$ independently of one another represent H, C$_{1-8}$-alkyl, or C(=O)R$^{14}$;
Y represents CR$^{15}$R$^{16}$, or NR$^{17}$;
R$^{13}$ represents C$_{1-6}$-alkyl, C$_{3-10}$-cycloalkyl, aryl, (C$_{1-4}$-alkyl)-aryl, or heterocyclyl,
R$^{14}$ represents OR$^{20}$;
R$^{15}$ and R$^{16}$ independently of one another represent H, aryl, or (C$_{1-4}$-alkyl)-aryl;
R$^{17}$ represents H, C$_{3-8}$-cycloalkyl, aryl, (C$_{1-4}$-alkyl)-aryl, heterocyclyl or C(=O)R$^{22}$;
R$^{20}$ represents C$_{1-6}$-alkyl,
R$^{22}$ represents aryl, (C$_{1-4}$-alkyl)-aryl, heterocyclyl, or OR$^{24}$; and
R$^{24}$ represents C$_{1-6}$-alkyl, or (C$_{1-4}$-alkyl)aryl,
or a salt thereof with a physiologically tolerated acid.
2. The compound of claim 1, wherein said compound is present in the form of a free base.
3. The compound of claim 1, wherein said compound is present in the form of a pure enantiomer or pure diastereoisomer.
4. The compound of claim 1, wherein said compound is present in the form of a mixture of stereoisomers.
5. The compound of claim 1, wherein said compound is present in the form of a racemic mixture.
6. The compound of claim 1, wherein
R$^1$ represents C$_{1-6}$-alkyl, C$_{3-8}$-cycloalkyl, (C$_{1-3}$-alkyl)-C$_{3-8}$-cycloalkyl, aryl, (C$_{1-3}$-alkyl)-aryl, heterocyclyl, (C$_{1-3}$-alkyl-)heterocyclyl or NH—C(=O)-aryl; and
R$^2$ represents H, C$_{1-4}$-alkyl, (C$_{1-3}$-alkyl)-aryl or (C$_{1-3}$-alkyl)-heterocyclyl.
7. The compound of claim 1, wherein
R$^1$ represents methyl, ethyl, n-propyl, iso-propyl, 2-methylpropyl, n-butyl, tert.-butyl, n-phenyl, 3-methylbutyl or CH$_2$—C(CH$_3$)=CH$_2$, unsubstituted or substituted by F, Cl, Br, I, —CN, N-alkyl-N-arylamine, N,N-dialkylamine, amide, carboxyalkyl, carboxybenzyl; cyclopropyl, cyclobutyl, cyclopentyl, cyclohexyl, cycloheptyl, cyclooctyl or bicyclo [3.1.1]heptan-3-yl;
phenyl, 1-naphthyl or 2-naphthyl, unsubstituted or substituted by phenoxy or —CH$_2$—P(=O)(Oethyl)$_2$;
CH$_2$-aryl, CH$_2$—CH$_2$-aryl, CH$_2$—CH$_2$—CH$_2$-aryl, CH$_2$—CH$_2$—CH$_2$—CH$_2$-aryl CH(CH$_3$)-aryl, CH(CH$_3$)—CH$_2$-aryl, CH$_2$CH—(aryl)$_2$, CH(CO$_2$alkyl)—CH$_2$-aryl, CH$_2$—CH$_2$—CH—(aryl)$_2$, wherein aryl is unsubstituted phenyl, 1-naphthyl, 2-naphthyl or phenyl;
pyrrolidine or piperidine, unsubstituted or substituted by aryl, alkylaryl or carboxyethyl;
(CH$_2$)$_{1-3}$-heterocyclyl, unsubstituted or substituted by alkyl, F, Cl, Br, I, —CN, aryl, alkylaryl, wherein heterocyclyl represents furanyl, benzofuranyl, 1,4-dioxanyl, benzo-1,4-dioxanyl, thienyl, pyridinyl, pyrrolidinyl, 1H-indolyl, imidazolyl, piperidinyl or tetrahydrofuranyl; or
NH—C(=O)-(4-diethylaminophenyl); and
R$^2$ represents H;
methyl, ethyl, or CH$_2$—C(CH$_3$)=CH$_2$, unsubstituted or substituted by F, Cl, Br, I, —CN;
benzyl or phenethyl, unsubstituted or substituted by F, Cl, Br, I, —CN, methoxy or ethoxy; or
CH$_2$-furanyl, CH$_2$-benzofuranyl, CH$_2$-pyridinyl, CH$_2$-tetrahydrofuranyl or CH$_2$—CH$_2$-pyridinyl.
8. The compound of claim 7, wherein
R$^1$ represents methyl, ethyl, CH$_2$—C(CH$_3$)=CH$_2$, CH(C(=O)OCH$_2$—CH$_2$)—CH$_2$C(=O)O-tert.-butyl, 2-cyanoethyl, CH$_2$—CH$_2$—NH—C(=O)CH$_3$, 2-(N-ethyl-N-(3-methylphenyl)amino)-ethyl, 2-(N,N-dimethylamino)-ethyl, 2-(C(=O)—NH—(β-naphthyl)-ethyl, 1,2-(di(C(=O)O-tert.-butyl)ethyl, 3-(N-methyl-N-phenylamino)-propyl, 1-(C(=O)O-benzyl)-3-methyl-butyl, 1-(C(=O)O-butyl)-3-methyl-butyl, CH$_2$CO$_2$ethyl, CH$_2$—CH$_2$CO$_2$ethyl, CH$_2$—CH$_2$CO$_2$—Ophenyl, CH$_2$—CH$_2$—S—CH$_2$—CH$_3$, unsubstituted or substituted by F, Cl, Br, I, —CN, N-alkyl-N-arylamine, N,N-dialkylamine, amide, carboxyalkyl, carboxybenzyl;
cyclopropyl, cyclobutyl, cyclopentyl, cyclohexyl, cycloheptyl, cyclooctyl or bicyclo[3.1.1]heptan-3-yl.
9. The compound of claim 7, wherein
R$^1$ represents 2-phenylcyclopropyl, 2-(O-benzyl)-cyclopentyl, 2-(carboxyethyl)-cyclohexyl, 7,7-dimethyl-2-methylbicyclo [3.1.1]-heptan-3-yl; or
cyclopropylmethyl or 7,7-dimethyl-2-oxo-bicyclo [2.2.1]hept-1-ylmethyl, unsubstituted or substituted by F, Cl, Br, I, —CN, alkyl, aryl, carboxyalkyl, carboxybenzyl, O-alkyl or O-benzyl.
10. The compound of claim 7, wherein
R$^1$ represents benzyl, —CH$_2$-naphth-1-yl, 2-fluorobenzyl, 3-fluorobenzyl, 3-chlorobenzyl, 3-methoxybenzyl, 2-ethoxybenzyl, 2,4-difluorobenzyl, 3,5-dichlorobenzyl, 3-fluoro-5-trifluoromethylbenzyl, 3-fluoro-4-trifluoromethyl-benzyl, 2-chloro-6-fluorobenzyl, 2,5dimethoxybenzyl, 2-chloro-6-methyl-benzyl, 3,4-dimethoxybenzyl, 3,4-dioxymethylenebenzyl, CH(CH$_3$)phenyl, CH(CH$_3$)-(4-CH$_3$-phenyl), CH(CH$_3$)-(4nitrophenyl), CH(CH$_3$)-(2,3-dioxyethylenephenyl), CH$_2$CH$_2$-phenyl, CH$_2$—CH$_2$-(2-fluorophenyl), CH$_2$—CH$_2$-(3-fluorophenyl), CH$_2$—CH$_2$-(4-fluorophenyl), CH$_2$—CH$_2$-(4chlorophenyl), CH$_2$—CH$_2$-(3,4-dichlorophenyl), CH$_2$—CH$_2$(3-methoxyphenyl), CH$_2$—CH$_2$-(2,5-dimethoxyphenyl), CH(CO$_2$-tert.-butyl)-CH$_2$-phenyl, CH(CO$_2$-methyl)-CH$_2$(4-chlorophenyl), CH$_2$—CH(phenyl)$_2$, CH(CH$_3$)—CH$_2$-(4-chlorophenyl), CH$_2$—CH$_2$—CH(phenyl)$_2$ or CH$_2$—CH$_2$—CH$_2$-phenyl substituted by F, Cl, Br, I, —CN, —NO$_2$, alkyl, CF$_3$, alkoxy or alkylene dioxy.

11. The compound of claim 7, wherein
R$^1$ represents pyrrolidin-3-yl, N-(4-trifluorobenzyl)pyrrolidin-3-yl, N-(3-methoxybenzyl)-pyrrolidin-3-yl, N(CH$_2$-(β-naphthyl)-pyrrolidin-3-yl or N-(carboxyethyl)-piperidin-4-yl, unsubstituted or substituted by aryl, alkylaryl or carboxyethyl.

12. The compound of claim 7, wherein
R$^1$ represents CH$_2$-furan-2-yl, 5-methylfuran-2-yl CH$_2$-benzofuran-2-yl,

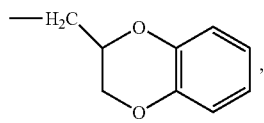,

CH$_2$-thien-2-yl, CH$_2$-pyridin-3-yl, CH$_2$-pyridin-4-yl, CH$_2$CH$_2$-pyridin-2-yl, CH$_2$—CH$_2$-(1H-indol-3-yl), CH$_2$—CH$_2$-pyrrolidin-1-yl, CH$_2$-(N-2,6-dichlorobenzyl-pyrrolidin-3-yl), CH$_2$—CH$_2$-(N-methyl-pyrrolidin-2-yl), —(CH$_2$)$_3$-imidazol-1-yl, CH$_2$-(tetrahydrofuran-2-yl) or

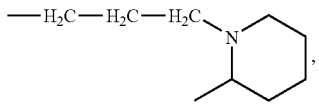, or CH(CO$_2$ methyl)-CH$_2$-(1H-indol-3-yl).

13. The compound of claim 7, wherein
R$^2$ represents methyl, ethyl, 2-cyanoethyl or CH$_2$—C(CH$_3$)=CH$_2$, unsubstituted or substituted by F, Cl, Br, I, —CN.

14. The compound of claim 7, wherein
R$^2$ represents benzyl, 4-fluorobenzyl, 2-chloro-6-fluorobenzyl, 2,5-dimethoxybenzyl or phenethyl, unsubstituted or substituted by F, Cl, Br, I, —CN, methoxy or ethoxy.

15. The compound of claim 7, wherein
R$^2$ represents CH$_2$-furan-2-yl, CH$_2$-benzofuran-2-yl, CH$_2$-pyridin-3-yl, CH$_2$-tetrahydrofuran-2-yl or CH$_2$—CH$_2$-pyridin-2-yl.

16. The compound of claim 1, wherein
R$^1$ and R$^2$ together represent

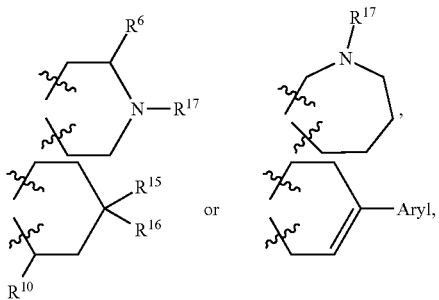

wherein aryl represents phenyl or phenyl substituted by F, Cl, Br or I;

R$^6$ represents H or C$_{1-4}$ alkyl;
R$^{10}$ represents H, C(=O)Omethyl, C(=O)Oethyl, C(=O)O-n-propyl, C(=O)O-iso-propyl, C(=O)O-n-butyl, C(=O)O-tert.-butyl;
R$^{15}$ represents H or CH$_2$-aryl;
R$^{16}$ represents H;
R$^{17}$ represents H;
  C$_{3-8}$-cycloalkyl;
  aryl, unsubstituted or substituted by methyl, ethyl, n-propyl, iso-propyl, n-butyl, tert.-butyl, CF$_3$, F, Cl, Br, I, —CN, methoxy, ethoxy, n-propoxy, isopropoxy, n-butoxy or tert.-butoxy;
  ((CH$_2$)$_{1-3}$-alkyl)-aryl or CH(CH$_3$)-aryl, wherein aryl represents phenyl or naphthyl, unsubstituted or substituted by alkyl, CF$_3$, F, Cl, Br, I, —CN or alkoxy;
  pyridinyl, pyrazinyl or thieno[2,3-d]pyrimidinyl, unsubstituted or substituted by alkyl, CF$_3$, F, Cl, Br, I, —CN or alkoxy; or C(=O)R$^{22}$; and
R$^{22}$ represents phenyl or alkoxy-substituted phenyl, O-methyl, O-ethyl, O-n-propyl, O-iso-propyl, O-n-butyl, O-tert.butyl, O-benzyl, unsubstituted benzyl, benzyl substituted by F, unsubstituted pyrazinyl or pyrazinyl substituted by alkyl.

17. The compound of claim 16, wherein aryl represents 4-fluorophenyl.

18. The compound of claim 16, wherein R$^6$ represents methyl.

19. The compound of claim 16, wherein R$^{17}$ represents cycloheptyl.

20. The compound of claim 16, wherein R$^{17}$ represents phenyl or naphthyl.

21. The compound of claim 1, wherein
R$^6$ represents H or methyl;
R$^{10}$ represents H or C(=O)Oethyl;
R$^{15}$ represents H or benzyl;
R$^{16}$ represents H; and
R$^{17}$ represents H;
  cycloheptyl, phenyl, 2-methylphenyl, 3-methylphenyl, 2,4-dimethylphenyl, 2-ethylphenyl, 4-fluorophenyl, 4-chlorophenyl, 2-methoxyphenyl, 3,5-dimethoxyphenyl, 3-chloro-6-methylphenyl, benzyl, CH$_2$-(4-tert.-butylphenyl), CH$_2$-(β-naphthyl), CH(CH$_3$)-phenyl, (CH$_2$)$_3$-phenyl, pyridin-2-yl, (4-trifluoromethyl)-pyridin-2-yl, thieno[2,3-d]pyrimidin-4-yl, C(=O)-(4-methoxyphenyl), C(=O)-benzyl, C(=O)—CH$_2$-(3,4-difluorophenyl), C(=O)-(2-methylpyrazin-5-yl) or C(=O)O-tert.-butyl or O-benzyl.

22. The compound of claim 1, wherein
R$^3$ represents COR$^{13}$ and
R$^{13}$ represents methyl, ethyl, n-propyl, iso-propyl, 2-methylpropyl, n-butyl, tert.-butyl, n-pentyl or 3-methylbutyl, unsubstituted or substituted by O-methyl, O-ethyl, O—(CH$_2$)$_2$OCH$_3$, O-benzyl or O-phenyl, wherein phenyl is unsubstituted or substituted by F, Cl, Br, I, —CN, O—C(=O)-methyl or O—C(=O)-ethyl;
  phenyl or naphthyl, unsubstituted or substituted by F, Cl, Br, I, —CN, phenyl, methyl, ethyl, n-propyl, iso-propyl, n-butyl, tert.-butyl, CF$_3$, F, Cl, Br, I, —CN, NO$_2$, methoxy, ethoxy, n-propoxy, iso-propoxy, n-butoxy, tert.-butoxy, OCF$_3$, OCHF$_2$, OCH$_2$F, SCF$_3$, SCHF$_2$, SCH$_2$F, SCH$_3$, CH$_2$ OC(=O)phenyl or —N(CH$_3$);
  unsubstituted or substituted (C$_{1-2}$-alkyl)-aryl; or
  furanyl, benzofuranyl, thienyl, pyridinyl, pyrazolyl, benzodihydropyranyl or isooxazolyl, unsubstituted or substituted by alkyl, CF$_3$, aryl, O-phenyl, chlorine, S-methyl or S-ethyl.

23. The compound of claim 22, wherein
R¹³ represents methyl, ethyl, n-propyl, n-butyl, tert.-butyl, n-pentyl, CH₂—O—CH₂—CH₂—OCH₃, CH(CH₃)—O-phenyl, CH₂—CH₂—C(=O)OCH₃, C(CH₃)₂—OC(=O)CH₃, CH₂—O-benzyl, CH₂—O—(3-chlorophenyl), CH₂—CH₂—CH₂—O-phenyl, CH(OC(=O)methyl)CH₃; cyclopropyl, 2-phenylcyclopropyl or 1-adamantyl, unsubstituted or substituted by O-methyl, O-ethyl, O—(CH₂)₂OCH₃, O-benzyl or O-phenyl, wherein phenyl is unsubstituted or substituted by F, Cl, Br, I, —CN, O—C(=O)-methyl or O—C(=O)-ethyl.

24. The compound of claim 22, wherein
R¹³ represents 4-fluorophenyl, 2-chlorophenyl, 3-chlorophenyl, 4-bromophenyl, 4-phenylphenyl (4-biphenyl), 4-ethylphenyl, 4-CF₃-phenyl, 4methoxyphenyl, 2-ethoxyphenyl, 4-tert.-butyl, 3-OCF₃-phenyl, 4-OCF₃-phenyl, 4-SCF₃-phenyl, 3-SCF₂-phenyl, 2—CH₂—OC(=O)phenyl, 3-dimethylaminophenyl, 2,3-dichlorophenyl, 2,4-difluorophenyl, 3-chloro-4-fluorophenyl, 3-chloro-2-fluorophenyl, 4-CF₃-3-fluorophenyl, 3-CF₃-6-fluorophenyl, 4-bromo-3-methylphenyl, 2-chloro-4-nitrophenyl, 2,3,4,5,6-pentafluorophenyl, 2,6-difluoro-3-methylphenyl, 2, 3-difluoro-4-methylphenyl, 2-chloro-5-methyl-6-fluorophenyl, 1-naphthyl or 2-naphthyl, unsubstituted or substituted by F, Cl, Br, I, —CN, phenyl, methyl, ethyl, n-propyl, iso-propyl, n-butyl, tert.-butyl, CF₃, F, Cl, Br, I, —CN, NO₂, methoxy, ethoxy, n-propoxy, iso-propoxy, n-butoxy, tert.-butoxy, OCF₃, OCHF₂, OCH₂F, SCF₃, SCHF₂, SCH₂F, SCH₃, CH₂OC(=O)phenyl or —N(CH₃).

25. The compound of claim 22, wherein R¹³ represents benzyl, phenethyl, CH(C₂H5)-phenyl, CH(NH—SO₂-(4-methyl-phenyl))-CH₂-phenyl, CH=CH-phenyl or CH=CH—(3-trifluorophenyl).

26. The compound of claim 22, wherein R¹³ represents 1,5-dimethylfuran-3-yl, 2methyl-5-tert.-butyl-furan-3-yl, 3-chlorothien-2-yl 1-(4-chlorophenyl)-5-trifluoro-methyl-pyrazol-4-yl, 1-methyl-3-tert.-butyl-pyrazol-5-yl,

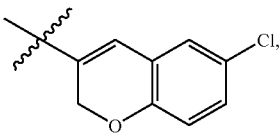

pyridin-4-yl, 2-methylthiopyridin-3-yl, 2-ethylthiopyridin-3-yl, 2-phenoxypyridin-3-yl, 2-chloropyridin-3-yl, 5-methyl-3-(2,6-dichlorophenyl)-isoxazol-4-yl or 5-methyl-3-(2-chloro-6-fluorophenyl)-isoxazol-4-yl, unsubstituted or substituted by alkyl, CF₃, aryl, O-phenyl, chlorine, S-methyl or S-ethyl.

27. The compound of claim 1, wherein said compound is selected from the group consisting of:

8-(2-chloro-4-nitro-benzoyl)-1-oxa-2,8-diaza-spiro[4.5]dec-2-ene-3-carboxylic acid cyclopentylamide 8-(2-chloro-pyridine-3-carbonyl)-1-oxa-2,8-diaza-spiro[4.5]dec-2-ene-3-carboxylic acid cyclopentylamide 8-[3-phenyl-2-(toluene-4-sulphonylamino)-propionyl]-1-oxa-2,8-diaza--spiro[4.5]dec-2-ene-3-carboxylic acid (pyridin-3-ylmethyl) amide 8-(5-fluoro-2-methyl-benzenesulphonyl)-1-oxa-2,8-diaza-spiro[4.5]dec-2-ene- carboxylic acid (2-dimethylamino-ethyl) amide 8-[3-phenyl-2-(toluene-4-sulphonylamino)-propionyl]-1-oxa-2,8-diaza -spiro[4.5]dec-2-ene-3-carboxylic acid (2-cyano-ethyl) amide 8-(3-dimethylamino-benzoyl)-1-oxa-2,8-diaza-spiro[4.5]dec-2-ene-3-carboxylic acid (2-cyano-ethyl) amide 8-acetyl-1-oxa-2,8-diaza-spiro[4.5]dec-2-ene-3-carboxylic acid benzyl amide 8-(4-ethyl-benzoyl)-1-oxa-2,8-diaza-spiro[4.5]dec-2-ene-3-carboxylic acid (thiophen-2-ylmethyl) amide 4-{[8-(2-phenyl-cyclopropanecarbonyl)-1-oxa-2,8-diaza-spiro[4.5]dec-2-ene-3-carbonyl]-amino}-piperidine-l-carboxylic acid ethylester 4-{[8-(2,4-difluoro-benzoyl)-1-oxa-2,8-diaza-spiro[4.5]dec-2-ene-3-carbonyl]-amino}-piperidine-1-carboxylic acid ethylester 8-(4-methoxy-benzoyl)-1-oxa-2,8-diaza-spiro[4.5]dec-2-ene-3-carboxylic acid (5-methyl-furan-2-ylmethyl) amide 4-{[8-(4-bromo-benzoyl)-1-oxa-2,8-diaza-spiro[4.5]dec-2-ene-3-carbonyl]-amino}-piperidine-1-carboxylic acid ethylester 4-[(8-Butyryl-1-oxa-2,8-diaza-spiro[4.5]dec-2-ene-3-carbonyl)-amino]--piperidine-1-carboxylic acid ethylester 3-{[8-(3,5-difluoro-benzoyl)-1-oxa-2,8-diaza-spiro[4.5]dec-2-ene-3-carbonyl]-amino}-propionic acid ethyl ester 8-butyryl-1-oxa-2,8-diaza-spiro[4.5]dec-2-ene-3-carboxylic acid phenylamide 8-[2-(2-methoxy-ethoxy)-acetyl]-1-oxa-2,8-diaza-spiro[4.5]dec-2-ene-3-carboxylic acid benzyl amide 8-(4-bromo-3-methyl-benzoyl)-1-oxa-2,8-diaza-spiro[4.5]dec-2-ene-3-carboxylic acid isobutyl amide 8-[2-(3-chloro-phenoxy)-acetyl]-1-oxa-2,8-diaza-spiro[4.5]dec-2-ene-3-carboxylic acid (thiophen-2-ylmethyl) amide 8-(pyridine-4-carbonyl)-1-oxa-2,8-diaza-spiro[4.5]dec-2-ene-3-carboxylic acid benzyl amide 8-(5-tert-butyl-2-methyl-furan-3-carbonyl)-1-oxa-2,8-diaza-spiro[4.5]dec-2-ene-3-carboxylic acid isobutyl amide 8-(3-phenyl-acryloyl)-1-oxa-2,8-diaza-spiro[4.5]dec-2-ene-3-carboxylic acid (thiophen-2-ylmethyl) amide 8-(4-trifluoromethyl-benzoyl)-1-oxa-2,8-diaza-spiro[4.5]dec-2-ene-3-carboxylic acid cyclopropylmethyl amide 8-(4-trifluoromethylsulphanyl-benzoyl)-1-oxa-2,8-diaza-spiro[4.5]dec-2-ene-3-carboxylic acid cyclopropylmethyl amide 8-(4-bromo-benzoyl)-1-oxa-2,8-diaza-spiro[4.5]dec-2-ene-3-carboxylic acid (5-methyl-furan-2-ylmethyl) amide 8-(3-fluoro-4-trifluoromethyl-benzoyl)-1-oxa-2,8-diaza-spiro[4.5]dec-2-ene-3-carboxylic acid cyclopropylmethyl amide 8-(2,4-difluoro-benzoyl)-1-oxa-2,8-diaza-spiro[4.5]dec-2-ene-3-carboxylic acid (tetrahydrofuran-2-ylmethyl) amide {[8-(3-chloro-thiophene-2-carbonyl)-1-oxa-2,8-diaza-spiro[4.5]dec-2-ene-3-carbonyl]-amino}-acetic acid ethylester 4-oxo-4-{3-[(thiophen-2-ylmethyl)-carbamoyl]-1-oxa-2,8-diaza--spiro[4.5]dec-2-ene-8-yl}-butyric acid methylester 8-(2-ethylsulphanyl-pyridine-3-carbonyl)-1-oxa-2,8-diaza-spiro[4.5]dec-2--ene-3- carboxylic acid benzyl amide 8-(4-trifluoromethoxy-benzoyl)-1-oxa-2,8-diaza-spiro[4.5]dec-2-ene-3-carboxylic acid cyclopropylmethyl amide 8-(4-phenoxy-butyryl)-1-oxa-2,8-diaza-spiro[4.5]dec-2-ene-3-carboxylic acid cyclopropylmethyl amide 8-(2-chloro-5-trifluoromethyl-benzoyl)-1-oxa-2,8-diaza-spiro[4.5]dec-2-ene-3-carboxylic acid cyclopropylmethyl amide 8-(2-phenoxy-propionyl)-1-oxa-2,8-diaza-spiro[4.5]dec-2-ene-3-carboxylic acid cyclopropylmethyl amide 8-(2-methylsulphanyl-pyridine-3-carbonyl)-1-oxa-2,8-diaza-spiro[4.5]dec--2-ene-3-carboxylic acid isobutyl amide 8-(5-tert-butyl-2-methyl-furan-3-carbonyl)-1-oxa-2,8-diaza-spiro[4.5]dec-2-ene-3- carboxylic acid cyclopentyl amide 8-(4-bromo-3-methyl-benzoyl)-1-oxa-2,8-diaza-spiro[4.5]dec-2-ene-3-carboxylic acid (pyridin-4-ylmethyl) amide 8-(4-methoxy-benzoyl)-1-oxa-2,8-diaza-spiro[4.5]dec-2-ene-3-carboxylic acid benzyl amide 8-(4-trifluoromethylsulphanyl-benzoyl)-1-oxa-2,8-diaza-spiro[4.5]dec-2-ene-3-carboxylic acid (thiophen-2-ylmethyl) amide 8-(4-fluoro-benzoyl)-1-oxa-2,8-diaza-spiro[4.5]dec-2-ene-3-carboxylic acid isobutyl amide 8-(4-bromo-benzoyl)-1-oxa-2,8-diaza-spiro[4.5]dec-2-ene-3-carboxylic acid (thiophen-2-ylmethyl) amide 8-(3-chloro-2-fluoro-benzoyl)-1-oxa-2,8-diaza-spiro[4,5]dec-2-ene-3-carboxylic acid (thiophen-2-ylmethyl) amide 3-{[8-(6-chloro-2-fluoro-3-methyl-benzoyl)-1-oxa-2,8-diaza-spiro[4,5]dec-2-ene-3- carbonyl]-amino}-propionic acid ethylester 8-(2-phenoxy-propionyl)-1-oxa-2,8-diaza-spiro[4,5]dec-2-ene-3-carboxylic acid benzyl amide 8-(2-chloro-benzoyl)-1-oxa-2,8-diaza-spiro[4,5]dec-2-ene-3-carboxylic acid (thiophen-2-ylmethyl) amide 8-(2-phenoxy-pyridine-3-carbonyl)-1-oxa-2,8-diaza-spiro[4,5]dec-2-ene-3-carboxylic acid cyclopentylamide 8-(4-bromo-benzoyl)-1-oxa-2,8-diaza-spiro[4,5]dec-2-ene-3-carboxylic acid (2-ethylsulphanyl-ethyl) amide 8-(2,3-dichloro-benzoyl)-1-oxa-2,8-diaza-spiro[4,5]dec-2-ene-3-carboxylic acid cyclopropylmethyl amide 8-(2,3-difluoro-4-methyl-benzoyl)-1-oxa-2,8-diaza-spiro[4.5]dec-2-ene-3-carboxylic acid cyclopropylmethyl amide 8-[2-(3-chloro-phenoxy)-acetyl]-1-oxa-2,8-diaza-spiro[4.5]dec-2-ene-3-carboxylic acid benzyl amide 8-(2,6-difluoro-3-methyl-benzoyl)-1-oxa-2,8-diaza-spiro[4.5]dec-2-ene-3-carboxylic acid (thiophen-2-ylmethyl) amide 8-(2-benzyloxy-acetyl)-1-oxa-2,8-diaza-spiro[4.5]dec-2-ene-3-carboxylic acid benzyl amide 8-(2,3-dichloro-benzoyl)-1-oxa-2,8-diaza-spiro[4.5]dec-2-ene-3-carboxylic acid phenylamide acetic acid 2-(3-benzylcarbamoyl-1-oxa-2,8-diaza-spiro[4.5]dec-2-en-8-yl)-1,1-dimethyl-2-oxo-ethylester 8-[3-(2-chloro-6-fluoro-phenyl)-5-methyl-isoxazole-4-carbonyl]-1-oxa-2,8-diaza- spiro[4.5]dec-2-ene-3-carboxylic acid (2-ethylsulphanyl-ethyl) amide 8-[3-(2-chloro-6-fluoro-phenyl)-5-methyl-isoxazole-4-carbonyl]-1-oxa-2,8-diaza- spiro[4.5]dec-2-ene-3-carboxylic acid benzyl amide 8-(naphthalene carbonyl)-1-oxa-2,8-diaza-spiro[4.5]dec-2-ene-3-carboxylic acid isobutyl amide 1-[8-(5-tert-butyl-2-methyl-furan-3-carbonyl)-1-oxa-2,8-diaza-spiro[4.5]dec-2-ene-3-carbonyl]-piperidin-2-carboxylic acid ethylester 8-(3-difluoromethylsulphanyl-benzoyl)-1-oxa-2,8-diaza-spiro[4.5]dec-2-ene-3-carboxylic acid benzyl amide 8-(4-bromo-benzoyl)-1-oxa-2,8-diaza-spiro[4.5]dec-2-ene-3-carboxylic acid phenylamide 8-(4-phenoxy-butyryl)-1-oxa-2,8-diaza-spiro[4.5]dec-2-ene-3-carboxylic acid (thiophen-2-ylmethyl) amide 8-(3-chloro-4-fluoro-benzoyl)-1-oxa-2,8-diaza-spiro[4.5]dec-2-ene-3-carboxylic acid (thiophen-2-ylmethyl) amide 8-(5-tert-butyl-2-methyl-2H-pyrazole-3-carbonyl)-1-oxa-2,8-diaza-spiro[4.5]dec-2-ene-3-carboxylic acid (2-ethylsulphanyl-ethyl) amide 8-(4-trifluoromethoxy-benzoyl)-1-oxa-2,8-diaza-spiro[4.5]dec-2-ene-3-carboxylic acid (pyridin-4-ylmethyl) amide benzoic acid 2-(3-cyclopentylcarbamoyl-1-oxa-2,8-diaza-spiro[4.5]dec-2-ene-8-carbonyl)-benzyl ester {[8-(2-ethoxy-benzoyl)-1-oxa-2,8-diaza-spiro[4.5]dec-2-ene-3-carbonyl]-amino}-acetic acid ethylester 8-(naphthalene-1-carbonyl)-1-oxa-2,8-diaza-spiro[4.5]dec-2-ene-3-carboxylic acid (thiophen-2-ylmethyl) amide 1-[8-(4-tert-butyl-benzoyl)-1-oxa-2,8-diaza-spiro[4.5]dec-2-ene-3-carbonyl]-piperidine-2-carboxylic acid ethyl ester 8-[3-(2,6-dichloro-phenyl)-5-methyl-isoxazole-4-carbonyl]-1-oxa-2,8-diaza-spiro[4.5]dec-2-ene-3-carboxylic acid (thiophen-2-ylmethyl) amide 8-(2-phenoxy-pyridine-3-carbonyl)-1-oxa-2,8-diaza-spiro[4.5]dec-2-ene-3-carboxylic acid benzyl amide 8-(naphthalene-2-carbonyl)-1-oxa-2,8-diaza-spiro[4.5]dec-2-ene-3-carboxylic acid cyclopropylmethyl amide 8-(3-chloro-4-fluoro-benzoyl)-1-oxa-2,8-diaza-spiro[4.5]dec-2-ene-3-carboxylic acid benzyl amide 8-(2-phenyl-butyryl)-1-oxa-2,8-diaza-spiro[4.5]dec-2-ene-3-carboxylic acid (2-cyano-ethyl) amide 8-(3-chloro-benzoyl)-1-oxa-2,8-diaza-spiro[4.5]dec-2-ene-3-carboxylic acid (thiophen-2-ylmethyl) amide 8-(4-bromo-benzoyl)-1-oxa-2,8-diaza-spiro[4.5]dec-2-ene-3-carboxylic acid benzyl amide 8-(2,5-dimethyl-furan-3-carbonyl)-1-oxa-2,8-diaza-spiro[4.5]dec-2-ene-3-carboxylic acid benzyl amide, and 8-(2-benzyloxy-acetyl)-1-oxa-2,8-diaza-spiro[4.5]dec-2-ene-3-carboxylic acid benzyl amide and the hydrochlorides thereof.

28. A process for producing a substituted 1-oxa-2,8-diaza-spiro[4,5]dec-2-ene compound corresponding to formula I of claim 1

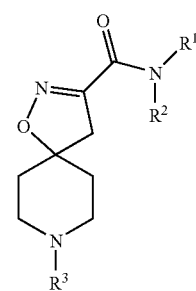

comprising the steps of:
(a) reacting a compound corresponding to formula (II)

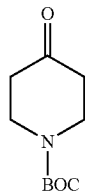

II with a methylenation agent to form a compound corresponding to formula (III)

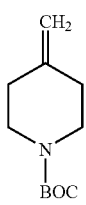

III (b) reacting the compound corresponding to formula (III) with ethyl chloroximidoacetate (IV)

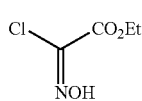

IV in the presence of a base, to form a 1-oxa-2,8-diaza-spiro[4,5]dec-2-ene compound corresponding to formula (V)

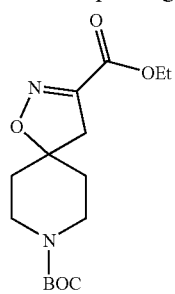

V (c) reacting the compound corresponding to formula (V) either directly or after previous saponification of the carboxylic acid ethyl ester function of the compound corresponding to formula (V) to form a 1-oxa-2,8-diaza-spiro[4,5]dec-2-ene compound corresponding to formula (VI)

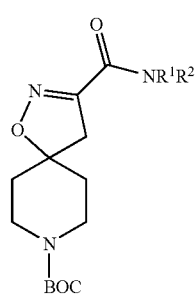

VI (d) removing the BOC protective group from the compound corresponding to formula (VI) to obtain the following compound:

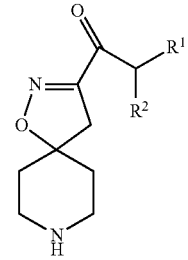

and converting

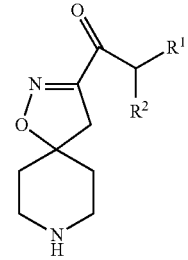

with a carboxylic acid chloride corresponding to formula $R^{13}COCl$ into a compound corresponding to formula (I)

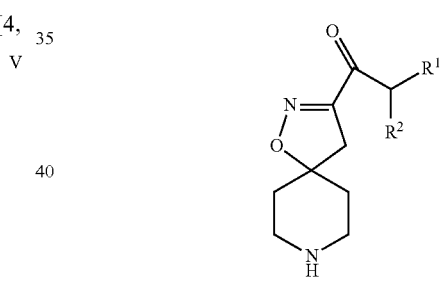

where $R^3$=$COR^{13}$.

29. The method of claim 28, wherein the methylenation agent of step (a) is $Ph_3PCH_3Br$ in the presence of potassium-tert.-butylate in THF.

30. The method of claim 28, wherein the base of step (b) is sodium hydrogen carbonate or lithium hydroxide.

31. The method of claim 28, wherein the reacting of step (b) occurs in the presence of an organic solvent.

32. The method of claim 31, wherein the organic solvent is methanol, dichloromethane or THF.

33. The method of claim 28, wherein the reacting of step (c) further comprises activating the carboxylic acid function with an amine corresponding to formula $HNR^1R^2$.

34. A pharmaceutical composition, comprising:
at least one substituted 1-oxa-2,8-diaza-spiro[4,5]dec-2-ene compound corresponding to formula (I) of claim 1 or a salt thereof with a physiologically tolerated acid and an auxiliary agent.

35. The pharmaceutical composition of claim 34, wherein said compound is present in the form of a free base.

36. The pharmaceutical composition of claim 34, wherein said compound is present in the form of a pure enantiomer or pure diastereoisomer.

37. The pharmaceutical composition of claim 34, wherein said compound is present in the form of a mixture of stereoisomers.

38. The pharmaceutical composition of claim 34, wherein said compound is present in the form of a racemic mixture.

39. The pharmaceutical composition of claim 34, wherein said compound is present in the form of a hydrochloride.

40. A method of alleviating pain in a mammal, said method comprising administering to said mammal an effective pain alleviating amount of a compound according to claim 1 or a salt thereof with a physiologically tolerated acid.

41. The method of claim 40, wherein said pain is neuropathic pain or chronic pain.

42. The method of claim 40, wherein said pain is pain from a migraine.

43. A method of anesthetizing a mammal, said method comprising administering to said mammal an effective amount of a compound according to claim 1 or a salt thereof with a physiologically tolerated acid.

44. The method of claim 43, wherein said method involves locally anesthetizing said mammal.

* * * * *